United States Patent
Brown

(10) Patent No.: US 12,311,011 B2
(45) Date of Patent: May 27, 2025

(54) DES-ACYL GHRELIN AND ANALOGS AS CANCER THERAPIES

(71) Applicant: Cornell University, Ithaca, NY (US)

(72) Inventor: Kristy A. Brown, New York, NY (US)

(73) Assignee: Cornell University, Ithaca, NY (US)

( * ) Notice: Subject to any disclaimer, the term of this patent is extended or adjusted under 35 U.S.C. 154(b) by 1076 days.

(21) Appl. No.: 17/271,067

(22) PCT Filed: Sep. 3, 2019

(86) PCT No.: PCT/US2019/049329
§ 371 (c)(1),
(2) Date: Feb. 24, 2021

(87) PCT Pub. No.: WO2020/051132
PCT Pub. Date: Mar. 12, 2020

(65) Prior Publication Data
US 2021/0196800 A1    Jul. 1, 2021

Related U.S. Application Data

(60) Provisional application No. 62/726,842, filed on Sep. 4, 2018.

(51) Int. Cl.
| | | |
|---|---|---|
| A61K 38/22 | (2006.01) | |
| A61K 38/12 | (2006.01) | |
| A61K 45/06 | (2006.01) | |
| A61P 35/00 | (2006.01) | |
| G01N 33/68 | (2006.01) | |

(52) U.S. Cl.
CPC .............. *A61K 38/22* (2013.01); *A61K 38/12* (2013.01); *A61K 45/06* (2013.01); *A61P 35/00* (2018.01); *G01N 33/68* (2013.01); *G01N 2800/52* (2013.01)

(58) Field of Classification Search
CPC ........ A61K 38/22; A61K 38/12; A61K 45/06; A61K 9/0019; A61K 9/08; A61K 31/704; A61K 38/25; A61K 47/02; A61P 35/00; G01N 33/68; G01N 2800/52; G01N 33/57407; G01N 2440/14

See application file for complete search history.

(56) References Cited

U.S. PATENT DOCUMENTS

| | | | | |
|---|---|---|---|---|
| 8,318,664 | B2 * | 11/2012 | Van Der Lely | A61K 38/25 514/4.8 |
| 2023/0330187 | A1 * | 10/2023 | Reid | A61K 38/22 |

FOREIGN PATENT DOCUMENTS

| | | | | |
|---|---|---|---|---|
| WO | WO-2008/145749 A1 | 12/2008 | | |
| WO | WO-2014203074 A2 * | 12/2014 | | A61K 38/22 |

OTHER PUBLICATIONS

Valtorta et al. KRAS gene amplification in colorectal cancer and impact on response to EGFR-targeted therapy. International Journal of Cancer, vol. 133, pp. 1259-1265. (Year: 2013).*
Ben-David et al. Genetic and transcriptional evolution alters cancer cell line drug response. Nature, vol. 560. pp. 325-330. (Year: 2018).*
Cassoni, et al., "Identification, Characterization, and Biological Activity of Specific Receptors for Natural (Ghrelin) and Synthetic Growth Hormone Secretagogues and Analogs in Human Breast Carcinomas and Cell Lines," The Journal of Clinical Endocrinology & Metabolism, Apr. 1, 2001, vol. 86, No. 4, pp. 1738-1745.
International Search Report and Written Opinion in International Patent Application No. PCT/US2019/049329 dated Jan. 24, 2020.
Nonaka, et al., "Therapeutic potential of ghrelin and des-acyl ghrelin against chemotherapy Induced cardiotoxicity," Endocrine Journal, Jun. 24, 2017, vol. 64, Issue Suppl., pp. S35-S39.

* cited by examiner

*Primary Examiner* — Marcela M Cordero Garcia
(74) *Attorney, Agent, or Firm* — Foley & Lardner LLP

(57) ABSTRACT

The present technology relates to methods for treating, preventing, and/or ameliorating cancer comprising administering a therapeutically effective amount of ghrelin, des-acyl ghrelin, or an analog thereof (e.g, the cyclic peptide analog AZP531) to a subject in need thereof. Kits for use in practicing the methods are also provided.

10 Claims, 81 Drawing Sheets

Specification includes a Sequence Listing.

*In Vitro*

Colorectal cancer cells

Colorectal cancer cells

Figure 11E
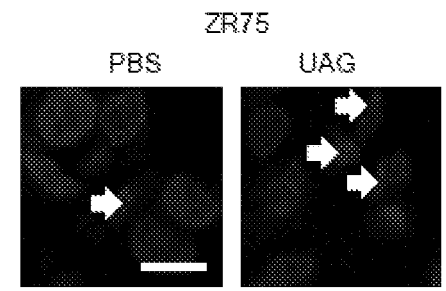
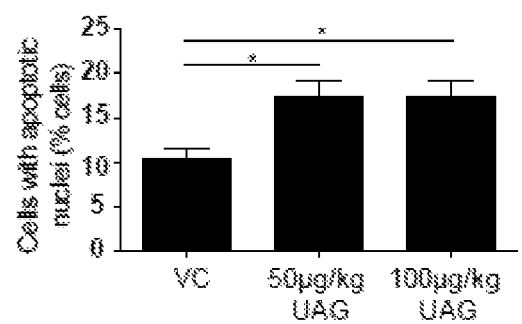
Figure 11F
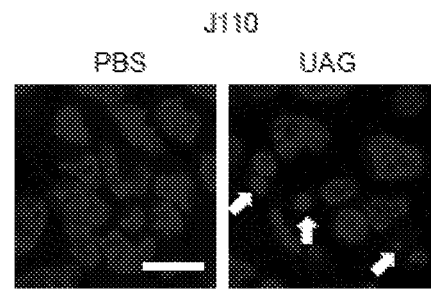
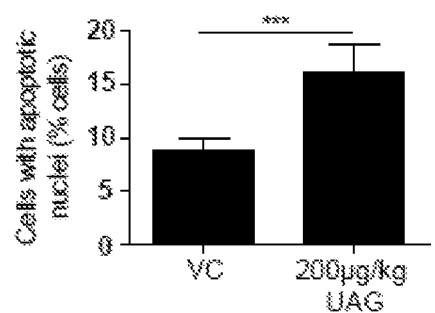

Figure 12C
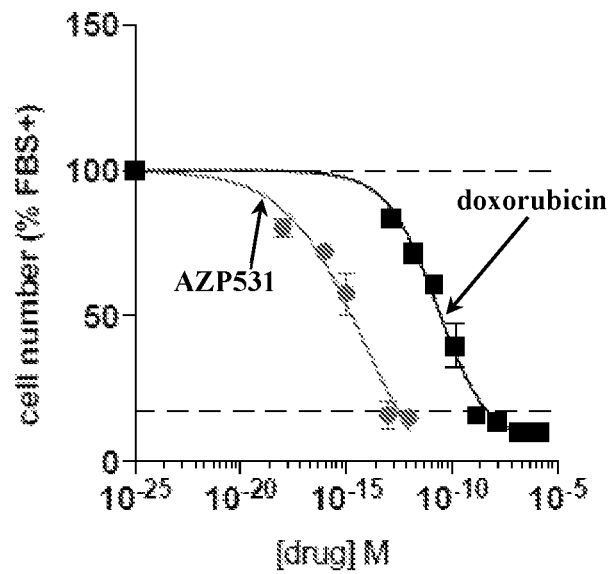
Figure 12D
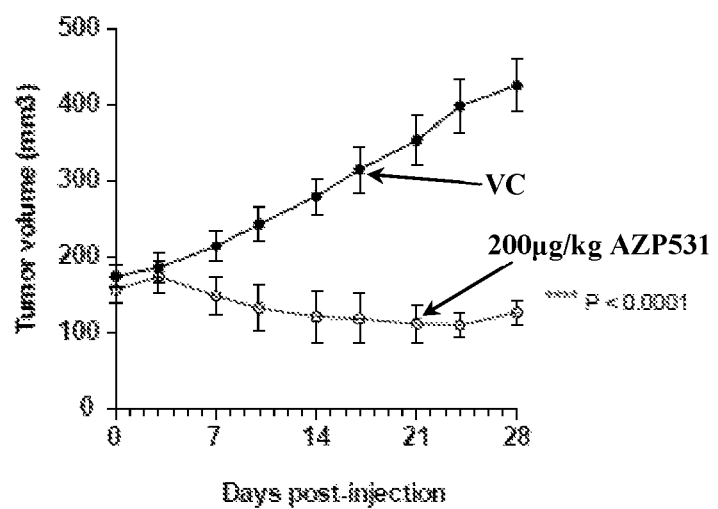
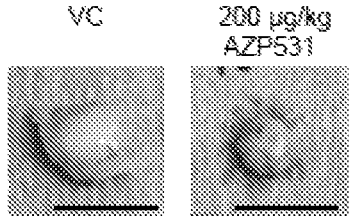

Figure 13

Table 1. Characteristics of breast cancer cell lines and patient-derived breast cancer cells, and responsiveness to unacylated ghrelin.

| Breast cancer cell line/ Patient sample | Known mutations | Intrinsic subtype | Receptor Status | Responsive to Unacylated Ghrelin |
|---|---|---|---|---|
| Cell line | | | | |
| MCF7 | CDKN2A, PIK3CA | Luminal A | ER+/PR+/HER2- | Yes |
| LCC2 | N/A | Luminal A | ER+/PR+/HER2- | Yes |
| T47D | PIK3CA, TP53 | Luminal A | ER+/PR+/HER2- | Yes |
| ZR75 | PTEN | Luminal B | ER+/PR+/HER2+ | Yes |
| SKBR3 | TP53 | HER2+ | HER2+ | Yes |
| MDA-MB 468 | PTEN, RB1, SMAD4, TP53 | Basal-like | TNBC | Yes |
| MDA-MB 157 | NF1, TP53 | Mesenchymal-like | TNBC | Yes |
| MDA-MB 231 | BRAF, KRAS, TP53, CDKN2A, NF2 | Mesenchymal-like | TNBC | No |
| HS578T | HRAS, TP53 | Mesenchymal-like | TNBC | No |
| DU4475 | BRAF, APC, MAP2K4, RB1 | Basal-like | TNBC | No |
| Patient samples | | | | |
| ER+ Case 1 | N/A | Luminal A | ER+ | Yes |
| ER+ Case 2 | N/A | Luminal A | ER+ | Yes |
| 2147-TG5 | N/A | Basal-like | TNBC | Yes |
| 4013-TG3 | N/A | Basal-like | TNBC | Yes |
| 3887-TG7 | N/A | Mesenchymal-like | TNBC | No |
| 3204-TG6 | N/A | Mesenchymal-like | TNBC | No |

Abbreviations: ER, estrogen receptor; PR, progesterone receptor; HER2, human epidermal growth factor receptor 2; TNBC, triple negative breast cancer; N/A: not available

Figure 14

| REAGENT or RESOURCE | SOURCE | IDENTIFIER |
|---|---|---|
| Antibodies | | |
| Goat anti-mouse IgG H&L (HRP) | Abcam | Cat# ab205719; RRID: AB_2755049 |
| Donkey anti-Rabbit IgG H&L (HRP) | Abcam | Cat# ab7083; RRID: AB_955416 |
| Mouse Monoclonal anti-Tubulin, beta, (KMX-1) | MilliporeSigma | Cat# MAB3408; RRID: AB_94650 |
| Mouse Monoclonal anti-β-Actin−Peroxidase | Sigma-Aldrich | Cat#A3854; RRID: AB_262011 |
| Rabbit Monoclonal anti-CDK4 (D9G3E) | Cell Signaling | Cat# 12790; RRID: AB_2631166 |
| Mouse Monoclonal anti-Cyclin D3 (DCS22) | Cell Signaling | Cat# 2936; RRID: AB_2070801 |
| Rabbit Polyclonal anti-phospho-Rb (Ser795) | Cell Signaling | Cat# 9301; RRID: AB_330013) |
| Mouse Monoclonal anti-Rb (4H1) | Cell Signaling | Cat# 9309; RRID: AB_823629 |
| Rabbit Monoclonal anti-Bcl-2 (D55G8) (Human Specific) | Cell Signaling | Cat# 4223; RRID: AB_1903909 |
| Rabbit Monoclonal anti-Bax | Cell Signaling | Cat# 2772; RRID: AB_10695870 |
| Rabbit Polyclonal anti-phospho-p44/42 MAPK (Erk1/2) (Thr202/Tyr204) | Cell Signaling | Cat# 9101; RRID: AB_331646 |
| Rabbit Monoclonal anti-p44/42 MAPK (Erk1/2) (137F5) | Cell Signaling | Cat# 4695; RRID: AB_390779 |
| Rabbit Monoclonal anti-phospho-p90RSK (Ser380) (D3H11) | Cell Signaling | Cat# 11989; RRID: AB_2687613 |
| Rabbit Monoclonal anti-RSK1/RSK2/RSK3 (32D7) | Cell Signaling | Cat# 9355; RRID: AB_659900 |
| Rabbit Monoclonal anti-c-Myc (D84C12) | Cell Signaling | Cat# 5605; RRID: AB_1903938 |
| Rabbit Monoclonal anti-phospho-p38 MAPK (Thr180/Tyr182) (D3F9) XP® | Cell Signaling | Cat# 4511; RRID: AB_2139682 |
| Rabbit Polyclonal anti-p38 MAPK | Cell Signaling | Cat# 9212; RRID: AB_330713 |
| Rabbit Monoclonal anti-p44/42 MAPK (Erk1/2) (137F5) | Cell Signaling | Cat# 4695; RRID: AB_390779 |
| Rabbit Polyclonal anti-phospho-Akt (Ser473) | Cell Signaling | Cat# 9271; RRID: AB_329825 |
| Rabbit Polyclonal anti-Akt | Cell Signaling | Cat# 9272; RRID: AB_329827 |
| Rabbit Monoclonal anti-phospho-p70 S6 Kinase (Thr389) (108D2) | Cell Signaling | Cat# 9234; RRID: AB_2269803 |
| Rabbit Monoclonal anti-p70 S6 Kinase (49D7) | Cell Signaling | Cat# 2708; RRID: AB_390722 |

| Figure 14 Cntd | | |
|---|---|---|
| Bacterial and Virus Strains | | |
| One Shot™ Stbl3™ Chemically Competent E. coli | ThermoFisher Scientific | Cat# C737303 |
| Biological Samples | | |
| Patient-derived breast tumors | obtained from Dr. Giorgio Inghirami | See Materials and Methods section |
| Estrogen receptor positive (ER+) breast tumors | obtained from Dr. Eleni Andreopoulou | See Materials and Methods section |
| Chemicals, Peptides, and Recombinant Proteins | | |
| [Des-octanoyl]-Ghrelin (rat) | Tocris Bioscience | Cat# 2951 |
| Rat des-octanoyl ghrelin | China Peptides | Cat# Rat des-octanoyl ghrelin |
| Ghrelin (rat) | Tocris Bioscience | Cat# 1465 |
| AZP531 | MedChem Express | Cat# HY-P0231 |
| Pertussis Toxin from *B. pertussis*, Lyophilized (Salt-Free) | List Biological Laboratories | Cat# 181 |
| U0126 | Cell Signaling | Cat# 9903S |
| LY294002 | Cell Signaling | Cat# 9901 |
| KT 5720 | Tocris Bioscience | Cat# 1288 |
| SQ 22536 | Tocris Bioscience | Cat# 1435 |
| cAMPS-Rp, triethylammonium salt | Tocris Bioscience | Cat# 1337 |
| Melatonin | Tocris Bioscience | Cat# 3550 |
| Hoechst 33342, Trihydrochloride, Trihydrate | ThermoFisher Scientific | Cat# H3570 |
| Cy3-tagged UAG | Pepmic Co, LtD | Cat# Cy3-GR-28 |
| BsmBI | New England BioLabs | Cat# R0580S |
| Polyethylenimine, linear (PEI) | Polysciences, Inc. | Cat# 23966-1 |
| Polybrene® | Santa Cruz Biotechnology | Cat# sc-134220 |
| Puromycin Dihydrochloride | ThermoFisher Scientific | Cat# A1113803 |
| Blasticidin S HCl (10 mg/mL) | ThermoFisher Scientific | Cat# A1113903 |
| Forskolin | Sigma-Aldrich | Cat# F3917 |
| Fura-2, AM, cell permeant | ThermoFisher Scientific | Cat# F1221 |
| Probenecid, Water Soluble | ThermoFisher Scientific | Cat# P36400 |
| Pluronic™ F-127 | ThermoFisher Scientific | Cat# P6867 |

| Figure 14 Cntd | | |
|---|---|---|
| Propidium Iodine | ThermoFisher Scientific | Cat# P1304MP |
| Doxorubicin hydrochloride | Sigma-Aldrich | Cat# D1515 |
| MK-2206 (hydrochloride) | Cayman Chemical | Cat# 11593 |
| NVP-BKM 120 | Cayman Chemical | Cat# 11587 |
| FITC Annexin V | BD Pharmingen | Cat# 556420 |
| β-Estradiol | Sigma-Aldrich | Cat# E8875-1G |
| Corning® Matrigel® Growth Factor Reduced (GFR) Basement Membrane Matrix, Phenol Red-free, *LDEV-free, | Corning | Cat# 356231 |
| Collagen | Obtained from Dr. Jason Spector | N/A |
| Critical Commercial Assays | | |
| EarlyTox™ Live/Dead Assay Kit | Molecular Devices | Cat# P/N R8340 |
| Click-iT™ Plus EdU Alexa Fluor™ 488 Imaging Kit | ThermoFisher Scientific | Cat# C10637 |
| Cell Line Nucleofector™ Kit V | Lonza | Cat# VCA-1003 |
| Lance Ultra cAMP Detection Kit | Perkin Elmer | Cat# TRF0262 |
| Gα$_i$ Activation Assay Kit | New East Biosciences | Cat# 80301 |
| Premo™ FUCCI Cell Cycle Sensor (BacMam 2.0) | ThermoFisher Scientific | Cat# P36237 |
| PureYield™ Plasmid Miniprep System | Promega | Cat# A1223 |
| PureYield™ Plasmid Maxiprep System | Promega | Cat# A2392 |
| Deposited Data | | |
| Microarray datasets | Zhang et al., 2013 | GEO2R: GSE34412 |
| Experimental Models: Cell Lines | | |
| MCF7 | ATCC | ATCC Cat# HTB-22; RRID: CVCL_0031 |
| T47D | ATCC | ATCC Cat# HTB-133; RRID: CVCL_0553 |
| ZR75-1 | ATCC | ATCC Cat# CRL-1500; RRID: CVCL_0588 |
| MDA-MB-231 | ATCC | ATCC Cat# HTB-26; RRID: CVCL_0062 |
| MDA-MB-468 | ATCC | ATCC Cat# HTB-132; RRID: CVCL_0419 |

| Figure 14 Cntd | | |
|---|---|---|
| SKBR3 | ATCC | ATCC Cat# HTB-30; RRID: CVCL_0033 |
| Hs578T | ATCC | ATCC Cat# HTB-126; RRID: CVCL_0332 |
| HEK293T | ATCC | ATCC Cat# CRL-1573; RRID: CVCL_0045 |
| DU4475 | ATCC | ATCC Cat# HTB-123; RRID: CVCL_1183 |
| MDA-MB-157 | ATCC | ATCC Cat# HTB-24; RRID: CVCL_0618 |
| LCC2 | obtained from Prof. Robert Clarke | N/A |
| RKO | Yun et al.,2009 | N/A |
| RKO-T29 | Yun et al.,2009 | N/A |
| RKO-A19 | Yun et al.,2009 | N/A |
| HCT116 | Yun et al.,2009 | N/A |
| HCT116-HWT | Yun et al.,2009 | N/A |
| HCT116-HMUT | Yun et al.,2009 | N/A |
| J110 | Obtained from Dr. Myles Brown | N/A |
| Experimental Models: Organisms/Strains | | |
| BALB/c-Foxn1$^{nu}$/Arc (BALB/c nude) mice | Animal Resources Centre, Australia | Cat# BCNU; RRID: MGI:2161064 |
| FVB/NJArc (FVB/N) mice | Animal Resources Centre, Australia | Cat# 001800; RRID: IMSR_JAX:001800 |
| NOD.Cg-Prkdc$^{scid}$Il2rg$^{tm1Wjl}$/SzJ (NSG) mice | NOD Scid gamma, Jackson laboratory | Cat# 005557; RRID: IMSR_JAX:005557 |
| Oligonucleotides (SEQ ID NOs. 5-22 in order of appearance) | | |
| GNAI1A sequence guide strands Forward: CACCGAGCACTGAGTGACTACGACC Reverse: AAACGGTCGTAGTCACTCAGTGCTC | This paper | N/A |
| GNAI1B sequence guide strands Forward: CACCGTTGCTATCATTAGGGCTATG Reverse: AAACATAGCCCTAATGATAGCAAC | This paper | N/A |
| GNAI1C sequence guide strands Forward: CACCGTGAAGCTGGTTATTCAGAAG Reverse: AAACCTTCTGAATAACCAGCTTCAC | This paper | N/A |

| Figure 14 Cntd | | |
|---|---|---|
| GNAI2A sequence guide strands<br>Forward: CACCGGACCCGCGTAAAGACCACG<br>Reverse: AAACCGTGGTCTTTACGCGGGTCCC | This paper | N/A |
| GNAI2B sequence guide strands<br>Forward: CACCGCTTTGCCGACCCCTCCAGAG<br>Reverse: AAACCTCTGGAGGGGTCGGCAAAGC | This paper | N/A |
| GNAI2C sequence guide strands<br>Forward: CACCGGCGTCATCCGGAGGCTCTGG<br>Reverse: AAACCCAGAGCCTCCGGATGACGCC | This paper | N/A |
| GNAI3A sequence guide strands<br>Forward: CACCGGATCGACCGCAACTTACGGG<br>Reverse:<br>AAACCCCGTAAGTAAGTTGCGGTCGATCC | This paper | N/A |
| GNAI3B sequence guide strands<br>Forward: CACCGTCATGAGGATGGCTATTCAG<br>Reverse: AAACCTGAATAGCCATCCTCATGAC | This paper | N/A |
| GNAI3C sequence guide strands<br>Forward: CACCGAGTCTAACTACATTCCAACT<br>Reverse: AAACAGTTGGAATGTAGTTAGACTC | This paper | N/A |
| Recombinant DNA | | |
| pPBJ—puro-FRET3-EKAR-nls | obtained from Dr. John Albeck | N/A |
| pCMV-hyPBase transposase vector | obtained from Dr. John Albeck | N/A |
| pMSCV-puro-Foxo3a-H212R-N400-mCherry | obtained from Dr. John Albeck | N/A |
| lentiCRISPR v2 | Sanjana et al., 2014 | Addgene Cat# 52961; RRID: Addgene_52961 |
| BRAFV600E plasmid | obtained from Dr. Dan Gough | N/A |
| psPAX2 | This paper | Addgene Cat# 12260; RRID: Addgene_12260 |
| VSV-G | Reya et al., 2003 | Addgene Cat# 14888; RRID: Addgene_14888 |
| Software and Algorithms | | |
| Prism | GraphPad | RRID: SCR_005375 |
| Imaris | Bitplane | RRID: SCR_007370 |
| Fiji | ImageJ | RRID: SCR_002285 |
| Image Lab | BIO-RAD | RRID: SCR_014210 |
| ZEN software | ZEISS | RRID: SCR_013672 |
| Ingenuity Pathway Analysis | Qiagen | RRID: SCR_008653 |
| FlowJo software | FlowJo | RRID: SCR_008520 |

MCF7 tumor size (Day 28)

ZR75 tumor size (Day 28)

DES-ACYL GHRELIN AND ANALOGS AS CANCER THERAPIES

CROSS-REFERENCE TO RELATED PATENT APPLICATIONS

This application is a U.S. National Phase Application under 35 U.S.C. § 371 of International Application No. PCT/US2019/049329, filed on Sep. 3, 2019, which claims the benefit of and priority to U.S. Provisional Appl. No. 62/726,842, filed Sep. 4, 2018, the disclosure of which is incorporated by reference herein in its entirety.

SEQUENCE LISTING

[001.1] The instant application contains a Sequence Listing which has been submitted electronically in ASCII format and is hereby incorporated by reference in its entirety. Said ASCII copy, created on Sep. 24, 2019, is named 093873-1219_SL.txt and is 6,537 bytes in size.

TECHNICAL FIELD

The present technology relates to methods for treating, preventing, and/or ameliorating cancer comprising administering a therapeutically effective amount of ghrelin, des-acyl ghrelin, or an analog thereof (e.g., the cyclic peptide analog AZP531) to a subject in need thereof. Kits for use in practicing the methods are also provided.

BACKGROUND

The following description of the background of the present technology is provided simply as an aid in understanding the present technology and is not admitted to describe or constitute prior art to the present technology.

Breast cancer is the most commonly diagnosed cancer in women and second only to lung cancer in terms of mortality. The majority of breast cancers occur after menopause and are hormone receptor positive, and in these women, first line therapy usually involves endocrine therapy, e.g., aromatase inhibitors or tamoxifen. Reinert, *Ther Adv Med Oncol* 6:304-20 (2015) (FIG. 6A). Despite the efficacy of endocrine therapy, a number of women experience severe and debilitating side effects due to the global inhibition of estrogen biosynthesis or action, and some will cease the use of their potentially life-saving treatment. Lønning and Eikesdal Endocr *Relat Cancer* 4: R183-201 (2013). A proportion of women will also be resistant to treatment or develop resistance over time, and some will have tumors that cannot be treated with targeted therapies, i.e., triple negative breast cancers (TNBCs). Aggressive breast cancers are often associated with activation of RAS/MAPK signaling, despite only a minority carrying a mutation in these genes. Giltnane and Balko, *Discov Med* 95:275-83 (2014); Santen et al., *J Steroid Biochem Mot Biol* 2:239-56 (2002); Tilch et al., *Breast Cancer Res Treat* 2:385-92 (2014). The prognosis for these patients is poor and hence, there is a need to identify alternative treatments that are safe and effective.

SUMMARY

In one aspect, the present disclosure provides a method for treating cancer in a subject in need thereof, comprising administering to the subject an effective amount of ghrelin, des-acyl ghrelin, or an analog thereof, wherein the cancer does not comprise a mutation in BRAF, HRAS, and KRAS. In some embodiments, the analog is a cyclic peptide comprising the amino acid sequence SPEHQRVQ (SEQ ID NO: 4). The cancer may be resistant to tamoxifen. Additionally or alternatively, in some embodiments, the effective amount of ghrelin, des-acyl ghrelin, or the analog is about 10-100 pM.

Additionally or alternatively, in certain embodiments, the cancer is colorectal cancer or breast cancer. The breast cancer may be $ER^+/PR^+/HER2^-$ breast cancer ("Luminal A" breast cancer"), $ER^+/PR^+/HER2^+$ ("Luminal B" breast cancer"), $ER^-/PR^-/HER2^+$ (HER2-positive breast cancer), or $ER^-/PR^-/HER2^-$ ("Triple Negative" breast cancer (TNBC)). In some embodiments, the subtype of the TNBC is basal-like or mesenchymal-like.

In any and all embodiments of the method, the subject harbors at least one mutation in one or more genes selected from the group consisting of CDKN2A, PIK3CA, TP53, PTEN, RB1, SMAD4, and NF1. Additionally or alternatively, in some embodiments, the subject exhibits at least one symptom selected from the group consisting of swelling in one or both breasts, redness or pitting of breast skin, change in breast size or shape, nipple discharge, breast pain, lumps on or inside the breast, itchy breasts, peeling or flaking of nipple skin, skin irritation or dimpling, nipple pain, nipple retraction, and lumps or swelling in underarm lymph nodes, diarrhea, constipation, narrowing of stool, rectal bleeding, dark or bloody stool, cramping, abdominal pain, fatigue, and unintended weight loss.

Additionally or alternatively, in some embodiments, the ghrelin, des-acyl ghrelin, or analog is administered intravenously, intramuscularly, intraarterially, intrathecally, intracapsularly, intraorbitally, intradermally, intraperitoneally, transtracheally, subcutaneously, intracerebroventricularly, orally, topically, intratumorally, or intranasally. In some embodiments, the ghrelin, des-acyl ghrelin, or analog is sequentially, simultaneously, or separately administered with at least one additional therapeutic agent. Examples of additional therapeutic agents include, but are not limited to, selective ER modulators (SERMs), selective estrogen receptor down-regulators (SERDs), aromatase inhibitors (AIs), and chemotherapeutic agents. In some embodiments, the at least one additional therapeutic agent is selected from the group consisting of anthracyclines (e.g., doxorubicin, pegylated liposomal doxorubicin, epirubicin), taxanes (e.g., paclitaxel, docetaxel, albumin-bound paclitaxel), 5-fluorouracil (5-FU), cyclophosphamide, carboplatin, cisplatin, vinorelbine, capecitabine, gemcitabine, ixabepilone, eribulin, irinotecan, oxaliplatin, trifluridine, tipiracil, tamoxifen, Fulvestrant (ICI 164384), exemestane, anastrozole, and letrozole. In any and all embodiments of the method, administration of the ghrelin, des-acyl ghrelin, or analog results in reduction in tumor size, reduced metastasis, and/or partial or complete remission compared to an untreated control subject suffering from cancer.

In one aspect, the present disclosure provides a method for monitoring the therapeutic efficacy of a pharmaceutical composition in a subject diagnosed with or suffering from cancer comprising: (a) detecting phosphorylation levels of one or more signaling proteins selected from the group consisting of ERK1/2, p90RSK, Akt, and p70S6K in a test sample obtained from the subject after the subject has been administered the pharmaceutical composition; and (b) determining that the pharmaceutical composition is effective when the phosphorylation levels of the one or more signaling proteins in the test sample are reduced compared to that observed in a control sample obtained from the subject prior to administration of the pharmaceutical composition, wherein the pharmaceutical composition comprises ghrelin, des-acyl ghrelin, or an analog thereof, and wherein the cancer does not comprise a mutation in BRAF, HRAS, and KRAS. In another aspect, the present disclosure provides a method for monitoring the therapeutic efficacy of a pharmaceutical composition in a subject diagnosed with or suffering from cancer comprising: (a) detecting expression levels of one or more genes selected from the group consisting of cMYC, CDK4/cyclin D3, pRB (Ser 795) and BCL2 in a test sample obtained from the subject after the subject has been administered the pharmaceutical composition; and (b) determining that the pharmaceutical composition is effective when the expression levels of the one or more genes in the test sample are reduced compared to that observed in a control sample obtained from the subject prior to administration of the pharmaceutical composition, wherein the pharmaceutical composition comprises ghrelin, des-acyl ghrelin, or an analog thereof, and wherein the cancer does not comprise a mutation in BRAF, HRAS, and KRAS. In some embodiments of the methods disclosed herein, the test sample is a tumor sample. Additionally or alternatively, in some embodiments, the methods of the present technology further comprise detecting levels of GTP-bound $G\alpha_i$, cell cycle arrest, and/or apoptosis in the test sample.

In yet another aspect, the present disclosure provides a method for reducing chemotherapy-induced side effects in a subject diagnosed with or suffering from cancer comprising: administering to the subject an effective amount of ghrelin, des-acyl ghrelin, or an analog thereof, and an effective amount of a chemotherapeutic agent, wherein the cancer does not comprise a mutation in BRAF, HRAS, and KRAS. Examples of chemotherapy-induced side effects include muscle cell death or cardiotoxicity. In some embodiments of the methods disclosed herein, the analog is a cyclic peptide comprising the amino acid sequence SPEHQRVQ (SEQ ID NO: 4). Additionally or alternatively, in some embodiments of the methods disclosed herein, the cancer is colorectal cancer or breast cancer. The breast cancer may be ER+/PR+/HER2− breast cancer ("Luminal A" breast cancer"), ER+/PR+/HER2+ ("Luminal B" breast cancer"), ER−/PR−/HER2+ (HER2-positive breast cancer), or ER−/PR−/HER2− ("Triple Negative" breast cancer (TNBC)). In some embodiments, the subtype of the TNBC is basal-like or mesenchymal-like. In any and all embodiments of the method, the subject harbors at least one mutation in one or more genes selected from the group consisting of CDKN2A, PIK3CA, TP53, PTEN, RB1, SMAD4, and NF1.

Also provided herein are kits comprising a composition including ghrelin, des-acyl ghrelin, or an analog thereof and instructions for using the same to treat a cancer that does not comprise a mutation in BRAF, HRAS, and KRAS. In some embodiments, the analog is a cyclic peptide comprising the amino acid sequence SPEHQRVQ (SEQ ID NO: 4). Additionally or alternatively, in some embodiments, the cancer is breast cancer or colorectal cancer.

BRIEF DESCRIPTION OF THE DRAWINGS

FIGS. 1A-1B shows that des-acyl ghrelin (UAG; 100 pM) inhibited the growth of a panel of breast cancer cell lines under serum-stimulated conditions (FIG. 1A), as well as ER+ breast cancer cell lines in the presence of estradiol (10 nM) (FIG. 1B), except if carrying RAS/RAF mutations. UAG: des-acyl ghrelin; E2: estradiol FIG. 2A shows that des-acyl ghrelin had no effect on the release of intracellular $Ca^{2+}$. FIG. 2B shows that the effect of des-acyl ghrelin was prevented in the presence of $G\alpha_i$, inhibitor, pertussis toxin (20 ng/ml, 200 ng/ml). FIG. 2C shows that des-acyl ghrelin inhibited forskolin-stimulated MCF7, ZR75 and MDA-MB 468 cell growth but not MDA-MB 231. FIG. 2D shows that a MAPK inhibitor inhibited forskolin-stimulated breast cancer cell growth. FIG. 2E shows a proposed model demonstrating that the inhibition of breast cancer cell growth by des-acyl ghrelin involves GaIRAF/MAPK signaling. UAG: des-acyl ghrelin; E2: estradiol; M: Melatonin.

FIG. 3A shows that des-acyl ghrelin significantly inhibited the proliferation of a panel of breast cancer cell lines in the absence or presence of estradiol (10 nM) or presence of serum. FIGS. 3B-3C show that the effects of des-acyl ghrelin were mediated via induction of G1-phase cell cycle arrest (FIG. 3B) and apoptosis (FIG. 3C).

FIGS. 4A-4I1 show that des-acyl ghrelin inhibited the growth of breast cancer cells in vivo and patient-derived breast cancer cells in vitro. FIGS. 4A-4B show the tumor volume in response to treatment with 50 mg/kg, or 100 mg/kg des-acyl ghrelin (UAG) in mice xenografted with MCF7 cells (FIG. 4A), ZR75 cells (FIG. 4B) (Nude mice).

FIGS. 5A-5B shows the results of proliferation assays performed in DAG-treated ZR75 and J110 cells in the presence of the $G\alpha_i$, inhibitor pertussis toxin (20 ng/ml, 200 ng/ml). FIG. 5C shows the effect of the MAPK inhibitor, U0126, on the growth of MCF7 in the presence of estradiol (10 nM). FIG. 5D shows the effect of the MAPK inhibitor, U0126, on the growth of MCF7 in the presence of serum. FIG. 5E shows the effect of the PI3K inhibitor, LY294002, on breast cancer cell growth in the presence of serum. UAG: des-acyl ghrelin; VC: vehicle control

FIG. 6B discloses SEQ ID NOS 2, 4 and 4, respectively, in order of appearance.

FIGS. 7A and 7C show that UAG (100 pM) inhibited the growth of a panel of breast cancer cell lines under serum-stimulated conditions. FIG. 7B shows that UAG (100 pM) inhibits the growth of ER+ breast cancer cell lines in the presence of estradiol (10 nM). FIG. 7C shows that UAG (100 pM) suppressed cell growth of basal-like and mesenchymal-like TNBC breast cancer cell lines that are WT for BRAF and KRAS. FIG. 7D shows that the effects of UAG on growth were abrogated in BRAF-transfected MCF7 cells. FIGS. 7E-7F show that the effects of UAG on growth are abrogated in (FIG. 7E) BRAF- and (FIG. 7F) KRAS-mutated colon cancer cells. Loss of mutated alleles of BRAF or KRAS sensitized cells to the effect of UAG. Data represent mean±SEM with n≥3. Experiment was repeated at least twice. UAG: unacylated ghrelin; VC: vehicle control; FBS: fetal bovine serum; E2: estradiol.

FIG. 8A shows that UAG (10-1000 pM) inhibited forskolin-stimulated production of cAMP in MCF7 cells. FIG. 8B shows that UAG (100 pM) mediated its effects via the activation of $G\alpha_i$. FIG. 8C shows that UAG (100 pM) suppressed the growth of CRISPR GNAI1 and GNAI3 KO cells, but not GNAI2 KO MCF7 cells, suggesting GNAI2-coupled GPCR-mediated effects. FIGS. 8C-8D shows that the suppression of estradiol—(FIG. 8D) or serum-stimulated (FIG. 8E) breast cancer cell growth by UAG (100 pM) was prevented in the presence of Gαi inhibitor, pertussis toxin (20 ng/ml, 200 ng/ml). FIG. 8F shows that PKA or adenylyl cyclase inhibitors or a cAMP antagonist also suppressed MCF7 breast cancer cell growth. FIG. 8G shows that UAG (100 pM) inhibited forskolin-stimulated growth of MCF7 and MDA-MB-468 cells, but not MDA-MB-231 cells. FIG. 8H shows that U0126 (MEK inhibitor) inhibited the forskolin-stimulated growth of MCF7, MDA-MB-468 and MDA-MB-231 cells. (I) A model summarizing the putative mechanism of action of UAG in breast cancer cells. Data represent mean±SEM with n≥3. Experiments were repeated at least twice. UAG: unacylated ghrelin; VC: vehicle control; FBS: fetal bovine serum; E2: estradiol; PT: pertussis toxin; M: melatonin; FSK: forskolin.

FIG. 9A shows that UAG (100 pM) inhibited ERK activity (EYFP FRET) in EKAR-transfected MCF7 cells. Data were normalized to ECFP signal. Scale bar represent 50 μm. FIGS. 9B-9E show western blots demonstrating that UAG caused a decrease in the phosphorylation of ERK1/2 and downstream MAPK target p90RSK (FIG. 9B) and expression of cMYC in MCF7 cells (FIG. 9C), while it had no effect on the phosphorylation of p38MAPK (FIG. 9D). UAG also caused a decrease in the phosphorylation of Akt and its downstream target, p70S6K (FIG. 9E). FIG. 9F shows FoxO3a nuclear localization in FoxO3a-RFP-transfected cells, an effect that is attenuated in cells treated with PI3K inhibitor LY294002. FIG. 9G shows that MK2206 (a highly selective inhibitor of pan-Akt) inhibited MDA-MB-468 cell growth in the presence of serum. FIG. 9H shows that BKM120 (a pan-class I PI3K inhibitor) inhibited MDA-MB-468 cell growth in the presence of serum. FIG. 9I shows that MK2206 inhibited MDA-MB 231 cell growth in the presence of serum. FIG. 9J shows that BKM120 inhibited MDA-MB 231 cell growth in the presence of serum. Data represent mean±SEM with n≥3. Experiment was repeated at least twice. UAG: unacylated ghrelin; FBS: fetal bovine serum FIGS. 10A-10C show that UAG significantly inhibited the proliferation of MCF7 (FIG. 10A), ZR75 (FIG. 10B) and MDA-MB-468 (FIG. 10C) cells in the presence of estradiol (10 nM) or serum. Representative images displayed showing EdU incorporation (green). Hoechst nuclear stain; blue. Scale bar represent 100 FIGS. 10D-10E show that the growth inhibitory effects of UAG were mediated via induction of G1-phase cell cycle arrest (RFP$^+$) and a reduction in the number of cells in S-(GFP$^+$) and G2-phase (YFP$^+$) in MCF7 (FIG. 10D) and MDA-MB-468 (FIG. 10E) cells. (Hoechst nuclear stain; blue). Scale bar represents 100 FIG. 10F shows that UAG stimulated cell death in MCF7 and MDA-MB-468 cells, but not MDA-MB-231 cells. FIGS. 10G-10I1 show western blots demonstrating that UAG inhibited CDK4/cyclin D3, pRB (Ser 795) and BCL2, and stimulated BAX in MCF7 (FIG. 10G) and MDA-MB-468 cells (FIG. 10I1). Data represent mean±SEM with n≥3. Experiments were repeated at least twice. UAG: unacylated ghrelin; VC: vehicle control; FBS: fetal bovine serum; E2: estradiol.

FIGS. 11A-11H show that unacylated ghrelin (UAG) inhibited tumor growth in xenograft models and patient-derived tumor cells. FIGS. 11A-11C show the line graphs of tumor volumes in response to treatment with 50 μg/kg (blue), 100 μg/kg (red) or 200 μg/kg (purple) UAG in mice xenografted with MCF7 (n=6/group) (FIG. 11A), ZR75 (FIG. 11B) (n=5/group), or allografted with J110 (n=5/group) cells (FIG. 11C). Representative tumors are shown in the bottom panels of FIGS. 11A-11C, with scale bar representing 10 mm. FIGS. 11D-11F show that UAG significantly increased the number of cells with apoptotic nuclei in MCF7 (FIG. 11D), ZR75 (FIG. 11E) xenografts and J110 allografts (FIG. 11F). FIG. 11G shows that UAG (100 pM) significantly inhibited the growth of patient-derived ER$^+$ breast cancer cells and basal-like (BL) TNBC cells, but not mesenchymal (M) TNBC cells. FIG. 11H shows a heatmap representing baseline differential expression of MAPK-target genes in responsive vs. non-responsive patient-derived cells. Data represent mean±SEM with n≥3. UAG: unacylated ghrelin; VC: vehicle control; FBS: fetal bovine serum.

FIGS. 12A-12E show that the cyclic unacylated ghrelin analog AZP531 inhibited the growth of breast cancer cells in vitro and in vivo. FIGS. 12A-12C show that AZP531 caused the dose-dependent inhibition of MCF7 (FIG. 12A) and MDA-MB-468 (FIG. 12B) and patient-derived TNBC breast cancer cell (FIG. 12C) growth in 3D, compared with chemotherapeutic agent doxorubicin. Data represent mean±SEM with n≥3. Experiments were repeated at least twice. FIGS. 12D-12E show the tumor volumes in response to treatment with 200 μg/kg AZP531 (purple) in mice xenografted with MDA-MB-468 (n=8-9/group) (FIG. 12D) or allografted with J110 (n=5/group) cells (FIG. 12E). Representative images (below) with scale bars representing 10 mm.

FIG. 13 shows the characteristics of the breast cancer cell lines and patient-derived breast cancer cells, and responsiveness to unacylated ghrelin.

FIG. 14 shows a list of the reagents and resources used in the Examples described herein.

FIGS. 15A-15B show that UAG (100 pM) inhibited the growth of MCF7 (FIG. 15A) and MDA-MB-468 (FIG. 15B) cells grown in 3D in matrigel or collagen, but not in 2D. FIG. 15C shows that UAG had no effect on MDA-MB-231 cell growth in 2D or 3D. FIGS. 15D-15F show the dose-dependent effects of UAG and doxorubicin on the growth of MCF7 (FIG. 15D), MDA-MB-468 (FIG. 15E) and MDA-MB-231 (FIG. 15F) cells in 3D. FIG. 15G shows that acyl ghrelin (AG) and UAG (100 pM) inhibit breast cancer cell growth in serum-stimulated conditions. FIG. 15H shows the binding of Cy3-labelled UAG to MCF7, MDA-MB-468 and MDA-MB-231 cells, representative image. Scale bar represents 20 µm. Data represent mean±SEM with n≥3. Experiments were repeated at least twice. UAG: unacylated ghrelin; AG: acylated ghrelin; VC: vehicle control; FBS: fetal bovine serum FIG. 16A shows that UAG has no effect on the release of intracellular $Ca^{2+}$ in MCF7 cells. FIG. 16B shows that UAG (100 pM) suppresses the growth of MDA-MB-468 CRISPR GNAI1 and GNAI3 KO cells, but not CRISPR GNAI2 KO cells, suggesting that UAG effects are via a GNAI2-coupled GPCR. FIG. 16C shows the suppression of estradiol-stimulated ZR75 cell growth by UAG (100 pM) is prevented by $G\alpha_i$ inhibitor, pertussis toxin (20 ng/ml, 200 ng/ml). FIG. 16D shows that PKA (KT5720) or adenylyl cyclase (SQ22536) inhibitors, or cAMP antagonist (cAMPS-RP) suppress the growth of MDA-MB-468 cells. FIG. 16E shows that UAG (100 pM) inhibits the forskolin-stimulated ZR75 cell growth. FIGS. 16F-16G show that U0126 (MEK inhibitor) (FIG. 16F) and MK2206 (Akt inhibitor) (FIG. 16G) inhibit the forskolin-stimulated growth of MDA-MB-468 and MDA-MB-231 cells. Data represent mean±SEM with n≥3. Experiments were repeated at least twice. UAG: unacylated ghrelin; FBS: fetal bovine serum; E2: estradiol; FSK: forskolin.

FIG. 17A shows the rapid effects of UAG on ERK activity are observed in EKAR-transfected MDA-MB 468 cells. FIGS. 17I-17J and 17L-17N show the effect of UAG on the phosphorylation of Akt and Akt downstream target, p70S6K, in MCF7 (FIG. 17L), MDA-MB-468 (FIGS. 17I and 17M) and MDA-MB-231 cells (FIGS. 17J and 17N).

FIG. 18A shows that UAG significantly inhibits the proliferation of LCC2 tamoxifen-resistant cells in the presence of estradiol (10 nM). Representative images showing EdU incorporation (green). (Hoechst nuclear stain; blue). Scale bar represent 100 µm. FIG. 18B shows that no effects of UAG on MDA-MB-231 cell cycle were observed when using FUCCI cell cycle system. FIG. 18C shows the unacylated ghrelin had no effect on CDK4/cyclin D3, pRB (Ser 795), BCL2, cMYC or BAX in MDA-MB-231 cells. FIGS. 18D-18I show flow cytometry analysis demonstrating that UAG induced G1-phase cell cycle arrest and apoptosis in MCF7 (FIGS. 18D-18E), MDA-MB-468 (FIGS. 18F-18G) and ZR75 (FIGS. 18H-18I), respectively. Data represent mean±SEM with n≥3. Experiments were repeated at least twice. UAG: unacylated ghrelin; FBS: fetal bovine serum; E2: estradiol.

FIGS. 19A-19B show representative images of tumor size in response to treatment with 50 µg/kg or 100 µg/kg UAG in nude mice xenografted with MCF7 (n=6/group) and (FIG. 19A) ZR75 (n=5/group) cells (FIG. 19B). FIGS. 19C-19D show the effect of UAG on tumor volume of J110 (n=5/group) allografts in FVB mice (FIG. 19C) or xenografts in nude mice compared to vehicle control (FIG. 19D). FIG. 19E shows that UAG (100 pM) significantly inhibited the growth of patient-derived ER+ breast cancer, basal-like (BL) TNBC, but not the growth of a mesenchymal (M) TNBC. Similar effects were observed when NSG mice xenografted with MDA-MB-468 (n=8/group) (FIG. 19F) and in FVB mice allografted with J110 (n=5/group) cells (FIG. 19G) were treated with 200 µg/kg AZP531. Scale bar represents 10 mm. Data represent mean±SEM with n≥3. Experiments were repeated at least twice. UAG: unacylated ghrelin; VC: vehicle control.

DETAILED DESCRIPTION

Figure 1A:
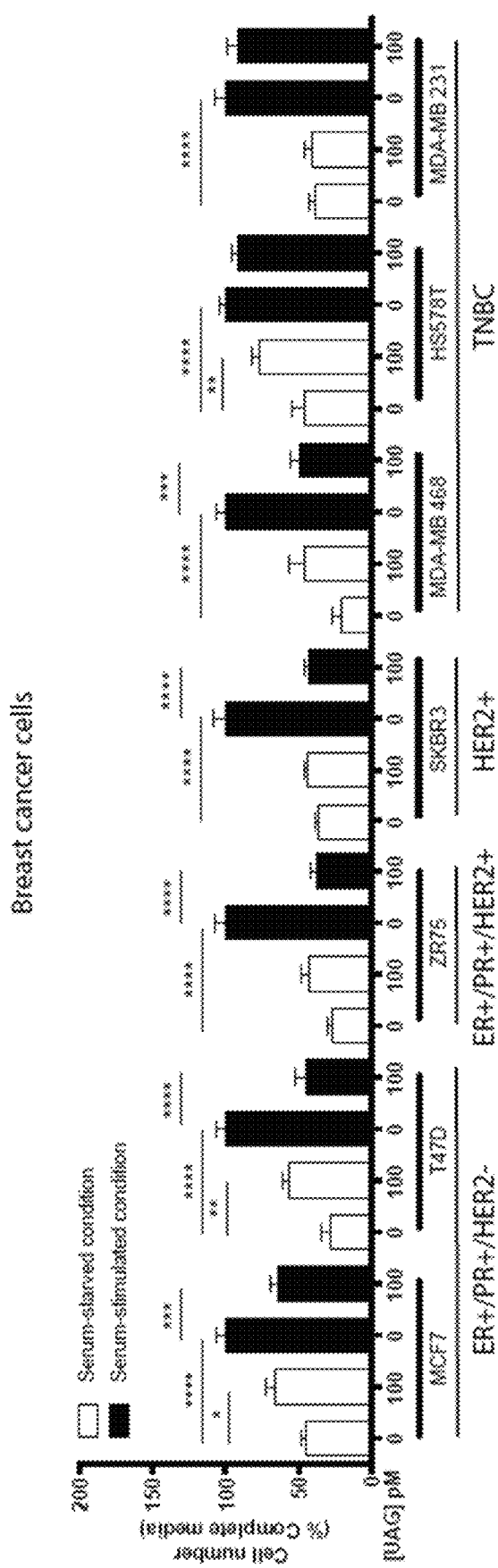
FIGS. 1A-1B show that des-acyl ghrelin (a.k.a., Unacylated ghrelin (UAG)) inhibited the growth of breast cancer cells dependent on RAS/RAF mutation status.

It is to be appreciated that certain aspects, modes, embodiments, variations and features of the present methods are described below in various levels of detail in order to provide a substantial understanding of the present technology.

In practicing the present methods, many conventional techniques in molecular biology, protein biochemistry, cell biology, immunology, microbiology and recombinant DNA are used. See, e.g., Sambrook and Russell eds. (2001) *Molecular Cloning: A Laboratory Manual*, 3rd edition; the series Ausubel et al. eds. (2007) *Current Protocols in Molecular Biology*; the series *Methods in Enzymology* (Academic Press, Inc., N.Y.); MacPherson et al. (1991) *PCR 1: A Practical Approach* (IRL Press at Oxford University Press); MacPherson et al. (1995) *PCR 2: A Practical Approach*; Harlow and Lane eds. (1999) *Antibodies, A Laboratory Manual*; Freshney (2005) *Culture of Animal Cells: A Manual of Basic Technique*, 5th edition; Gait ed. (1984) *Oligonucleotide Synthesis*; U.S. Pat. No. 4,683,195; Hames and Higgins eds. (1984) *Nucleic Acid Hybridization*; Anderson (1999) *Nucleic Acid Hybridization*; Hames and Higgins eds. (1984) *Transcription and Translation; Immobilized Cells and Enzymes* (IRL Press (1986)); Perbal (1984)

*A Practical Guide to Molecular Cloning*; Miller and Calos eds. (1987) Gene *Transfer Vectors for Mammalian Cells* (Cold Spring Harbor Laboratory); Makrides ed. (2003) *Gene Transfer and Expression in Mammalian Cells*; Mayer and Walker eds. (1987) *Immunochemical Methods in Cell and Molecular Biology* (Academic Press, London); and Herzenberg et al. eds (1996) *Weir's Handbook of Experimental Immunology*. Methods to detect and measure levels of polypeptide gene expression products (i.e., gene translation level) are well-known in the art and include the use of polypeptide detection methods such as antibody detection and quantification techniques. (See also, Strachan & Read, *Human Molecular Genetics*, Second Edition. (John Wiley and Sons, Inc., NY, 1999)).

The present disclosure demonstrates that unacylated ghrelin is a potent inhibitor of breast cancer cell growth and provides mechanistic insights not previously described for this peptide hormone. Little is known of the relationship between ghrelin, unacylated ghrelin and effects on breast cancer risk and progression. In the present disclosure, both ghrelin and unacylated ghrelin were found to cause potent inhibition of breast cancer cell growth at picomolar doses when cells are grown in a biologically relevant extracellular matrix (ECM). These findings were unexpected given that previous in vitro cell culture studies examining the effects of ghrelin and unacylated ghrelin in breast cancer saw very little effects at sub-micromolar doses (Cassoni et al., *J Clin Endocrinol Metab* 4:1738-45 (2001).

The present disclosure demonstrates that unacylated ghrelin treatment is associated with activation of $G\alpha_i$. The Examples described herein demonstrate that inhibition of cAMP formation or action mimics the effects of unacylated ghrelin to inhibit breast cancer cell growth in 3D culture models. Breast cancer cells that are insensitive to the effects of unacylated ghrelin in the presence of a BRAF or KRAS mutation suggests that unacylated ghrelin acts upstream of these signaling proteins. The effects of unacylated ghrelin with respect to inhibiting cell cycle progression and stimulating apoptosis are also consistent with inhibition of MAPK and Akt signaling. The present disclosure also demonstrates that the efficacy of AZP531 in reducing the growth of breast cancer cell lines and patient-derived cancer cells.

Based on the data obtained using a panel of breast cancer cell lines and effects seen in patient-derived tumor cells, the subset of breast cancers that were resistant to treatment were also identified, i.e., TNBCs with KRAS or BRAF mutations, or TNBCs with high MAPK activity. KRAS has been shown to maintain mesenchymal features of TNBCs. As less than 1% of breast tumors carry these mutations, it is likely that unacylated ghrelin and AZP531 will be effective in the majority of breast cancers. Since UAG has also been shown to prevent chemotherapy-induced muscle cell death, there is potential to combine unacylated ghrelin or AZP531 with chemotherapy, while also reducing cardiotoxicity.

Definitions

Unless defined otherwise, all technical and scientific terms used herein generally have the same meaning as commonly understood by one of ordinary skill in the art to which this technology belongs. As used in this specification and the appended claims, the singular forms "a", "an" and "the" include plural referents unless the content clearly dictates otherwise. For example, reference to "a cell" includes a combination of two or more cells, and the like. Generally, the nomenclature used herein and the laboratory procedures in cell culture, molecular genetics, organic chemistry, analytical chemistry and nucleic acid chemistry and hybridization described below are those well-known and commonly employed in the art.

As used herein, the term "about" in reference to a number is generally taken to include numbers that fall within a range of 1%, 5%, or 10% in either direction (greater than or less than) of the number unless otherwise stated or otherwise evident from the context (except where such number would be less than 0% or exceed 100% of a possible value).

As used herein, the "administration" of an agent or drug to a subject includes any route of introducing or delivering to a subject a compound to perform its intended function. Administration can be carried out by any suitable route, including orally, intranasally, parenterally (intravenously, intramuscularly, intraperitoneally, or subcutaneously), or topically. Administration includes self-administration and the administration by another.

As used herein, the terms "cancer," "neoplasm," and "tumor," are used interchangeably and refer to cells that have undergone a malignant transformation that makes them pathological to the host organism. Primary cancer cells (that is, cells obtained from near the site of malignant transformation) can be readily distinguished from non-cancerous cells by well-established techniques, particularly histological examination. The definition of a cancer cell, as used herein, includes not only a primary cancer cell, but any cell derived from a cancer cell ancestor. This includes metastasized cancer cells, and in vitro cultures and cell lines derived from cancer cells. When referring to a type of cancer that normally manifests as a solid tumor, a "clinically detectable" tumor is one that is detectable on the basis of tumor mass; e.g., by procedures such as CAT scan, MR imaging, X-ray, ultrasound or palpation, and/or which is detectable because of the expression of one or more cancer-specific antigens in a sample obtainable from a patient.

The terms "complementary" or "complementarity" as used herein with reference to polynucleotides (i.e., a sequence of nucleotides such as an oligonucleotide or a target nucleic acid) refer to the base-pairing rules. The complement of a nucleic acid sequence as used herein refers to an oligonucleotide which, when aligned with the nucleic acid sequence such that the 5' end of one sequence is paired with the 3' end of the other, is in "antiparallel association." For example, the sequence "5'-A-G-T-3'" is complementary to the sequence "3'-T-C-A-5." Certain bases not commonly found in naturally-occurring nucleic acids may be included in the nucleic acids described herein. These include, for example, inosine, 7-deazaguanine, Locked Nucleic Acids (LNA), and Peptide Nucleic Acids (PNA). Complementarity need not be perfect; stable duplexes may contain mismatched base pairs, degenerative, or unmatched bases. Those skilled in the art of nucleic acid technology can determine duplex stability empirically considering a number of variables including, for example, the length of the oligonucleotide, base composition and sequence of the oligonucleotide, ionic strength and incidence of mismatched base pairs. A complementary sequence can also be an RNA sequence complementary to the DNA sequence or its complementary sequence, and can also be a cDNA.

As used herein, a "control" is an alternative sample used in an experiment for comparison purpose. A control can be "positive" or "negative." For example, where the purpose of the experiment is to determine a correlation of the efficacy of a therapeutic agent for the treatment for a particular type of disease or condition, a positive control (a compound or composition known to exhibit the desired therapeutic effect)

and a negative control (a subject or a sample that does not receive the therapy or receives a placebo) are typically employed.

As used herein, the term "effective amount" refers to a quantity sufficient to achieve a desired therapeutic and/or prophylactic effect, e.g., an amount which results in the prevention of, or a decrease in a disease or condition described herein or one or more signs or symptoms associated with a disease or condition described herein. In the context of therapeutic or prophylactic applications, the amount of a composition administered to the subject will vary depending on the composition, the degree, type, and severity of the disease and on the characteristics of the individual, such as general health, age, sex, body weight and tolerance to drugs. The skilled artisan will be able to determine appropriate dosages depending on these and other factors. The compositions can also be administered in combination with one or more additional therapeutic compounds. In the methods described herein, the therapeutic compositions may be administered to a subject having one or more signs or symptoms of a disease or condition. As used herein, a "therapeutically effective amount" of a composition refers to composition levels in which the physiological effects of a disease or condition are ameliorated or eliminated. A therapeutically effective amount can be given in one or more administrations.

As used herein, "expression" includes one or more of the following: transcription of the gene into precursor mRNA; splicing and other processing of the precursor mRNA to produce mature mRNA; mRNA stability; translation of the mature mRNA into protein (including codon usage and tRNA availability); and glycosylation and/or other modifications of the translation product, if required for proper expression and function.

As used herein, the term "gene" means a segment of DNA that contains all the information for the regulated biosynthesis of an RNA product, including promoters, exons, introns, and other untranslated regions that control expression.

"Homology" or "identity" or "similarity" refers to sequence similarity between two peptides or between two nucleic acid molecules. Homology can be determined by comparing a position in each sequence which may be aligned for purposes of comparison. When a position in the compared sequence is occupied by the same nucleobase or amino acid, then the molecules are homologous at that position. A degree of homology between sequences is a function of the number of matching or homologous positions shared by the sequences. A polynucleotide or polynucleotide region (or a polypeptide or polypeptide region) has a certain percentage (for example, at least 60%, 65%, 70%, 75%, 80%, 85%, 90%, 95%, 98% or 99%) of "sequence identity" to another sequence means that, when aligned, that percentage of bases (or amino acids) are the same in comparing the two sequences. This alignment and the percent homology or sequence identity can be determined using software programs known in the art. In some embodiments, default parameters are used for alignment. One alignment program is BLAST, using default parameters. In particular, programs are BLASTN and BLASTP, using the following default parameters: Genetic code=standard; filter=none; strand=both; cutoff=60; expect=10; Matrix=BLOSUM62; Descriptions=50 sequences; sort by =HIGH SCORE; Databases=non-redundant, GenBank+EMBL+DDBJ+PDB+GenBank CDS translations+SwissProtein+SPupdate+PIR. Details of these programs can be found at the National Center for Biotechnology Information. Biologically equivalent polynucleotides are those having the specified percent homology and encoding a polypeptide having the same or similar biological activity. Two sequences are deemed "unrelated" or "non-homologous" if they share less than 40% identity, or less than 25% identity, with each other.

The term "hybridize" as used herein refers to a process where two substantially complementary nucleic acid strands (at least about 65% complementary over a stretch of at least 14 to 25 nucleotides, at least about 75%, or at least about 90% complementary) anneal to each other under appropriately stringent conditions to form a duplex or heteroduplex through formation of hydrogen bonds between complementary base pairs. Nucleic acid hybridization techniques are well known in the art. See, e.g., Sambrook, et al., 1989, *Molecular Cloning: A Laboratory Manual*, Second Edition, Cold Spring Harbor Press, Plainview, N.Y. Hybridization and the strength of hybridization (i.e., the strength of the association between the nucleic acids) is influenced by such factors as the degree of complementarity between the nucleic acids, stringency of the conditions involved, and the thermal melting point (Tm) of the formed hybrid. Those skilled in the art understand how to estimate and adjust the stringency of hybridization conditions such that sequences having at least a desired level of complementarity will stably hybridize, while those having lower complementarity will not. For examples of hybridization conditions and parameters, see, e.g., Sambrook, et al., 1989, *Molecular Cloning: A Laboratory Manual*, Second Edition, Cold Spring Harbor Press, Plainview, N.Y.; Ausubel, F. M. et al., 1994, *Current Protocols in Molecular Biology*, John Wiley & Sons, Secaucus, N.J. In some embodiments, specific hybridization occurs under stringent hybridization conditions. An oligonucleotide or polynucleotide (e.g., a probe or a primer) that is specific for a target nucleic acid will "hybridize" to the target nucleic acid under suitable conditions.

As used herein, "oligonucleotide" refers to a molecule that has a sequence of nucleic acid bases on a backbone comprised mainly of identical monomer units at defined intervals. The bases are arranged on the backbone in such a way that they can bind with a nucleic acid having a sequence of bases that are complementary to the bases of the oligonucleotide. The most common oligonucleotides have a backbone of sugar phosphate units. A distinction may be made between oligodeoxyribonucleotides that do not have a hydroxyl group at the 2' position and oligoribonucleotides that have a hydroxyl group at the 2' position. Oligonucleotides may also include derivatives, in which the hydrogen of the hydroxyl group is replaced with organic groups, e.g., an allyl group. One or more bases of the oligonucleotide may also be modified to include a phosphorothioate bond (e.g., one of the two oxygen atoms in the phosphate backbone which is not involved in the internucleotide bridge, is replaced by a sulfur atom) to increase resistance to nuclease degradation. The exact size of the oligonucleotide will depend on many factors, which in turn depend on the ultimate function or use of the oligonucleotide. The oligonucleotide may be generated in any manner, including, for example, chemical synthesis, DNA replication, restriction endonuclease digestion of plasmids or phage DNA, reverse transcription, PCR, or a combination thereof. The oligonucleotide may be modified e.g., by addition of a methyl group, a biotin or digoxigenin moiety, a fluorescent tag or by using radioactive nucleotides.

As used herein, the term "pharmaceutically-acceptable carrier" is intended to include any and all solvents, dispersion media, coatings, antibacterial and antifungal compounds, isotonic and absorption delaying compounds, and the like, compatible with pharmaceutical administration. Pharmaceutically-acceptable carriers and their formulations are known to one skilled in the art and are described, for example, in Remington's Pharmaceutical Sciences (20th edition, ed. A. Gennaro, 2000, Lippincott, Williams & Wilkins, Philadelphia, Pa.).

As used herein, the term "polynucleotide" or "nucleic acid" means any RNA or DNA, which may be unmodified or modified RNA or DNA. Polynucleotides include, without limitation, single- and double-stranded DNA, DNA that is a mixture of single- and double-stranded regions, single- and double-stranded RNA, RNA that is mixture of single- and double-stranded regions, and hybrid molecules comprising DNA and RNA that may be single-stranded or, more typically, double-stranded or a mixture of single- and double-stranded regions. In addition, polynucleotide refers to triple-stranded regions comprising RNA or DNA or both RNA and DNA. The term polynucleotide also includes DNAs or RNAs containing one or more modified bases and DNAs or RNAs with backbones modified for stability or for other reasons.

As used herein, "prevention," "prevent," or "preventing" of a disease or condition refers to one or more compounds that, in a statistical sample, reduces the occurrence of the disease or condition in the treated sample relative to an untreated control sample, or delays the onset of one or more symptoms of the disease or condition relative to the untreated control sample. As used herein, prevention includes preventing or delaying the initiation of symptoms of the disease or condition. As used herein, prevention also includes preventing a recurrence of one or more signs or symptoms of a disease or condition.

As used herein, the term "sample" refers to clinical samples obtained from a subject. Biological samples may include tissues, cells, protein or membrane extracts of cells, mucus, sputum, bone marrow, bronchial alveolar lavage (BAL), bronchial wash (BW), tumor biopsies, and biological fluids (e.g., ascites fluid or cerebrospinal fluid (CSF)) isolated from a subject, as well as tissues, cells and fluids (blood, plasma, saliva, urine, serum etc.) present within a subject.

As used herein, the term "separate" therapeutic use refers to an administration of at least two active ingredients at the same time or at substantially the same time by different routes.

As used herein, the term "sequential" therapeutic use refers to administration of at least two active ingredients at different times, the administration route being identical or different. More particularly, sequential use refers to the whole administration of one of the active ingredients before administration of the other or others commences. It is thus possible to administer one of the active ingredients over several minutes, hours, or days before administering the other active ingredient or ingredients. There is no simultaneous treatment in this case.

As used herein, the term "simultaneous" therapeutic use refers to the administration of at least two active ingredients by the same route and at the same time or at substantially the same time.

As used herein, the terms "subject," "individual," or "patient" are used interchangeably and refer to an individual organism, a vertebrate, a mammal, or a human. In certain embodiments, the individual, patient or subject is a human.

"Treating", "treat", or "treatment" as used herein covers the treatment of a disease or disorder described herein, in a subject, such as a human, and includes: (i) inhibiting a disease or disorder, i.e., arresting its development; (ii) relieving a disease or disorder, i.e., causing regression of the disorder; (iii) slowing progression of the disorder; and/or (iv) inhibiting, relieving, or slowing progression of one or more symptoms of the disease or disorder. In some embodiments, treatment means that the symptoms associated with the disease are, e.g., alleviated, reduced, cured, or placed in a state of remission.

It is also to be appreciated that the various modes of treatment or prevention of medical diseases and conditions as described are intended to mean "substantial," which includes total but also less than total treatment or prevention, and wherein some biologically or medically relevant result is achieved. The treatment may be a continuous prolonged treatment for a chronic disease or a single, or few time administrations for the treatment of an acute condition.

Breast Cancer

There are four main types of breast cancers: $ER^+/PR^+/HER2^-$ breast cancer ("Luminal A" breast cancer"), $ER^+/PR^+/HER2^+$ ("Luminal B" breast cancer"), $ER^-/PR^-/HER2^+$ (HER2-positive breast cancer), or $ER^-/PR^-/HER2^-$ ("Triple Negative" breast cancer (TNBC)). ER and PR refer to the receptors for the hormones estrogen and progesterone, respectively (also referred to as $HR^+$). $HR^+$ tumor cells have receptors for the hormones estrogen and progesterone, which can promote the growth of $HR^+$ tumors. HER2 stands for human epidermal growth factor receptor. $HER2^+$ tumor cells make high levels of a protein known as HER2/neu, which has been shown to be associated with certain aggressive types of breast cancer. Howlander et al. SEER Cancer Statistics Review, 1975-2016, National Cancer Institute, Bethesda, Md., 2019.

Ghrelin, Unacylated Ghrelin, and Analogs Thereof

Ghrelin is a peptide hormone produced and released mainly by the stomach, with small amounts also released by the small intestine, pancreas and brain. Ghrelin is also known as the "hunger hormone" because it stimulates appetite, increases food intake and promotes fat storage. Apart from its orexigenic effect, research in the last decade has shown that ghrelin has regulatory roles in in many organs and systems. Ghrelin signaling has increasingly been recognized as a key regulator of obesity, insulin resistance and diabetes; intriguingly, many of these regulatory functions appear to be independent of ghrelin's effect on food intake.

Ghrelin exists in two major forms: n-octanoyl-modified ghrelin ("ghrelin"), which possesses an n-octanoyl modification on serine-3, and des-acyl ghrelin or unacylated ghrelin ("UAG"). Circulating ghrelin is composed of more than 90% of desacyl ghrelin and less than 10% acyl ghrelin. Human ghrelin is biosynthecized as a 117-amino acid long ghrelin-obestatin preproprotein. The human ghrelin-obestatin preproprotein, NCBI Reference Sequence: NP 001289751.1, has the following sequence:

(SEQ ID NO: 1)
MPSPGTVCSLLLLGMLWLDLAMAGSSFLSPEHQRVQQRKESKKPPAKLQP

RALAGWLRPEDGGQAEGAEDELEVRFNAPFDVGIKLSGVQYQQHSQALGK

FLQDILWEEAKEAPADK

The ghrelin-obestatin preproprotein contains an N-terminal signal peptide and C-terminal pro-ghrelin peptides. The ghrelin-obestatin preproprotein is believed to be post-translationally cleaved by a signal peptidase at position 23, and a prohormone convertase 1/3 (PC 1/3) at Arg51. Hosoda et al., *J Biol Chem.* 278(1):64-70 (2003); Zhu et al., *J Biol Chem.* 281(50):38867-70 (2006); Delporte, *Scientifica*

(Cairo) 2013: 518909 (2013). Following the removal of the signal peptide and the C-terminal pro-ghrelin peptides, a 28-amino acid long peptide, "des-acyl ghrelin," or "unacylated ghrelin," having the following amino acid sequence is formed:

GSSFLSPEHQRVQQRKESKKPPAKLQPR (SEQ ID NO: 2)

Following cleavage, the enzyme ghrelin O-acyltransferase (GOAT) acylates the resultant peptide to form mature acylated ghrelin (a.k.a., acyl-ghrelin (AG) or ghrelin) having the following sequence:

GSS(n-octanoyl)FLSPEHQRVQQRKESKKPPAKLQPR. (SEQ ID NO: 3)

An octanoyl group (C8:0) and more rarely a decanoyl (C10:0) or decanoyl (C10:1) group are added by the GOAT. The functionally relevant endogenous receptor of ghrelin is growth hormone secretagogue receptor 1a (GHSR1a). Fatty acid modification of ghrelin is essential for ghrelin-induced growth hormone release from the pituitary gland and appetite stimulation. Bednarek et al., *J Med Chem.* 43(23):4370-6 (2000); Matsumoto et al., *Biochem Biophys Res Commun.* 287(1):142-6 (2001). Specifically, the acyl modification of Ser3 is required for binding to hGHSR1a.

The unacylated form of ghrelin (i.e., des-acyl ghrelin or unacylated ghrelin) does not bind to the cognate ghrelin receptor, GHSR1a because it lacks octanoylation. Initially, unacylated ghrelin was believed to be a by-product of ghrelin gene expression. However, recent studies have established an important role for this peptide hormone in regulating energy homeostasis, including reducing fat mass, improving insulin sensitivity and decreasing fasting glucose levels. Benso et al., *Eur J Endocrinol* 5:911-6 (2012); Zhang et al., *Endocrinology* 9:4710-6 (2008).

Figure 6A:
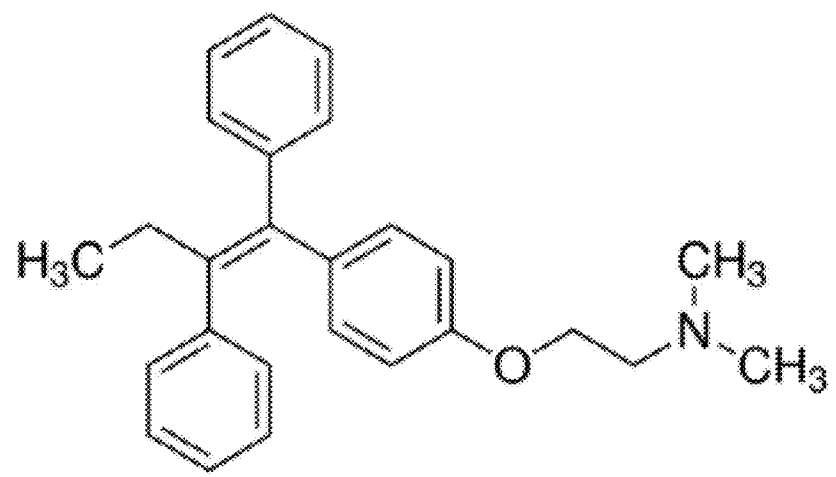
FIG. 6A shows the molecular structure of tamoxifen (adapted from Rodriguez-Antona and Ingelman-Sundberg, 2006).
Figure 6B:
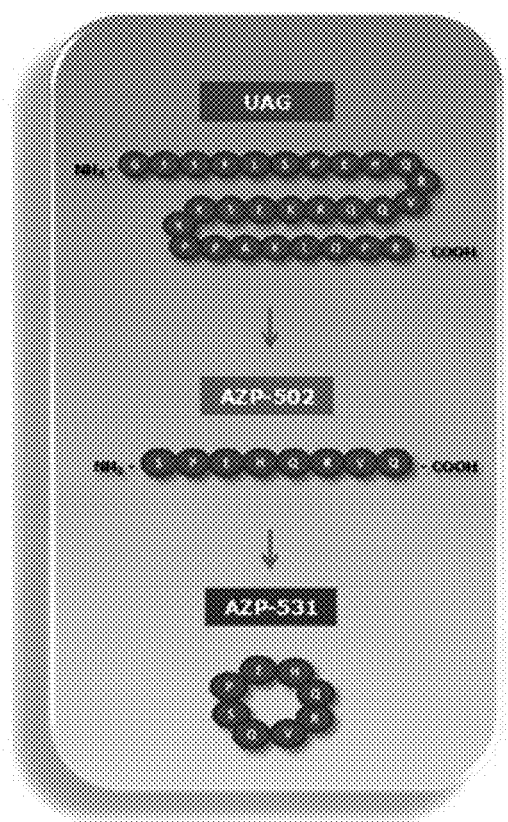
FIG. 6B shows the structure of des-acyl ghrelin and AZP531.

An unacylated ghrelin analog, AZP531 (levolitide; FIG. 6B), is a cyclic peptide that is currently in clinical trials for the treatment of Prader-Willi Syndrome and type II diabetes. Allas et al., *Diabetes Obes Metab* 9:868-74 (2016). The amino acid sequence of AZP531 is SPEHQRVQ (SEQ ID NO: 4). AZP531 has an established safety profile and better pharmacokinetic properties than unacylated ghrelin. Allas et al., *Diabetes Obes Metab* 9:868-74 (2016). The receptor for unacylated ghrelin is currently unknown and consequently, the mechanisms mediating its effects are not yet understood.

Pharmaceutical Compositions

In one aspect, the present disclosure provides pharmaceutical compositions comprising ghrelin, des-acyl ghrelin and peptide analogs thereof, including AZP531.

The pharmaceutical compositions of the present disclosure may be prepared by any of the methods known in the pharmaceutical arts. The amount of active ingredient that can be combined with a carrier material to produce a single dosage form will vary depending upon the host being treated and the particular mode of administration. The amount of active ingredient that can be combined with a carrier material to produce a single dosage form will generally be that amount of the compound that produces a therapeutic effect. Generally, the amount of active compound will be in the range of about 0.1 to 99 percent, more typically, about 5 to 70 percent, and more typically, about 10 to 30 percent.

In some embodiments, pharmaceutical compositions of the present technology may contain one or more pharmaceutically-acceptable carriers, which as used herein, generally refers to a pharmaceutically-acceptable composition, such as a liquid or solid filler, diluent, excipient, manufacturing aid (e.g., lubricant, talc magnesium, calcium or zinc stearate, or steric acid), or solvent encapsulating material, useful for introducing the active agent into the body.

Examples of suitable aqueous and non-aqueous carriers that may be employed in the pharmaceutical compositions of the present technology include, for example, water, ethanol, polyols (such as glycerol, propylene glycol, polyethylene glycol, and the like), vegetable oils (such as olive oil), and injectable organic esters (such as ethyl oleate), and suitable mixtures thereof. Proper fluidity can be maintained, for example, by the use of coating materials, such as lecithin, by the maintenance of the required particle size in the case of dispersions, and by the use of surfactants.

In some embodiments, the formulations may include one or more of sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; alginic acid; buffering agents, such as magnesium hydroxide and aluminum hydroxide; pyrogen-free water; isotonic saline; Ringer's solution; ethyl alcohol; pH buffered solutions; polyesters, polycarbonates and/or polyanhydrides; preservatives; glidants; fillers; and other non-toxic compatible substances employed in pharmaceutical formulations.

Various auxiliary agents, such as wetting agents, emulsifiers, lubricants (e.g., sodium lauryl sulfate and magnesium stearate), coloring agents, release agents, coating agents, sweetening agents, flavoring agents, preservative agents, and antioxidants can also be included in the pharmaceutical composition of the present technology. Some examples of pharmaceutically-acceptable antioxidants include: water soluble antioxidants, such as ascorbic acid, cysteine hydrochloride, sodium bisulfate, sodium metabisulfite, sodium sulfite, and the like; oil-soluble antioxidants, such as ascorbyl palmitate, butylated hydroxyanisole (BHA), butylated hydroxytoluene (BHT), lecithin, propyl gallate, alpha-tocopherol, and the like; and metal chelating agents, such as citric acid, ethylenediamine tetraacetic acid (EDTA), sorbitol, tartaric acid, phosphoric acid, and the like. In some embodiments, the pharmaceutical formulation includes an excipient selected from, for example, celluloses, liposomes, micelle-forming agents (e.g., bile acids), and polymeric carriers, e.g., polyesters and polyanhydrides. Suspensions, in addition to the active compounds, may contain suspending agents, such as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof. Prevention of the action of microorganisms on the active compounds may be ensured by the inclusion of various antibacterial and antifungal agents, such as, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents that delay absorption, such as aluminum monostearate and gelatin.

Therapeutic Methods

The following discussion is presented by way of example only, and is not intended to be limiting.

One aspect of the present technology includes methods of treating a cancer that does not comprise a mutation in BRAF, HRAS, and KRAS. Examples of such cancers include breast cancer and colorectal cancer. Additionally or alternatively, in some embodiments, the present technology includes methods of treating luminal A (ER$^+$/PR$^+$/HER2$^-$), luminal B (ER$^+$/PR$^+$/HER2$^+$), HER2-positive, TNBC (ER$^-$/PR$^-$/HER2$^-$), basal-like, and/or mesenchymal-like breast cancers. In one aspect, the present disclosure provides a method for treating cancer in a subject in need thereof, comprising administering to the subject an effective amount of ghrelin, des-acyl ghrelin, or an analog thereof, wherein the cancer does not comprise a mutation in BRAF, HRAS, and KRAS. In some embodiments, the analog is a cyclic peptide comprising the amino acid sequence SPEHQRVQ (SEQ ID NO: 4). The cancer may be resistant to tamoxifen. Additionally or alternatively, in some embodiments, the effective amount of ghrelin, des-acyl ghrelin, or the analog is about 10-100 pM.

In some embodiments, the subject is diagnosed as having, suspected as having, or at risk of having a cancer that does not comprise a mutation in BRAF, HRAS, and KRAS. Additionally or alternatively, in some embodiments, the subject is diagnosed as having or is suffering from colorectal cancer or breast cancer. The breast cancer may be ER$^+$/PR$^+$/HER2$^-$ breast cancer ("Luminal A" breast cancer"), ER$^+$/PR$^+$/HER2$^+$ ("Luminal B" breast cancer"), ER$^-$/PR$^-$/HER2$^+$ (HER2-positive breast cancer), or ER$^-$/PR$^-$/HER2$^-$ ("Triple Negative" breast cancer (TNBC)). In some embodiments, the subtype of the TNBC is basal-like or mesenchymal-like. Additionally or alternatively, in some embodiments, the subject is diagnosed as having, suspected as having, or at risk of having a cancer (e.g., breast cancer or colorectal cancer) that does not comprise a mutation in BRAF, HRAS, and KRAS. Additionally or alternatively, in some embodiments, the subject is diagnosed as having, suspected as having, or at risk of having luminal A (ER$^+$/PR$^+$/HER2$^-$), luminal B (ER$^+$/PR$^+$/HER2$^+$), HER2-positive, TNBC (ER$^-$/PR$^-$/HER2$^-$), basal-like, and/or mesenchymal-like breast cancer. In any and all embodiments of the method, the subject harbors at least one mutation in one or more genes selected from the group consisting of CDKN2A, PIK3 CA, TP53, PTEN, RB1, SMAD4, and NF1.

In therapeutic applications, compositions or medicaments comprising ghrelin, des-acyl ghrelin, or an analog thereof (e.g., the cyclic peptide analog AZP531) are administered to a subject suspected of, or already suffering from a disease or condition described herein in an amount sufficient to cure, or at least partially arrest, the symptoms of the disease, including its complications and intermediate pathological phenotypes in development of the disease.

Subjects suffering from a cancer that does not comprise a mutation in BRAF, HRAS, and KRAS (e.g., colorectal cancer or breast cancer), and/or breast cancer such as luminal A (ER$^+$/PR$^+$/HER2$^-$), luminal B (ER$^+$/PR$^+$/HER2$^+$), HER2-positive, TNBC (ER$^-$/PR$^-$/HER2$^-$), basal-like, and/or mesenchymal-like breast cancer can be identified by any or a combination of diagnostic or prognostic assays known in the art.

In some embodiments, subjects with suffering from a cancer that does not comprise a mutation in BRAF, HRAS, and KRAS (e.g., colorectal cancer or breast cancer), and/or breast cancer (such as luminal A (ER$^+$/PR$^+$/HER2$^-$), luminal B (ER$^+$/PR$^+$/HER2$^+$), HER2-positive, TNBC (ER$^-$/PR$^-$/HER2$^-$), basal-like, and/or mesenchymal-like breast cancer), that are treated with ghrelin, des-acyl ghrelin, or an analog thereof (e.g., the cyclic peptide analog AZP531) will show amelioration or elimination of one or more of the following symptoms: swelling in one or both breasts, redness or pitting of breast skin, change in breast size or shape, nipple discharge, breast pain, lumps on or inside the breast, itchy breasts, peeling or flaking of nipple skin, skin irritation or dimpling, nipple pain, nipple retraction, and lumps or swelling in underarm lymph nodes, diarrhea, constipation, narrowing of stool, rectal bleeding, dark or bloody stool, cramping, abdominal pain, fatigue, and unintended weight loss. In any and all embodiments of the therapeutic methods disclosed herein, administration of the ghrelin, des-acyl ghrelin, or analog results in reduction in tumor size, reduced metastasis, and/or partial or complete remission compared to an untreated control subject suffering from said cancer.

In one aspect, the present disclosure provides a method for monitoring the therapeutic efficacy of a pharmaceutical composition in a subject diagnosed with or suffering from cancer comprising: (a) detecting phosphorylation levels of one or more signaling proteins selected from the group consisting of ERK1/2, p90RSK, Akt, and p70S6K in a test sample obtained from the subject after the subject has been administered the pharmaceutical composition; and (b) determining that the pharmaceutical composition is effective when the phosphorylation levels of the one or more signaling proteins in the test sample are reduced compared to that observed in a control sample obtained from the subject prior to administration of the pharmaceutical composition, wherein the pharmaceutical composition comprises ghrelin, des-acyl ghrelin, or an analog thereof, and wherein the cancer does not comprise a mutation in BRAF, HRAS, and KRAS. In another aspect, the present disclosure provides a method for monitoring the therapeutic efficacy of a pharmaceutical composition in a subject diagnosed with or suffering from cancer comprising: (a) detecting expression levels of one or more genes selected from the group consisting of cMYC, CDK4/cyclin D3, pRB (Ser 795) and BCL2 in a test sample obtained from the subject after the subject has been administered the pharmaceutical composition; and (b) determining that the pharmaceutical composition is effective when the expression levels of the one or more genes in the test sample are reduced compared to that observed in a control sample obtained from the subject prior to administration of the pharmaceutical composition, wherein the pharmaceutical composition comprises ghrelin, des-acyl ghrelin, or an analog thereof, and wherein the cancer does not comprise a mutation in BRAF, HRAS, and KRAS. In some embodiments of the methods disclosed herein, the test sample is a tumor sample. Additionally or alternatively, in some embodiments, the methods of the present technology further comprise detecting levels of GTP-bound $G\alpha_i$, cell cycle arrest, and/or apoptosis in the test sample.

In yet another aspect, the present disclosure provides a method for reducing chemotherapy-induced side effects in a subject diagnosed with or suffering from cancer comprising: administering to the subject an effective amount of ghrelin, des-acyl ghrelin, or an analog thereof, and an effective amount of a chemotherapeutic agent, wherein the cancer does not comprise a mutation in BRAF, HRAS, and KRAS. Examples of chemotherapy-induced side effects include muscle cell death or cardiotoxicity. In some embodiments of the methods disclosed herein, the analog is a cyclic peptide comprising the amino acid sequence SPEHQRVQ (SEQ ID NO: 4). Additionally or alternatively, in some embodiments of the methods disclosed herein, the cancer is colorectal cancer or breast cancer. The breast cancer may be ER+/PR+/HER2− breast cancer ("Luminal A" breast cancer"), ER+/PR+/HER2+ ("Luminal B" breast cancer"), ER−/PR−/HER2+ (HER2-positive breast cancer), or ER−/PR−/HER2− ("Triple Negative" breast cancer (TNBC)). In some embodiments, the subtype of the TNBC is basal-like or mesenchymal-like. In any and all embodiments of the method, the subject harbors at least one mutation in one or more genes selected from the group consisting of CDKN2A, PIK3CA, TP53, PTEN, RB1, SMAD4, and NF1.

Prophylactic Methods

In one aspect, the present technology provides a method for preventing or delaying the onset of a cancer that does not comprise a mutation in BRAF, HRAS, and KRAS, or symptoms of a cancer that does not comprise a mutation in BRAF, HRAS, and KRAS in a subject at risk of developing a cancer that does not comprise a mutation in BRAF, HRAS, and KRAS. Examples of such cancers include breast cancer and colorectal cancer. The breast cancer may be ER+/PR+/HER2− breast cancer ("Luminal A" breast cancer"), ER+/PR+/HER2+ ("Luminal B" breast cancer"), ER−/PR−/HER2+ (HER2-positive breast cancer), or ER−/PR−/HER2− ("Triple Negative" breast cancer (TNBC)). In some embodiments, the subtype of the TNBC is basal-like or mesenchymal-like. Additionally or alternatively, in some embodiments, the subject may exhibit one or more mutations in CDKN2A, PIK3 CA, TP53, PTEN, RB1, SMAD4, and NF1.

Subjects at risk for a cancer that does not comprise a mutation in BRAF, HRAS, and KRAS (e.g., breast cancer, colorectal cancer) can be identified by, e.g., any or a combination of diagnostic or prognostic assays known in the art. For example, the subjects may exhibit at least one mutation in one or more of twelve core cellular signaling pathways and processes. Jones et al., *Science* 321(5897): 1801-1806 (2008). Alternatively, or additionally, the subjects may have a family history of such cancers and other factors increase the risk of such cancers.

In prophylactic applications, pharmaceutical compositions or medicaments comprising ghrelin, des-acyl ghrelin, or an analog thereof (e.g., the cyclic peptide analog AZP531) are administered to a subject susceptible to, or otherwise at risk for developing a disease or condition such as a cancer that does not comprise a mutation in BRAF, HRAS, and KRAS (e.g., breast cancer, colorectal cancer), in an amount sufficient to eliminate or reduce the risk, or delay the onset of the disease, including biochemical, histologic and/or behavioral symptoms of the disease, its complications and intermediate pathological phenotypes presenting during development of the disease. Administration of a prophylactic ghrelin, des-acyl ghrelin, or an analog thereof (e.g., the cyclic peptide analog AZP531) can occur prior to the manifestation of symptoms characteristic of the disease or disorder, such that the disease or disorder is prevented or, alternatively, delayed in its progression.

In some embodiments, treatment with ghrelin, des-acyl ghrelin, or an analog thereof (e.g., the cyclic peptide analog AZP531) will prevent or delay the onset of one or more of the following symptoms: swelling in one or both breasts, redness or pitting of breast skin, change in breast size or shape, nipple discharge, breast pain, lumps on or inside the breast, itchy breasts, peeling or flaking of nipple skin, skin irritation or dimpling, nipple pain, nipple retraction, and lumps or swelling in underarm lymph nodes, diarrhea, constipation, narrowing of stool, rectal bleeding, dark or bloody stool, cramping, abdominal pain, fatigue, and unintended weight loss.

For therapeutic and/or prophylactic applications, a composition comprising ghrelin, des-acyl ghrelin, or an analog thereof (e.g., the cyclic peptide analog AZP531) is administered to the subject. In some embodiments, ghrelin, des-acyl ghrelin, or an analog thereof (e.g., the cyclic peptide analog AZP531) is administered one, two, three, four, or five times per day. In some embodiments, ghrelin, des-acyl ghrelin, or an analog thereof (e.g., the cyclic peptide analog AZP531) is administered more than five times per day. Additionally or alternatively, in some embodiments, ghrelin, des-acyl ghrelin, or an analog thereof (e.g., the cyclic peptide analog AZP531) is administered every day, every other day, every third day, every fourth day, every fifth day, or every sixth day. In some embodiments, ghrelin, des-acyl ghrelin, or an analog thereof (e.g., the cyclic peptide analog AZP531) is administered weekly, bi-weekly, tri-weekly, or monthly. In some embodiments, ghrelin, des-acyl ghrelin, or an analog thereof (e.g., the cyclic peptide analog AZP531) is administered for a period of one, two, three, four, or five weeks. In some embodiments, ghrelin, des-acyl ghrelin, or an analog thereof (e.g., the cyclic peptide analog AZP531) is administered for six weeks or more. In some embodiments, ghrelin, des-acyl ghrelin, or an analog thereof (e.g., the cyclic peptide analog AZP531) is administered for twelve weeks or more. In some embodiments, ghrelin, des-acyl ghrelin, or an analog thereof (e.g., the cyclic peptide analog AZP531) is administered for a period of less than one year. In some embodiments, ghrelin, des-acyl ghrelin, or an analog thereof (e.g., the cyclic peptide analog AZP531) is administered for a period of more than one year. In some embodiments, ghrelin, des-acyl ghrelin, or an analog thereof (e.g., the cyclic peptide analog AZP531) is administered throughout the subject's life.

In some embodiments of the methods of the present technology, ghrelin, des-acyl ghrelin, or an analog thereof (e.g., the cyclic peptide analog AZP531) is administered daily for 1 week or more. In some embodiments of the methods of the present technology, ghrelin, des-acyl ghrelin, or an analog thereof (e.g., the cyclic peptide analog AZP531) is administered daily for 2 weeks or more. In some embodiments of the methods of the present technology, ghrelin, des-acyl ghrelin, or an analog thereof (e.g., the cyclic peptide analog AZP531) is administered daily for 3 weeks or more. In some embodiments of the methods of the present technology, ghrelin, des-acyl ghrelin, or an analog thereof (e.g., the cyclic peptide analog AZP531) is administered daily for 4 weeks or more. In some embodiments of the methods of the present technology, ghrelin, des-acyl ghrelin, or an analog thereof (e.g., the cyclic peptide analog AZP531) is administered daily for 6 weeks or more. In some embodiments of the methods of the present technology, ghrelin, des-acyl ghrelin, or an analog thereof (e.g., the cyclic peptide analog AZP531) is administered daily for 12 weeks or more. In some embodiments, ghrelin, des-acyl ghrelin, or an analog thereof (e.g., the cyclic peptide analog AZP531) is administered daily throughout the subject's life.

Determination of the Biological Effect of Ghrelin, Des-Acyl Ghrelin or Analogs Thereof In various embodiments, suitable in vitro or in vivo assays are performed to determine the effect of a specific ghrelin, des-acyl ghrelin, or an analog thereof (e.g., the cyclic peptide analog AZP531), and whether its administration is indicated for treatment. In various embodiments, in vitro assays can be performed with representative animal models, to determine if a given ghrelin, des-acyl ghrelin, or an analog thereof (e.g., the cyclic peptide analog AZP531) exerts the desired effect on reducing or eliminating signs and/or symptoms of cancer (e.g., breast cancer, colon cancer). Compounds for use in therapy can be tested in suitable animal model systems including, but not limited to rats, mice, chicken, cows, monkeys, rabbits, and the like, prior to testing in human subjects. Similarly, for in vivo testing, any of the animal model systems known in the art can be used prior to administration to human subjects. In some embodiments, in vitro or in vivo testing is directed to the biological function of des-acyl ghrelin, including inhibition of MAPK and Akt signaling, inhibition of cAMP formation, increased formation of GTP-bound $G\alpha_i$, cell cycle arrest and apoptosis (See Examples 3-5 described herein).

Animal models of cancer (e.g., breast cancer, colorectal cancer), may be generated using techniques known in the art (see Examples described herein). Such models may be used to demonstrate the biological effect of ghrelin, des-acyl ghrelin, or an analog thereof (e.g., the cyclic peptide analog AZP531) in the prevention and treatment of cancer, and/or inhibition of a specific pathway, and for determining what comprises a therapeutically effective amount of ghrelin, des-acyl ghrelin, or an analog thereof (e.g., the cyclic peptide analog AZP531) in a given context.

Modes of Administration and Effective Dosages

Any method known to those in the art for contacting a cell, organ or tissue with ghrelin, des-acyl ghrelin, or an analog thereof (e.g., the cyclic peptide analog AZP531) disclosed herein may be employed. Suitable methods include in vitro, ex vivo, or in vivo methods. In vivo methods typically include the administration of ghrelin, des-acyl ghrelin, or an analog thereof (e.g., the cyclic peptide analog AZP531) to a mammal, suitably a human. When used in vivo for therapy, ghrelin, des-acyl ghrelin, or an analog thereof (e.g., the cyclic peptide analog AZP531) are administered to the subject in effective amounts (i.e., amounts that have desired therapeutic effect). The dose and dosage regimen will depend upon the degree of the disease state of the subject, the characteristics of the particular agent (e.g., ghrelin, des-acyl ghrelin, or an analog thereof (e.g., the cyclic peptide analog AZP531)) used, e.g., its therapeutic index, and the subject's history.

The effective amount may be determined during pre-clinical trials and clinical trials by methods familiar to physicians and clinicians. An effective amount of ghrelin, des-acyl ghrelin, or an analog thereof (e.g., the cyclic peptide analog AZP531) useful in the methods may be administered to a mammal in need thereof by any of a number of well-known methods for administering pharmaceutical compounds. Ghrelin, des-acyl ghrelin, or an analog thereof (e.g., the cyclic peptide analog AZP531) may be administered systemically or locally.

Ghrelin, des-acyl ghrelin, or an analog thereof (e.g., the cyclic peptide analog AZP531) can be incorporated into pharmaceutical compositions for administration, singly or in combination, to a subject for the treatment or prevention of a disease or condition disclosed herein. Such compositions typically include the active agent and a pharmaceutically acceptable carrier. As used herein the term "pharmaceutically acceptable carrier" includes saline, solvents, dispersion media, coatings, antibacterial and antifungal agents, isotonic and absorption delaying agents, and the like, compatible with pharmaceutical administration. Supplementary active compounds can also be incorporated into the compositions.

Pharmaceutical compositions are typically formulated to be compatible with its intended route of administration. Examples of routes of administration include parenteral (e.g., intravenous, intradermal, intraperitoneal or subcutaneous), oral, inhalation, transdermal (topical), intraocular, ion-tophoretic, and transmucosal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfate; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic. For convenience of the patient or treating physician, the dosing formulation can be provided in a kit containing all necessary equipment (e.g., vials of drug, vials of diluent, syringes and needles) for a treatment course (e.g., 7 days of treatment).

Pharmaceutical compositions suitable for injectable use can include sterile aqueous solutions (where water soluble) or dispersions and sterile powders for the extemporaneous preparation of sterile injectable solutions or dispersion. For intravenous administration, suitable carriers include physiological saline, bacteriostatic water, CREMOPHOR ELTM (BASF, Parsippany, N.J.) or phosphate buffered saline (PBS). In all cases, a composition for parenteral administration must be sterile and should be fluid to the extent that easy syringability exists. It should be stable under the conditions of manufacture and storage and must be preserved against the contaminating action of microorganisms such as bacteria and fungi.

The pharmaceutical compositions having ghrelin, des-acyl ghrelin, or an analog thereof (e.g., the cyclic peptide analog AZP531) can include a carrier, which can be a solvent or dispersion medium containing, for example, water, ethanol, polyol (e.g., glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thiomerasol, and the like. Glutathione and other antioxidants can be included to prevent oxidation. In many cases, it will be advantageous to include isotonic agents, for example, sugars, polyalcohols such as mannitol, sorbitol, or sodium chloride in the composition. Prolonged absorption of the injectable compositions can be brought about by including in the composition an agent that delays absorption, for example, aluminum monostearate or gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle, which contains a basic dispersion medium and the required other ingredients from those enumerated above. In the case of sterile powders for the preparation of sterile injectable solutions, typical methods of preparation include vacuum drying and freeze drying, which can yield a powder of the active ingredient plus any additional desired ingredient from a previously sterile-filtered solution thereof.

Oral compositions generally include an inert diluent or an edible carrier. For the purpose of oral therapeutic administration, the active compound can be incorporated with excipients and used in the form of tablets, troches or capsules, e.g., gelatin capsules. Oral compositions can also be prepared using a fluid carrier for use as a mouthwash. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds can be delivered in the form of an aerosol spray from a pressurized container or dispenser, which contains a suitable propellant, e.g., a gas such as carbon dioxide, or a nebulizer. Such methods include those described in U.S. Pat. No. 6,468,798.

Systemic administration of a therapeutic compound as described herein can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays. For transdermal administration, the active compounds are formulated into ointments, salves, gels, or creams as generally known in the art. In one embodiment, transdermal administration may be performed by iontophoresis.

A therapeutic agent can be formulated in a carrier system. The carrier can be a colloidal system. The colloidal system can be a liposome, a phospholipid bilayer vehicle. In one embodiment, the therapeutic agent is encapsulated in a liposome while maintaining the agent's structural integrity. One skilled in the art would appreciate that there are a variety of methods to prepare liposomes. (See Lichtenberg, et al., *Methods Biochem. Anal.*, 33:337-462 (1988); Anselem, et al., *Liposome Technology*, CRC Press (1993)). Liposomal formulations can delay clearance and increase cellular uptake (See Reddy, *Ann. Pharmacother.*, 34(7-8): 915-923 (2000)). An active agent can also be loaded into a particle prepared from pharmaceutically acceptable ingredients including, but not limited to, soluble, insoluble, permeable, impermeable, biodegradable or gastroretentive polymers or liposomes. Such particles include, but are not limited to, nanoparticles, biodegradable nanoparticles, microparticles, biodegradable microparticles, nanospheres, biodegradable nanospheres, microspheres, biodegradable microspheres, capsules, emulsions, liposomes, micelles and viral vector systems.

The carrier can also be a polymer, e.g., a biodegradable, biocompatible polymer matrix. In one embodiment, the therapeutic agent can be embedded in the polymer matrix, while maintaining the agent's structural integrity. The polymer may be natural, such as polypeptides, proteins or polysaccharides, or synthetic, such as poly α-hydroxy acids. Examples include carriers made of, e.g., collagen, fibronectin, elastin, cellulose acetate, cellulose nitrate, polysaccharide, fibrin, gelatin, and combinations thereof. In one embodiment, the polymer is poly-lactic acid (PLA) or copoly lactic/glycolic acid (PGLA). The polymeric matrices can be prepared and isolated in a variety of forms and sizes, including microspheres and nanospheres. Polymer formulations can lead to prolonged duration of therapeutic effect. (See Reddy, *Ann. Pharmacother.*, 34(7-8):915-923 (2000)). A polymer formulation for human growth hormone (hGH) has been used in clinical trials. (See Kozarich and Rich, *Chemical Biology*, 2:548-552 (1998)).

Examples of polymer microsphere sustained release formulations are described in PCT publication WO 99/15154 (Tracy, et al.), U.S. Pat. Nos. 5,674,534 and 5,716,644 (both to Zale, et al.), PCT publication WO 96/40073 (Zale, et al.), and PCT publication WO 00/38651 (Shah, et al.). U.S. Pat. Nos. 5,674,534 and 5,716,644 and PCT publication WO 96/40073 describe a polymeric matrix containing particles of erythropoietin that are stabilized against aggregation with a salt.

In some embodiments, the therapeutic compounds are prepared with carriers that will protect the therapeutic compounds against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Such formulations can be prepared using known techniques. The materials can also be obtained commercially, e.g., from Alza Corporation and Nova Pharmaceuticals, Inc. Liposomal suspensions (including liposomes targeted to specific cells with monoclonal antibodies to cell-specific antigens) can also be used as pharmaceutically acceptable carriers. These can be prepared according to methods known to those skilled in the art, for example, as described in U.S. Pat. No. 4,522,811.

The therapeutic compounds can also be formulated to enhance intracellular delivery. For example, liposomal delivery systems are known in the art, see, e.g., Chonn and Cullis, "Recent Advances in Liposome Drug Delivery Systems," *Current Opinion in Biotechnology* 6:698-708 (1995); Weiner, "Liposomes for Protein Delivery: Selecting Manufacture and Development Processes," *Immunomethods*, 4(3): 201-9 (1994); and Gregoriadis, "Engineering Liposomes for Drug Delivery: Progress and Problems," *Trends Biotechnol.*, 13(12):527-37 (1995). Mizguchi, et al., *Cancer Lett.*, 100: 63-69 (1996), describes the use of fusogenic liposomes to deliver a protein to cells both in vivo and in vitro.

Dosage, toxicity and therapeutic efficacy of any therapeutic agent can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds that exhibit high therapeutic indices are advantageous. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds may be within a range of circulating concentrations that include the ED50 with little or no toxicity. The dosage may vary within this range depending upon the dosage form employed and the route of administration utilized. For any compound used in the methods, the therapeutically effective dose can be estimated initially from cell culture assays. A dose can be formulated in animal models to achieve a circulating plasma concentration range that includes the IC50 (i.e., the concentration of the test compound which achieves a half-maximal inhibition of symptoms) as determined in cell culture. Such information can be used to determine useful doses in humans accurately. Levels in plasma may be measured, for example, by high performance liquid chromatography.

Typically, an effective amount of ghrelin, des-acyl ghrelin, or an analog thereof (e.g., the cyclic peptide analog AZP531) sufficient for achieving a therapeutic or prophylactic effect, range from about 0.000001 mg per kilogram body weight per day to about 10,000 mg per kilogram body weight per day. Suitably, the dosage ranges are from about 0.0001 mg per kilogram body weight per day to about 100 mg per kilogram body weight per day. For example, dosages can be 1 mg/kg body weight or 10 mg/kg body weight every day, every two days or every three days or within the range of 1-10 mg/kg every week, every two weeks or every three weeks. In one embodiment, a single dosage of the therapeutic compound ranges from 0.001-10,000 micrograms per kg body weight. In one embodiment, concentrations of ghrelin, des-acyl ghrelin, or an analog thereof (e.g., the cyclic peptide analog AZP531) in a carrier range from 0.2 to 2000 micrograms per delivered milliliter. An exemplary treatment regime entails administration once per day or once a week. In therapeutic applications, a relatively high dosage at relatively short intervals is sometimes required until progression of the disease is reduced or terminated, or until the subject shows partial or complete amelioration of symptoms of disease. Thereafter, the patient can be administered a prophylactic regime.

In some embodiments, a therapeutically effective amount of a ghrelin, des-acyl ghrelin, or an analog thereof (e.g., the cyclic peptide analog AZP531) may be defined as a concentration of the agent at the target tissue of $10^{-32}$ to $10'$ molar, e.g., approximately $10'$ molar. This concentration may be delivered by systemic doses of 0.001 to 100 mg/kg or equivalent dose by body surface area. The schedule of doses would be optimized to maintain the therapeutic concentration at the target tissue, such as by single daily or weekly administration, but also including continuous administration (e.g., parenteral infusion or transdermal application).

The skilled artisan will appreciate that certain factors may influence the dosage and timing required to effectively treat a subject, including but not limited to, the severity of the disease or disorder, previous treatments, the general health and/or age of the subject, and other diseases present. Moreover, treatment of a subject with a therapeutically effective amount of the therapeutic compositions described herein can include a single treatment or a series of treatments.

The mammal treated in accordance with the present methods can be any mammal, including, for example, farm animals, such as sheep, pigs, cows, and horses; pet animals, such as dogs and cats; laboratory animals, such as rats, mice and rabbits. In some embodiments, the mammal is a human.

Combination Therapy

In some embodiments, one or more of ghrelin, des-acyl ghrelin, or an analog thereof (e.g., the cyclic peptide analog AZP531) may be combined with one or more additional therapies for the prevention or treatment of cancer (e.g., breast cancer, colorectal cancer). In some embodiments, the cancer (e.g., breast cancer, colon cancer) does not comprise a mutation in the BRAF and/or KRAS genes.

Additional therapeutic agents include, but are not limited to, selective ER modulators (SERMs), selective estrogen receptor down-regulators (SERDs), aromatase inhibitors (AIs), chemotherapeutic agents, surgery, radiation, or any combination thereof. In some embodiments, ghrelin, des-acyl ghrelin, or an analog thereof (e.g., the cyclic peptide analog AZP531) may be separately, sequentially or simultaneously administered with at least one additional therapeutic agent selected from the group consisting of anthracyclines (such as doxorubicin, pegylated liposomal doxorubicin, and epirubicin), taxanes (such as paclitaxel, docetaxel, and albumin-bound paclitaxel), 5-fluorouracil (5-FU), Cyclophosphamide, Carboplatin, cisplatin, vinorelbine, capecitabine, Gemcitabine, Ixabepilone, Eribulin, Irinotecan, Oxaliplatin, Trifluridine, tipiracil, Tamoxifen, Fulvestrant (ICI 164384), exemestane, anastrozole, and letrozole.

Additionally or alternatively, in some embodiments, ghrelin, des-acyl ghrelin, or an analog thereof (e.g., the cyclic peptide analog AZP531) may be separately, sequentially or simultaneously administered with at least one additional therapeutic agent selected from the group consisting of alkylating agents, topoisomerase inhibitors, endoplasmic reticulum stress inducing agents, antimetabolites, mitotic inhibitors, nitrogen mustards, nitrosoureas, alkylsulfonates, platinum agents, taxanes, vinca agents, anti-estrogen drugs, aromatase inhibitors, ovarian suppression agents, VEGF/VEGFR inhibitors, EGF/EGFR inhibitors, PARP inhibitors, cytostatic alkaloids, cytotoxic antibiotics, antimetabolites, endocrine/hormonal agents, bisphosphonate therapy agents, phenphormin and targeted biological therapy agents (e.g., therapeutic peptides described in U.S. Pat. No. 6,306,832, WO 2012007137, WO 2005000889, WO 2010096603 etc.). In some embodiments, the at least one additional therapeutic agent is a chemotherapeutic agent.

Specific chemotherapeutic agents include, but are not limited to, cyclophosphamide, fluorouracil (or 5-fluorouracil or 5-FU), methotrexate, edatrexate (10-ethyl-10-deaza-aminopterin), thiotepa, carboplatin, cisplatin, taxanes, paclitaxel, protein-bound paclitaxel, docetaxel, vinorelbine, tamoxifen, raloxifene, toremifene, fulvestrant, gemcitabine, irinotecan, ixabepilone, temozolmide, topotecan, vincristine, vinblastine, eribulin, mutamycin, capecitabine, anastrozole, exemestane, letrozole, leuprolide, abarelix, buserlin, goserelin, megestrol acetate, risedronate, pamidronate, ibandronate, alendronate, denosumab, zoledronate, trastuzumab, tykerb, anthracyclines (e.g., daunorubicin and doxorubicin), cladribine, midostaurin, bevacizumab, oxaliplatin, melphalan, etoposide, mechlorethamine, bleomycin, microtubule poisons, annonaceous acetogenins, chlorambucil, ifosfamide, streptozocin, carmustine, lomustine, busulfan, dacarbazine, temozolomide, altretamine, 6-mercaptopurine (6-MP), cytarabine, floxuridine, fludarabine, hydroxyurea, pemetrexed, epirubicin, idarubicin, SN-38, ARC, NPC, campothecin, 9-nitrocamptothecin, 9-aminocamptothecin, rubifen, gimatecan, diflomotecan, BN80927, DX-8951f, MAG-CPT, amsacnne, etoposide phosphate, teniposide, azacitidine (Vidaza), decitabine, accatin III, 10-deacetyltaxol, 7-xylosyl-10-deacetyltaxol, cephalomannine, 10-deacetyl-7-epitaxol, 7-epitaxol, 10-deacetylbaccatin III, 10-deacetyl cephalomannine, streptozotocin, nimustine, ranimustine, bendamustine, uramustine, estramustine, mannosulfan, camptothecin, exatecan, lurtotecan, lamellarin D9-aminocamptothecin, amsacrine, ellipticines, aurintricarboxylic acid, HU-331, or combinations thereof.

Examples of antimetabolites include 5-fluorouracil (5-FU), 6-mercaptopurine (6-MP), capecitabine, cytarabine, floxuridine, fludarabine, gemcitabine, hydroxyurea, methotrexate, pemetrexed, and mixtures thereof.

Examples of taxanes include accatin III, 10-deacetyltaxol, 7-xylosyl-10-deacetyltaxol, cephalomannine, 10-deacetyl-7-epitaxol, 7-epitaxol, 10-deacetylbaccatin III, 10-deacetyl cephalomannine, and mixtures thereof.

Examples of DNA alkylating agents include cyclophosphamide, chlorambucil, melphalan, bendamustine, uramustine, estramustine, carmustine, lomustine, nimustine, ranimustine, streptozotocin; busulfan, mannosulfan, and mixtures thereof.

Examples of topoisomerase I inhibitor include SN-38, ARC, NPC, camptothecin, topotecan, 9-nitrocamptothecin, exatecan, lurtotecan, lamellarin D9-aminocamptothecin, rubifen, gimatecan, diflomotecan, BN80927, DX-8951f, MAG-CPT, and mixtures thereof. Examples of topoisomerase II inhibitors include amsacrine, etoposide, etoposide phosphate, teniposide, daunorubicin, mitoxantrone, amsacrine, ellipticines, aurintricarboxylic acid, doxorubicin, and HU-331 and combinations thereof.

In any case, the multiple therapeutic agents may be administered in any order or even simultaneously. If simultaneously, the multiple therapeutic agents may be provided in a single, unified form, or in multiple forms (by way of example only, either as a single pill or as two separate pills). One of the therapeutic agents may be given in multiple doses, or both may be given as multiple doses. If not simultaneous, the timing between the multiple doses may vary from more than zero weeks to less than four weeks. In addition, the combination methods, compositions and formulations are not to be limited to the use of only two agents.

Kits

The present disclosure also provides kits comprising ghrelin, des-acyl ghrelin, or an analog thereof (e.g., the cyclic peptide analog AZP531) and instructions for using the same to prevent and/or treat cancer (e.g., breast cancer, colon cancer). In some embodiments, the cancer (e.g., breast cancer, colon cancer) does not comprise a mutation in the BRAF, HRAS and KRAS genes. Additionally or alternatively, in some embodiments, the breast cancer is $ER^+/PR^+/HER2^-$ luminal breast cancer, $ER^+/PR^+/HER2^+$ luminal breast cancer, $ER^-/PR^-/HER2^+$, or $ER^-/PR^-/HER2^-$ "Triple Negative" breast cancer (TNBC). Optionally, the above described components of the kits of the present technology are packed in suitable containers and labeled for the prevention and/or treatment of a cancer (e.g., breast cancer, colon cancer).

The above-mentioned components may be stored in unit or multi-dose containers, for example, sealed ampoules, vials, bottles, syringes, and test tubes, as an aqueous, preferably sterile, solution or as a lyophilized, preferably sterile, formulation for reconstitution. The kit may further comprise a second container which holds a diluent suitable for diluting the pharmaceutical composition towards a higher volume. Suitable diluents include, but are not limited to, the pharmaceutically acceptable excipient of the pharmaceutical composition and a saline solution. Furthermore, the kit may comprise instructions for diluting the pharmaceutical composition and/or instructions for administering the pharmaceutical composition, whether diluted or not. The containers may be formed from a variety of materials such as glass or plastic and may have a sterile access port (for example, the container may be an intravenous solution bag or a vial having a stopper which may be pierced by a hypodermic injection needle). The kit may further comprise more containers comprising a pharmaceutically acceptable buffer, such as phosphate-buffered saline, Ringer's solution and dextrose solution. It may further include other materials desirable from a commercial and user standpoint, including other buffers, diluents, filters, needles, syringes, culture medium for one or more of the suitable hosts. The kits may optionally include instructions customarily included in commercial packages of therapeutic products, that contain information about, for example, the indications, usage, dosage, manufacture, administration, contraindications and/or warnings concerning the use of such therapeutic products.

The kit can also comprise, e.g., a buffering agent, a preservative or a stabilizing agent. The kit can also contain a control sample or a series of control samples, which can be assayed and compared to the test sample. Each component of the kit can be enclosed within an individual container and all of the various containers can be within a single package, along with instructions for interpreting the results of the assays performed using the kit. The kits of the present technology may contain a written product on or in the kit container. The written product describes how to use the reagents contained in the kit. In certain embodiments, the use of the reagents can be according to the methods of the present technology.

EXAMPLES

The present technology is further illustrated by the following Examples, which should not be construed as limiting in any way. The examples herein are provided to illustrate advantages of the present technology and to further assist a person of ordinary skill in the art with preparing or using the compositions and systems of the present technology. The examples should in no way be construed as limiting the scope of the present technology, as defined by the appended claims. The examples can include or incorporate any of the variations, aspects, or embodiments of the present technology described above. The variations, aspects, or embodiments described above may also further each include or incorporate the variations of any or all other variations, aspects or embodiments of the present technology. The following Examples demonstrate the preparation, characterization, and use of illustrative compositions of the present technology, which comprise unacetylated ghrelin or analogs thereof (such as the cyclic unacetylated ghrelin analog AZP531).

Example 1: Experimental Materials and Methods

Human BC Tissues and Preclinical Patient Derived Xenograft Models. Patient-derived breast tumors (PDX, (Zhang, et al., *Cancer Res* 15:4885-97 (2013)) and estrogen receptor positive ($ER^+$) breast tumors were used under IRB-approved protocols (WCM 1410015560 and 1603017108). All patients provided written informed consent. Cells were isolated and maintained in DMEM, supplemented with 10% fetal calf serum (FCS), 100U/ml penicillin/streptomycin and 1% sodium pyruvate (ThermoFisher Scientific). Cells were grown at 37° C. in a humidified atmosphere with 5% CO2. See Method Details for cell growth and proliferation work specific procedures.

Human BC Cells. Human breast cancer cell lines, MCF7, T47D, ZR75, MDA-MB-231, MDA-MB-468, SKBR3, Hs578T and HEK293T, DU4475 and MDA-MB-157 were purchased from ATCC, USA. Human 4-OH tamoxifen resistant breast cancer cells (LCC2), RKO, RKO-T29, RKO-A19, HCT116, HCT116-HWT, HCT116-HMUT were cultured using methods were performed as described previously (Yun et al., *Science* 325(5947):1555-9 (2009)). MCF7, MDA-MB-231, MDA-MB-468, MDA-MB-157, Hs578T, HEK293T were grown in DMEM (Invitrogen), supplemented with 10% fetal calf serum (FCS) (Invitrogen), 100U/ml penicillin/streptomycin and 1% sodium pyruvate. ZR75, T47D, SKBR3 and DU4475 were grown in RPMI, supplemented with 10% FCS, 100 U/ml penicillin/streptomycin and 2 mM L-Glutamine (ThermoFisher Scientific). LCC2 were grown in phenol red-free DMEM, supplemented with 10% charcoal stripped serum (CCS; ThermoFisher Scientific), 100 U/ml penicillin/streptomycin and 1% sodium pyruvate. All cell lines were grown at 37° C. with 5% $CO_2$ in a humidified environment. *Mycoplasma* detection of all cell lines were tested and negative results were observed.

Animal Experimental Model. All animal experiments were performed in Monash Animal Research Platform at Hudson Institute for Medical Research and Research Animal Resource Center at Weill Cornell Medicine. Experimental procedures were in accordance with guidelines for Animal Care and Use, approved by Monash University Animal Ethics Committee (MMCA2014/20) and Weill Cornell Medicine IACUC Protocol (REQ00016929). Athymic Balb/c nude, FVB/N (Animal Resources Centre, Australia) and NSG (NOD Scid gamma; NOD.CgPrkdcscidIl-2rgtmlwjl/SzJ) mice (The Jackson laboratory and Monash Breeding Colony platform) were used for this study. All mouse procedures were performed with 6-8 weeks old female mice and treatments administered via subcutaneous injection. See additional details included herein for specific in vivo experimental procedures.

Cell Growth and Proliferation Assays. 3D culture of a panel of breast cancer and colon cancer cells were seeded at a density of 3,000 cells per well in media containing 30% growth-factor-reduced matrigel or 5 mg/ml Collagen in optical-bottom 96-well plates. Patient-derived breast tumors were first dissociated into single cell suspensions and seeded at a density of 32,000 cells per well in media containing 30% matrigel. Cells were serum-starved overnight and cultured under different experimental conditions (10-1000 pM unacylated ghrelin, 100 pM ghrelin, $1.5\times10^{-13}$-$1.5\times10^{-6}$M doxorubicin, $1\times10^{18}$-$1\times10^{-7}$M AZP531, 20-200 ng/ml pertussis toxin, 10 µM U0126 (MEK inhibitor), 10 µM LY294002 (PI3K inhibitor), 0.05-5 µM MK2206 (a highly selective inhibitor of pan-Akt), 0.1-10 µM BKM120 (a pan-class I PI3K inhibitor), 60 nM KT5720, 1.4 µM SQ22536, 15 µM cAMPs-RP, 10 nM melatonin and the combination of doxorubicin/unacylated ghrelin or doxorubicin/AZP531, with or without 10 nM estradiol or 10% serum or 10 µM forskolin) and medium was replaced every 2 days. At the end of the experimental time point, cells were fixed in 100% methanol. The total number of cells, or the number of dead or proliferating cells was assessed using Hoechst, EarlyTox Dead Assay Kit (Molecular Devices), or Click-IT EdU Kit (ThermoFisher Scientific), respectively, and analyzed according to the manufacturer's protocols. Cells were then imaged with >95% well coverage (magnification of 10× with 3×3 tiled images) per field using confocal microscopy. The number of nuclei/Ethidium Homodimer-III+/EdU+ cells were counted using Imaris software (Bitplane).

Binding Assays. Cy3-tagged UAG (Pepmic Co, LtD) binding assays were performed in 3D cultures of breast cancer cells. MCF7, MDA-MB-469 and MDA-MB231 cells were seeded at a density of 3,000 cells per well in Matrigel in optical-bottom 96-well plates. Cells were serum-starved overnight. Hoechst nuclear stain was added prior to the live cell imaging. 1 µM Cy3-tagged UAG with 10% serum was then added and time-lapse confocal imaging was performed to examine the localization of peptide binding.

BRAF Transient Transfections. Two million cells were harvested and transfected with or without 1.5 µg of BRAFV600E plasmid using AMAXA Nucleofector (Lonza), according to supplier's instructions. Transfected cells were then cultured according to above sections (cell growth and proliferation assay). After 5 days, cell number per field was assessed using Hoechst nuclear stain, confocal microscopy and Image J.

GNA1 CRISPR KO Generation. The lentiviral construct, lentiCRISPRv2 (containing hSpCas9 and the chimeric guide RNA cassettes; Addgene), was digested using BsmBI. Prior to ligation, each pair of oligos (100 µM) were annealed. The oligos (GNAT sequence guide strands) designed were based on the target site sequence (20 bp) and were flanked on the 3' end by a 3 bp NGG PAM sequence. The gel-purified, BsmBI digested plasmid was ligated to the diluted (1:200) annealed oligo. The ligation product was transformed into competent *Escherichia coli* Stb13™ cells. Ampicillin resistance colonies were selected for miniprep/maxiprep (Promega).

For virus production, HEK293T cells were plated in a 10 cm dish and transfected 24 hours later (80% confluence) with a prepared mix in DMEM media (no supplements) containing 5 µg of empty vector or gRNA plasmid of GNAI1, GNAI2 or GNAI3, 2.5 µg of psPAX2, 1.25 µg of VSV.G, and 15 µl of polyethylenimine (PEI; 1 µg/ml). 24 hrs following transfection, media was replaced and supernatants (GNAI1, GNAI2 or GNAI3) were harvested and collected every 24 hrs up to 72 hrs post transfection.

To generate CRISPR/Cas9 sgRNA stable breast cancer cell lines, breast cancer cells were plated in a 6-well plate. 24 hrs following plating, cells were transfected with CRISPR/Cas9 sgRNA lentiviral vector and 8 µg/ml of polybrene. 24 hrs after transfection, media was replaced. Cells were then selected in puromycin (2 µg/ml) for 5 days. CRISPR/Cas9 sgRNA stable breast cancer cell lines were then transduced with viral supernatants (GNAI1, GNAI2 or GNAI3 virus) in the presence of polybrene (8 µg/ml). 24 hrs after transduction cells were selected in Blasticidin S (2 µg/ml) for 5 days. Selected cells were used to perform cell growth assays.

ERK and AKT Activity Assays.

ERK Activity Assay: The EKAR FRET-based system was used to monitor ERK activity. Briefly, breast cancer cells were co-transfected with pPBJ-puro-FRET3-EKAR-nls and the pCMV-hyPBase transposase vector, and stably transfected cells selected using FACS for EYFP and ECFP-positive cells. Cells were then cultured in 3D and serum-starved overnight. Prior live cell time-lapse confocal imaging, medium was replaced with 100 pM unacylated ghrelin and 10% serum. Images were acquired following FRET and analyzed using Imaris software. Data normalized to ECFP signal.

AKT Activity Assay: pMSCV-puro-Foxo3a-H212R-N400-mCherry was transfected into breast cancer cells using Amaxa Nucleofector. After 3 days of puromycin (2 µg/ml) selection, transfected cells were cultured in 3D. Cells were serum-starved overnight. Prior to live cell imaging, medium was replaced with 100 pM unacylated ghrelin and 10% serum. Time-lapse imaging was performed to examine mCherry-tagged FoxO3 localization. Data were analyzed using Hoechst nuclear stain to mask nuclei using Imaris software.

cAMP Assay. The Lance Ultra cAMP kit (Perkin Elmer) was used to measure the effect of unacylated ghrelin on cAMP production. All kit components were prepared according to manufacturer's specifications. Briefly, MCF7

(475 cells/well) were incubated at room temperature for 60 min with unacylated ghrelin (10-1000 pM), in the absence or presence of forskolin (0.5 µM). The Eu-cAMP tracer and Ulight-anti cAMP reagents were then added for 1 hour at room temperature. The plate was then read using the Envision TRF capable reader (Perkin Elmer) and fluorescence was measured with excitation wavelengths of 340 or 340 nm and emission of 665 nm according to the manufacturer's instructions.

Intracellular Calcium Release Assay. Intracellular $Ca^{2+}$ levels were measured in MCF7, ZR75 and J110 cells by fluorescence using the Flexstation (Molecular Devices, Sunnyvale, Calif., USA) as previously described (32). Briefly, cells were plated, allowed to reach 50-70% confluency, and loaded with 2 µM Fura-2-acetoxymethyl ester (fura 2-AM) for 1 hr in the presence of 2.5 mM probenecid and 0.01% pluronic F-127 at 37° C. Cells were then washed twice with assay buffer, and changes in fluorescence in response to drug addition were measured over 100 s using excitation wavelengths of 340 and 380 nm and emission of 520 nm.

$G\alpha_i$ Activation Assay. $G\alpha_i$ activation assay (NewEast Biosciences) was performed on MCF7 cells according to the manufacturer's protocol. Briefly, cell lysates from 3D cell culture were incubated with an anti-active $G\alpha_i$ antibody (1:1000). The precipitated active $G\alpha_i$ was immunoblotted with an anti-$G\alpha_i$ antibody (1:1000). Bound antibodies were revealed with HRP conjugated secondary antibodies (1:2000) using SuperSignal West pico chemiluminescent solution (Pierce, Rockford, Ill.). Protein amount was normalized to β-tubulin (using a 1:10,000 dilution of the anti-β-tubulin antibody). Membranes were scanned and the densitometric analysis of the bands was performed using the ChemiDoc MP imaging system (BioRad).

Western Blot Analysis. Western blotting was performed as described previously (Brown et al., Cancer Research 69: 5392-5399 (2009)). Briefly, cells isolated from or 5 mg/ml Collagen were lysed in RIPA lysis buffer (Sigma-Aldrich) supplemented with 100× Protease/Phosphatase inhibitor cocktail (Cell Signaling Technology Inc). Cell extracts (20 µg per lane) were separated by NuPAGE™ 4-12% Bis-Tris protein gels (ThermoFisher Scientific) and transferred to nitrocellulose membranes. Antibodies details are provided in FIG. 14. Bound antibodies were revealed with HRP conjugated secondary antibodies (1.5:10000). β-actin was used as a loading control. Membranes were scanned using the western lightning plus-ECL (Thermo Fisher Scientific). Signal intensities were quantified using ImageLab software.

Fluorescence Activated Cell Sorting (FACS). FACS analysis was performed to characterize effects of unacylated ghrelin on cell cycle and apoptosis. Cells were plated at a density of 500,000 cells in a 10 cm² petri dish. Cells were serum-starved overnight with phenol red-free media and treated with different concentrations (0-100 pM) of unacylated ghrelin, with or without 10 nM estradiol. In order to determine effects on cell cycle, cells were treated for 5 days, with media being changed every 2 days. After 5 days, cells were harvested and fixed with ice cold 70% ethanol, stored overnight at −20° C., and stained with propidium iodine (PI) staining buffer (1 mg/ml RNase A, 0.1% Triton X-100, 100 µg/ml PI in PBS). To evaluate effects on cell apoptosis, cells were treated for 6 hours, harvested and then stained with Annexin V-FITC for 15 min at room temperature in PBS. Cells were analysed with a FACSCANTO II flow cytometer (BD Biosciences, USA). For FACS data analysis by FlowJo software, forward scatter (FS) vs. side scatter (SS) plots were used for gating cells and to identify any changes in the scatter properties of the cells. Annexin V FITC-A vs Propidium Iodide-A plots from the gated cells show the populations corresponding to viable and non-apoptotic (Annexin V−PI−), early (Annexin V+PI−), and late (Annexin V+PI+) apoptotic cells.

Analysis of Cell Cycle Progression Using the Fluorescence Ubiquitination Cell Cycle Indicator (FUCCI). To investigate cell cycle progression and division in live cells, the fluorescent ubiquitination-based cell cycle indicator (FUCCI) was used to track the G1/G0 phase and S/G2/M phases. Breast cancer cells (15×10⁴ cells/well) in 6 wells plate were seeded in 2D and transduced with the Premo FUCCI Cell Cycle Sensor according to the manufacturer's protocol. After optimal expression of the FUCCI sensor was achieved (16 hr), cells were detached by TrypLE Express (Thermo Fisher Scientific), counted using a hemocytometer and seeded in media containing 30% matrigel. Cells were serum-starved overnight, treated with 100 pM unacylated ghrelin for 5 days with 10% serum and medium was replaced every 2 days. At endpoint, fluorescence was analyzed using confocal microscopy and cell counts obtained. Data are presented as a percentage of the total number of fluorescent cells examined.

Xenograft and Allograft Studies. One million MCF7 or ZR75 cells were injected into the mammary fat pad of 6-week old female athymic Balb/c nude (immunodeficient) mice. Estrogen pellets were prepared in the laboratory using 17β-estradiol (estrogen) powder and silicone according to previous publications (Laidlaw et al., Endocrinology. 136 (1):164-71 (1995)) and were implanted (0.8 mg/pellet, 60-day release) subcutaneously between the shoulder blades at the time of ER+ breast cancer cell injection. After injection, the mice were monitored daily for well-being, pain and distress, and for tumor growth by palpation. Tumors typically appeared within 14 days, with an engraftment rate of approximately 75%. Once palpable, the tumors were measured daily in the long (L) and short (W) axes with digital callipers, and tumor volume estimated using the standard formula $(L \times W^2)/2$. Once the tumor reached a volume of 200 mm³, the animal was randomized to receive saline (vehicle control) or unacylated ghrelin) via subcutaneous injection for a maximum of 28 days or until tumor size reached 10 mm in any axis, at which point the mice were humanely sacrificed by cervical dislocation.

A syngeneic breast cancer mouse model was created in female FVB/N mice. 1.25×10⁵ J110 cells were injected into the mammary fat pad of 6-week old FVB (Immunocompetent) mice. Once the tumor reached a volume of 70 mm³, the mice were randomized to receive saline (vehicle control) or treatment (unacylated ghrelin or AZP531) via subcutaneous injection. After 7 days of treatment, the mice were humanely sacrificed by cervical dislocation.

Additional studies were also performed in NSG mice. MDA-MB-468 (1×10⁶) were injected into the mammary fat pad of 6-week old NSG (immunodeficient) mice. Once the tumor reached a volume of 150 mm³, the mice were randomized to receive saline (vehicle control) or AZP531 via subcutaneous injection. After 28 days of treatment, the mice were humanely sacrificed by cervical dislocation.

Measurement of Apoptotic Cells from Xenograft/Allograft Studies. MCF7, ZR75 and J110 tumor sections post treatment with 100 µg/kg or 200 µg/kg of unacylated ghrelin were assessed using Hoechst nuclear stain and confocal microscopy. Quantification of cells with apoptotic nuclei was performed using Image J.

Figure 20:
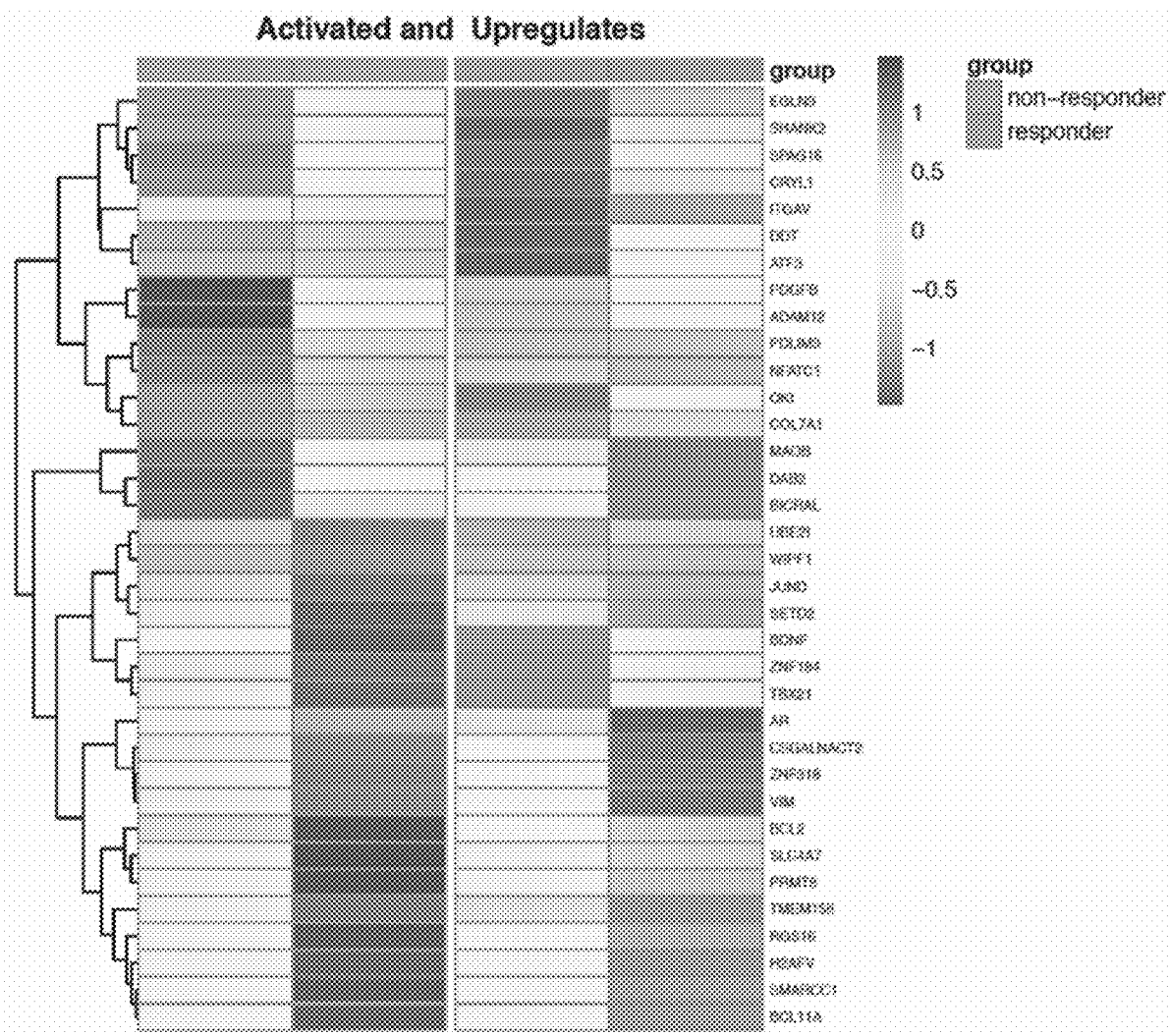
FIG. 20 show the expression pattern of MAPK-target genes in responder and non-responder TNBC patient-derived breast cancer cases. Red and blue colors indicate high and low gene expression, respectively.
Figure 20:
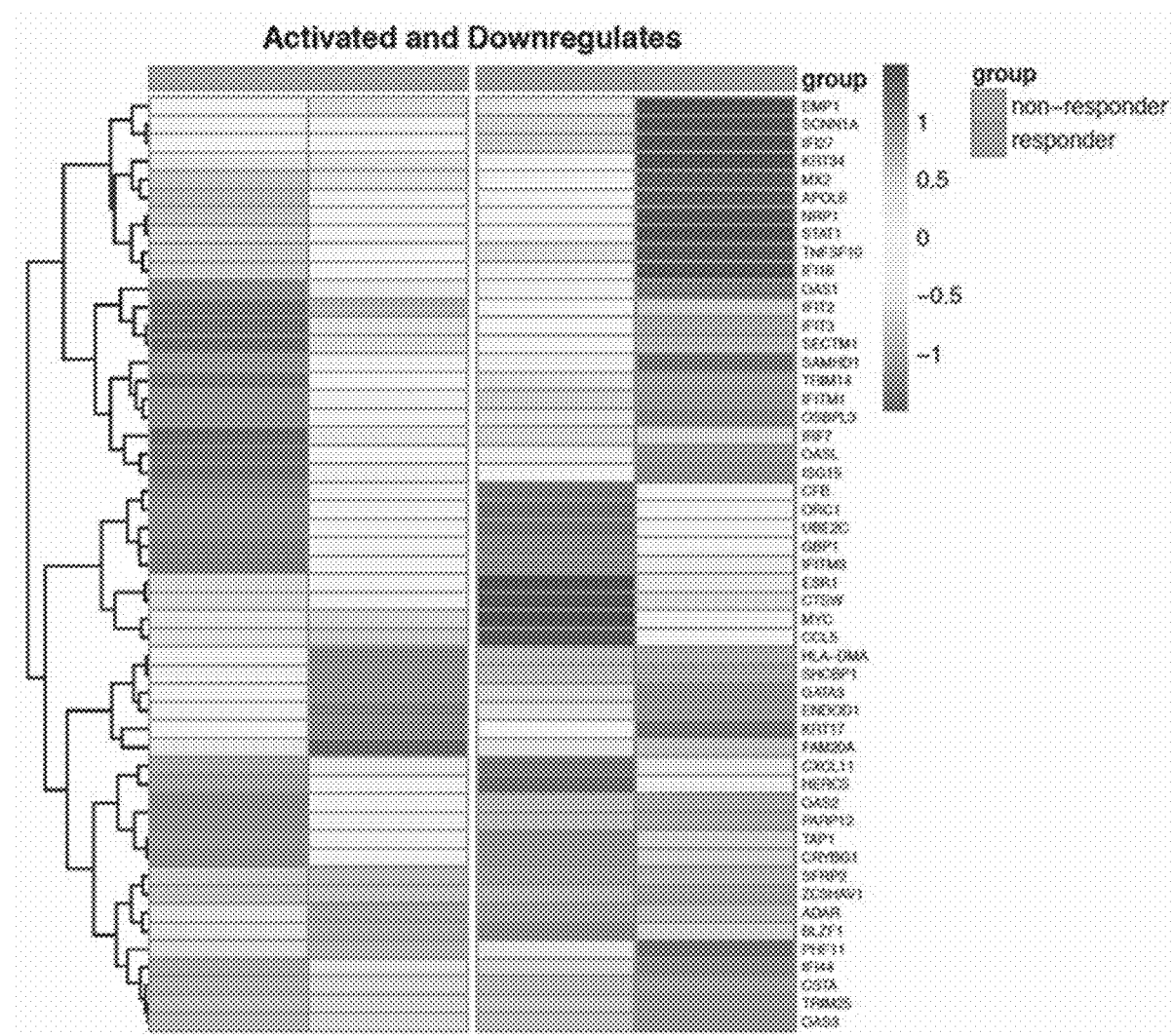

Microarray Datasets. Gene expression profiles from GSE34412 were retrieved via GEO2R. Expression profiles were based on a Custom Human Agilent array (GPL8269). GEO2R was used to perform differential gene expression analysis between responders (GSM847888, GSM847905) and non-responders (GSM847901, GSM847893). Ingenuity Pathway Analysis (IPA) was used to determine regulatory pathways that distinguished between responders and non-responders. Differences in gene expression were consistent with activation of upstream regulator MAPK1 in non-responders vs. responders (Z-score 3.888; overlap p-value 3.07E-15), with 86 genes of 144 having measurements consistent with MAPK1 activation. Log expression values corresponding to the MAPK target genes were extracted from GEO2R for each sample. See FIG. 20. If a gene was represented by more than one probe, the expression value corresponding to the probe with the largest absolute fold-change between responders and non-responders was selected. Genes predicted by IPA to be activated were visualized in a heatmap (expression values were centered and scaled).

Statistical Analysis. All experiments were performed at least twice with n=3 per experiment and all data are expressed as the mean±SEM. Statistical analysis was carried out with software Graph Pad Prism 7. For experiments with multiple comparisons, statistical analysis was performed using one-way ANOVA followed by Dunnett multiple comparison, where means of each column were compared to the mean of a control column. For experiments with two independent groups comparisons, statistical analysis was performed using two-way ANOVA followed by Dunnett multiple comparison, where means of each cell were compared to the control cell mean on that row. A p-value was reported and significance was classified as p<0.05(*), p≤0.005(), p≤0.0005(*), p≤0.0001(****).

Figure 1B:
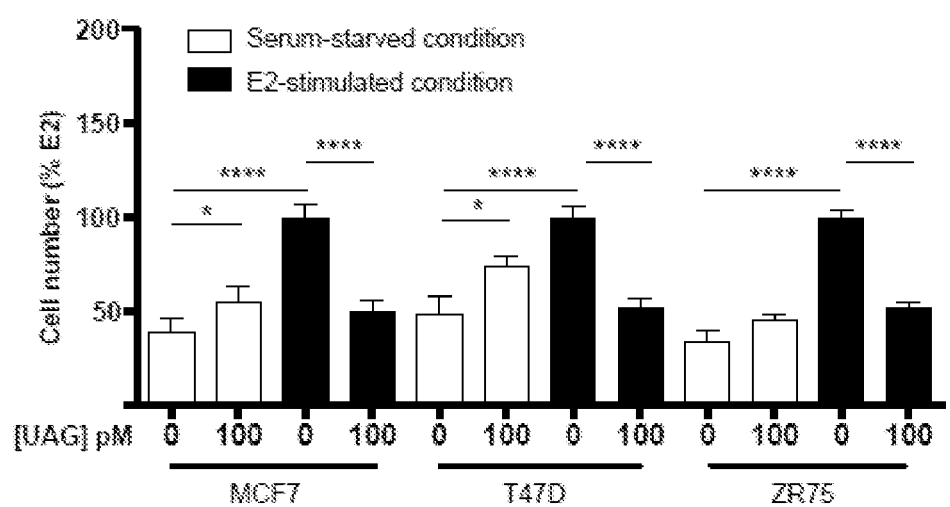
Figure 7A:
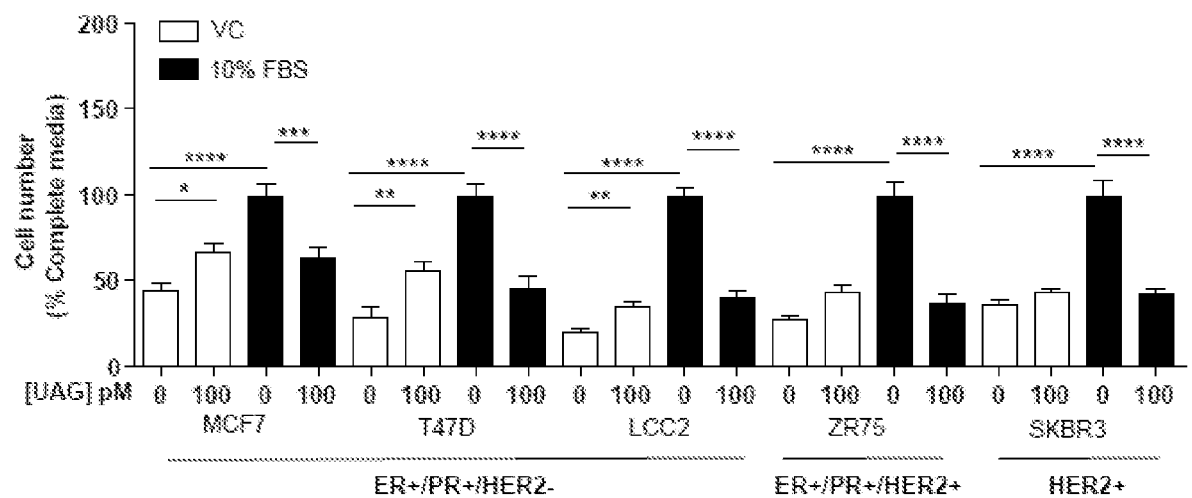
FIGS. 7A-7F show that unacylated ghrelin (UAG) inhibited the growth of breast cancer cells dependent on RAS/RAF mutation status.
Figure 7B:
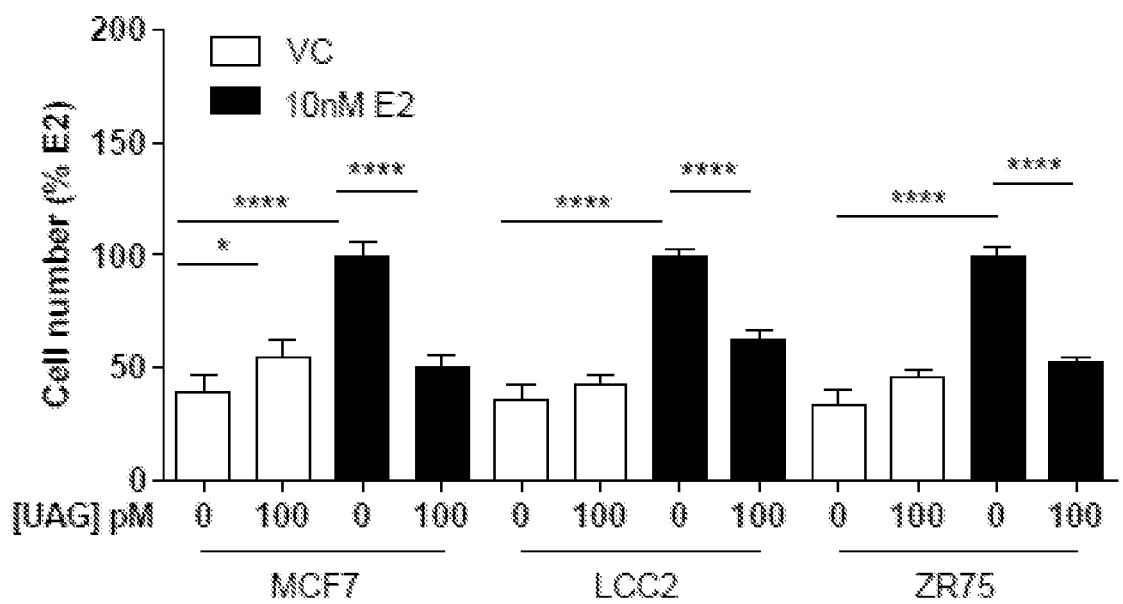
Figure 15A:
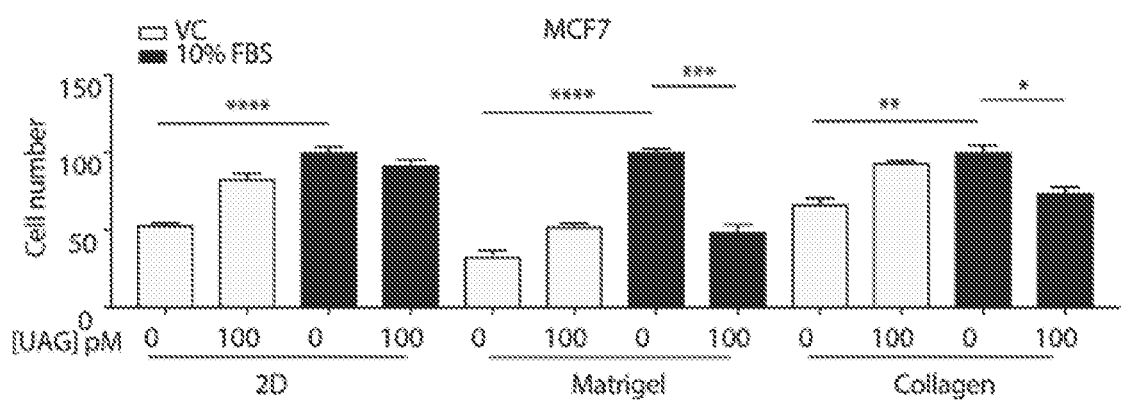
FIGS. 15A-15H show that unacylated ghrelin (UAG) inhibits the growth of breast cancer cells in 3D.
Figure 15B:
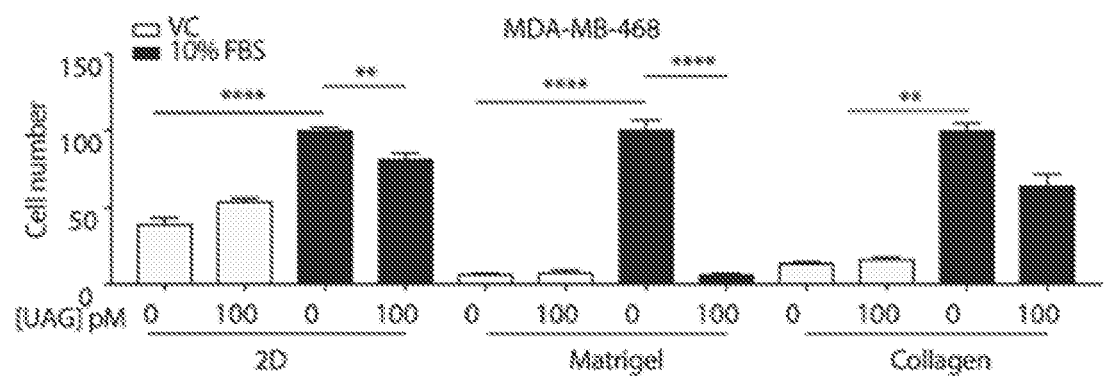
Figure 15C:
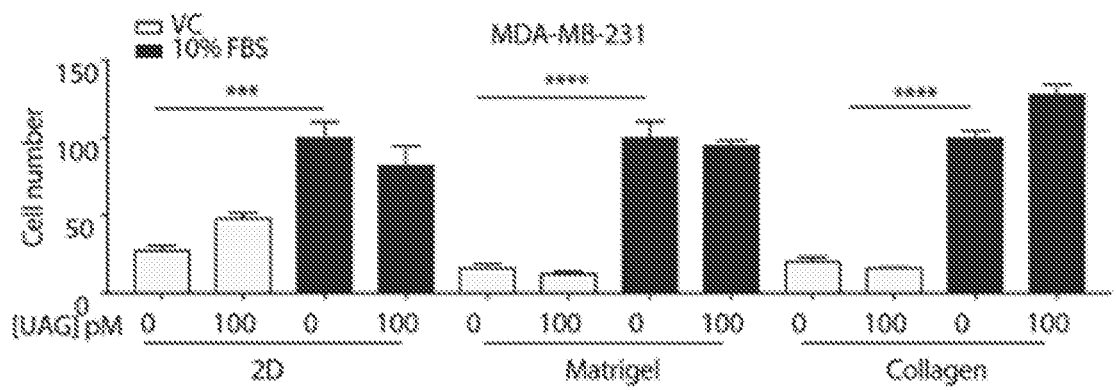
Figure 15D:
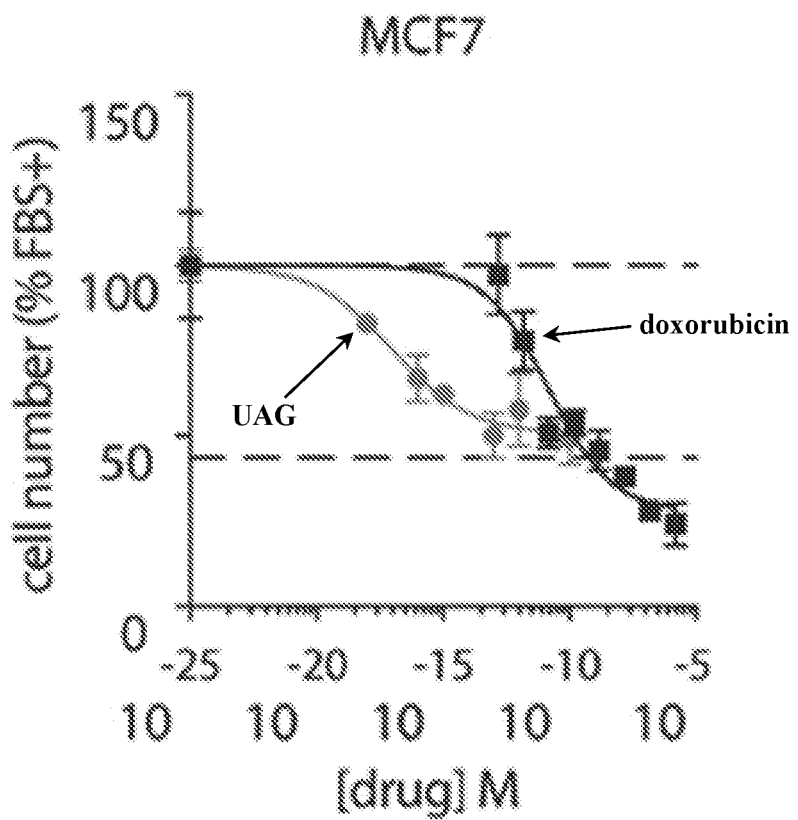
Figure 15E:
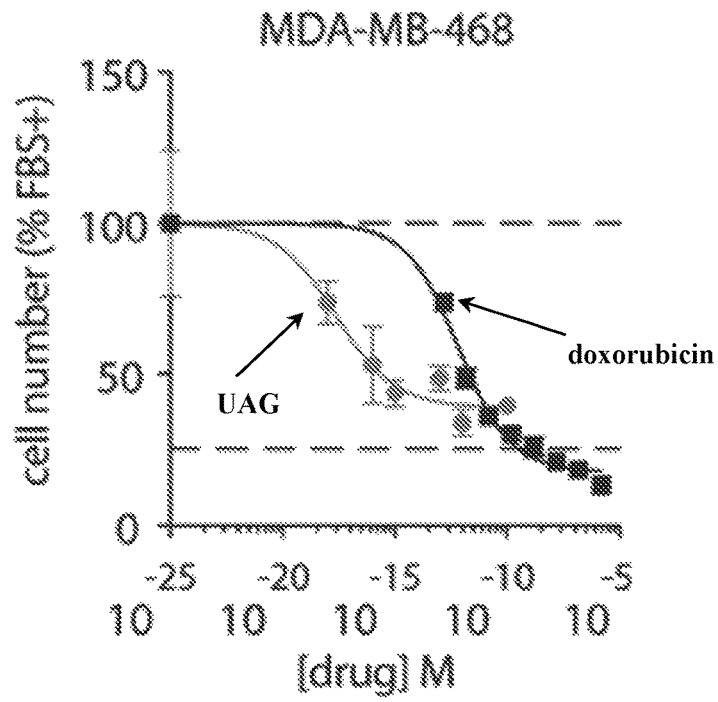
Figure 15F:
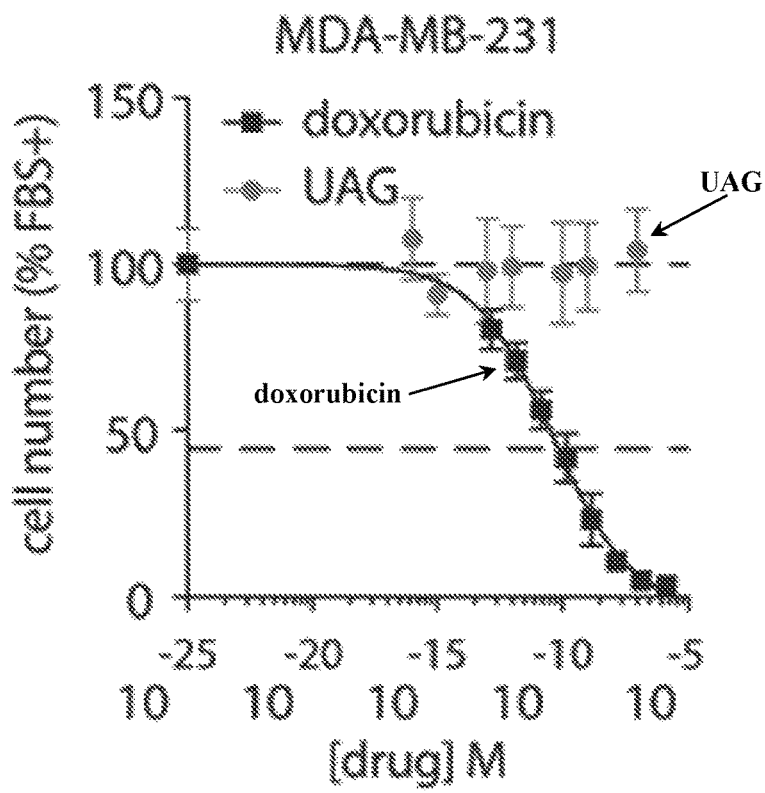
Figure 15G:
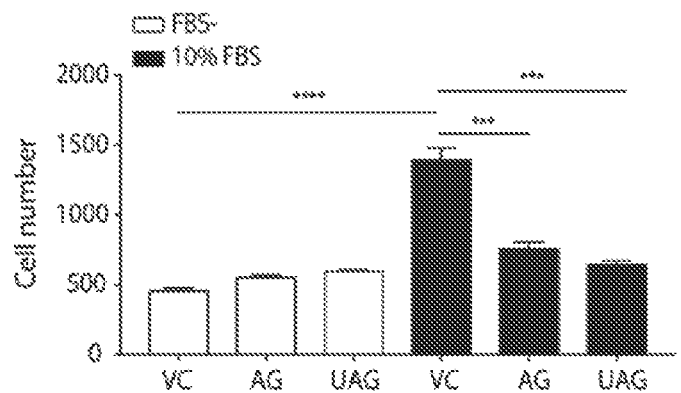
Figure 15H:
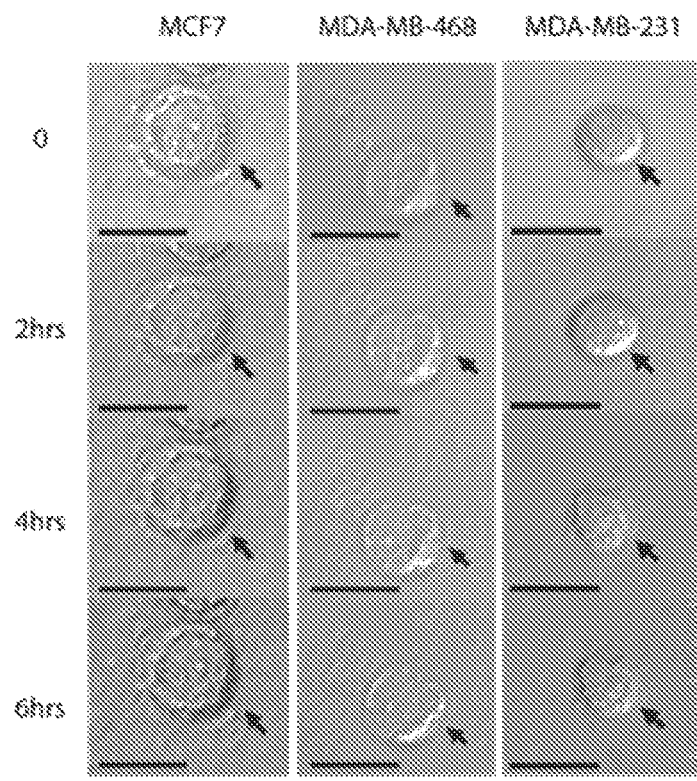

Example 2 Unacylated Ghrelin Inhibits the 3D Growth of Cancer Cells Dependent on KRAS and BRAF Mutation Status One hundred picomolar of unacylated ghrelin was found to suppress the growth of MCF7 and MDA-MB-468 breast cancer cells when grown in 3D, but not 2D (FIG. 15A-15B). At this dose, no effects on MDA-MB-231 cell growth were observed in either 2D or 3D cultures (FIG. 15C). Inhibition of MCF7 and MDA-MB-468 cell growth was observed at $10^{-18}$-$10^{-10}$ M, with maximal effects observed at picomolar doses (FIG. 15D-15E). Again, no significant effect was observed in MDA-MB-231 cells (FIG. 15F). The effect of 100 pM unacylated ghrelin was then tested in a panel of breast cancer cell lines, including ER+/PR+/HER2− (MCF7, T47D), ER+/PR+/HER2+ (ZR-75), HER2+(SKBR3), TNBC (MDA-MB-468, DU4475, MDA-MB-157, Hs578T, MDA-MB-231), and tamoxifen-resistant (LCC2) cells (FIGS. 1A-1C and 7A-7C). As shown in FIGS. 1A, 1C, 7A, and 7C, under serum-free conditions, unacylated ghrelin stimulated or had no effect on the growth of breast cancer cells. In the presence of serum, unacylated ghrelin significantly inhibited the growth of all breast cancer cells examined except for three of the TNBC cell lines (DU4475, HS578T and MDA-MB-231). As shown in FIGS. 1B, and 7B, unacylated ghrelin also suppressed the estradiol-stimulated growth of $ER^+$ breast cancer cells. Interestingly, as shown in FIG. 15G, acyl ghrelin (AG) and UAG (100 pM) inhibited breast cancer cell growth in serum-stimulated conditions.

Figure 7C:
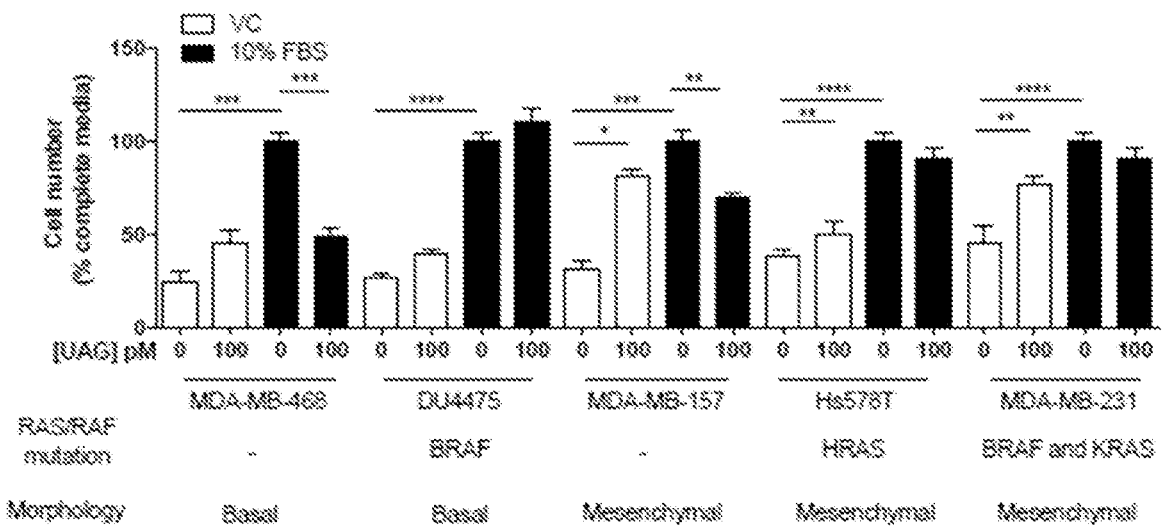
Figure 7D:
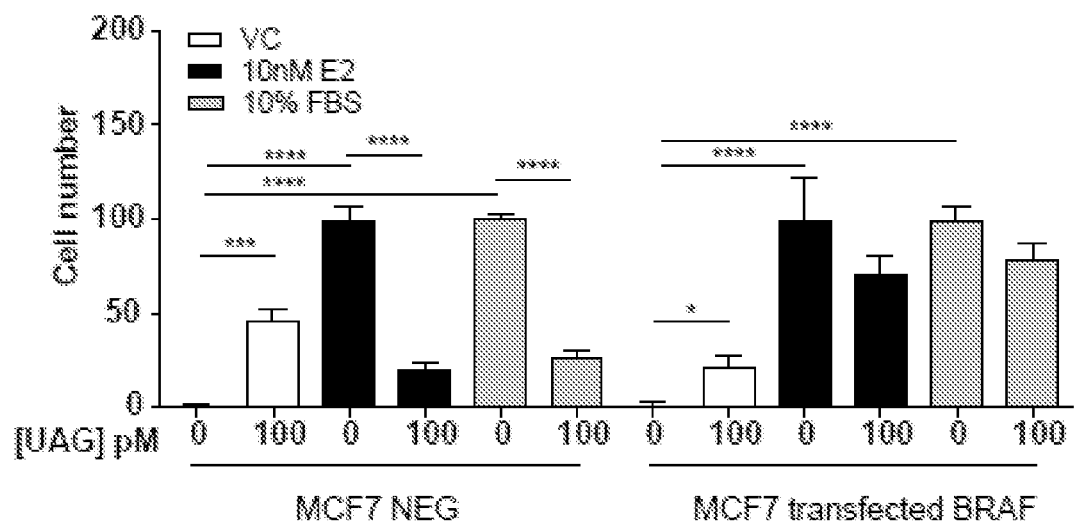
Figure 7E:
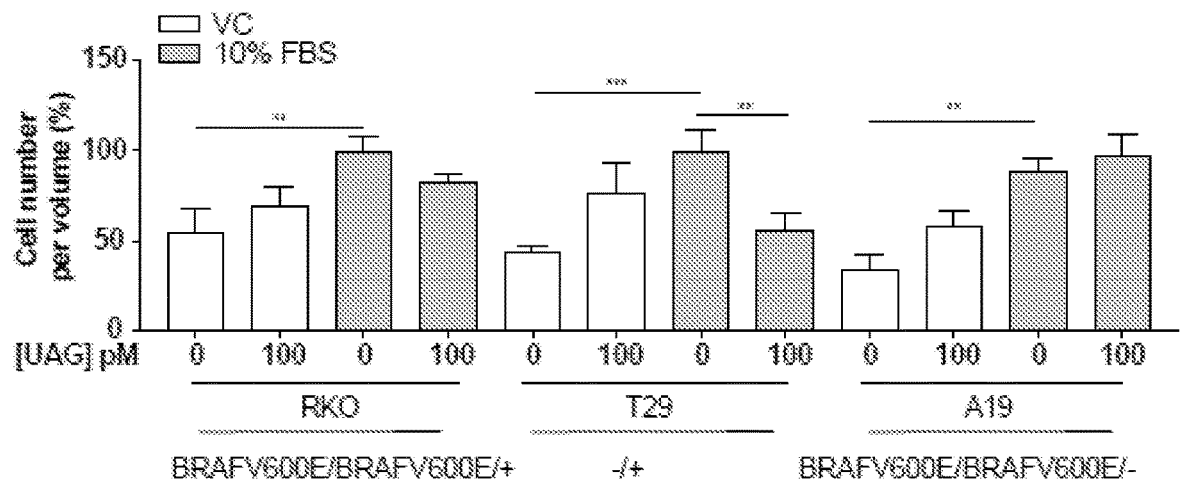
Figure 7F:
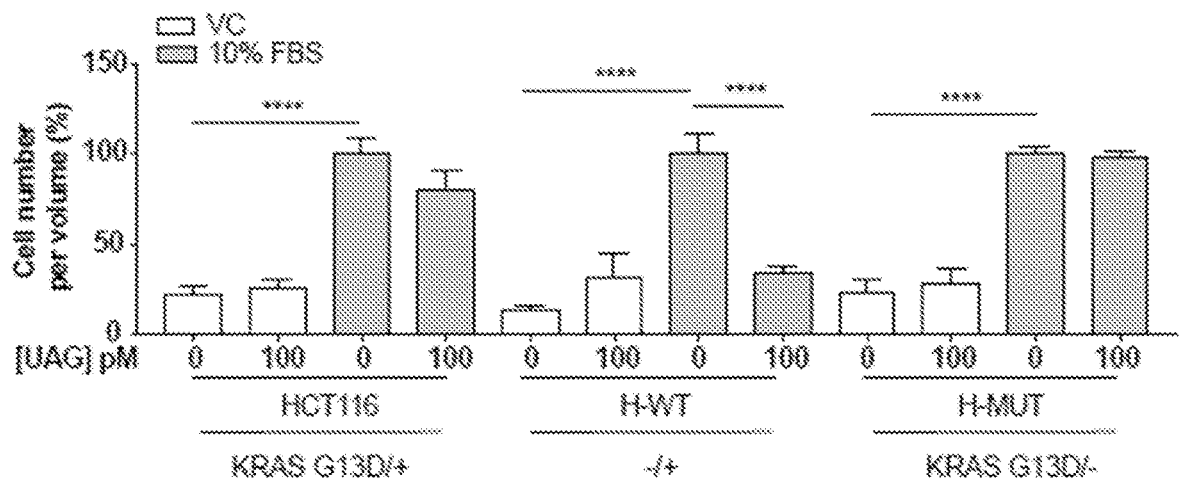

Responsive cells included those having mutations in PTEN and PI3K, while resistant cell lines carried mutations in BRAF, HRAS and/or KRAS (FIGS. 1C, 7C and 13). To test whether these mutations confer resistance to treatment, the effects of unacylated ghrelin were examined in BRAFV600E-transfected MCF7 cells or colon cancer cells (RKO, HCT116) that carry mutations in BRAF or KRAS, respectively. As shown in FIG. 7D, transient transfection of MCF7 cells with mutant BRAF led to resistance to unacylated ghrelin treatment in estradiol- and serum-stimulated cells. Des-acyl ghrelin suppressed the growth of colon cancer cells at picomolar doses provided they are wild-type for BRAF and KRAS. See FIG. 7F. Unacylated ghrelin had no effect on the growth of RKO and HCT116 cells (FIGS. 1D, 7E and 7F). However, loss of the mutant alleles for BRAF or KRAS led to sensitization of RKO and HCT116 cells, respectively. Loss of the wild type allele had no significant effect. Binding of Cy3-labeled unacylated ghrelin to responsive and non-responsive cells (FIG. 1511) suggests that resistance is not due to lack of binding or receptor expression.

Figure 2A:
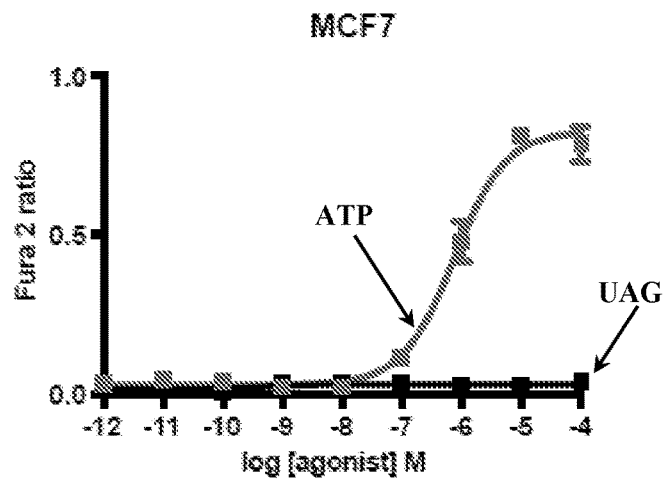
FIGS. 2A-2E show the inhibition of breast cancer cell growth by des-acyl ghrelin involves $G\alpha_i$, and MAPK signaling.
Figure 2B:
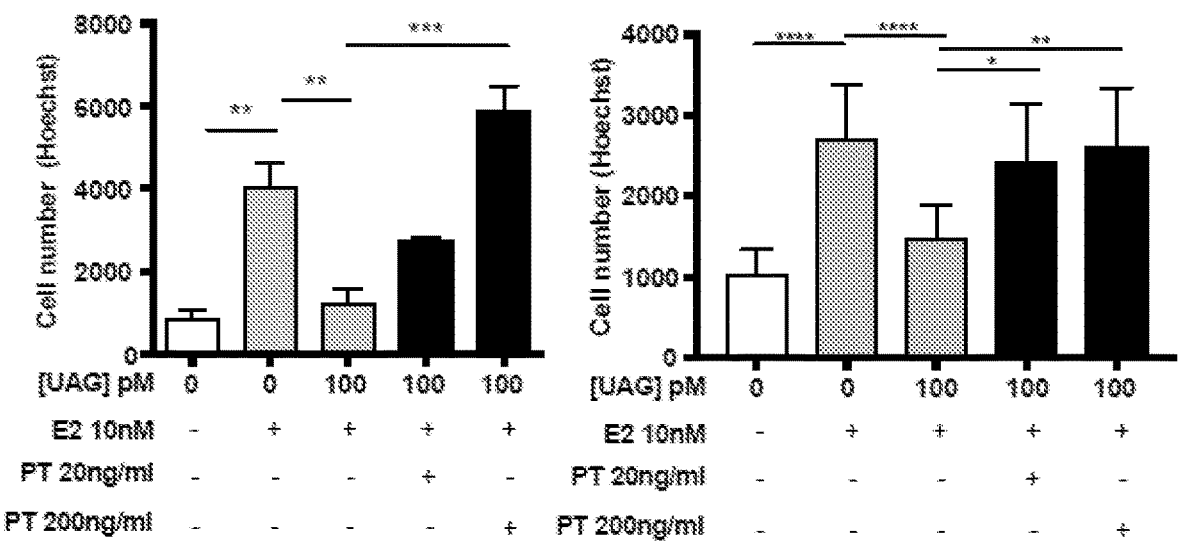
Figure 2C:
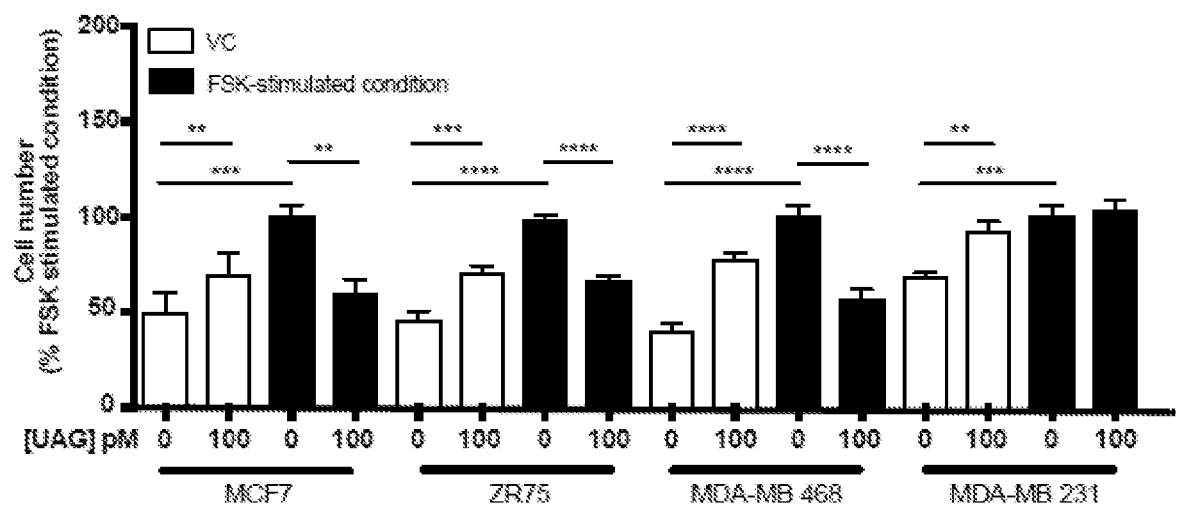
Figure 2D:
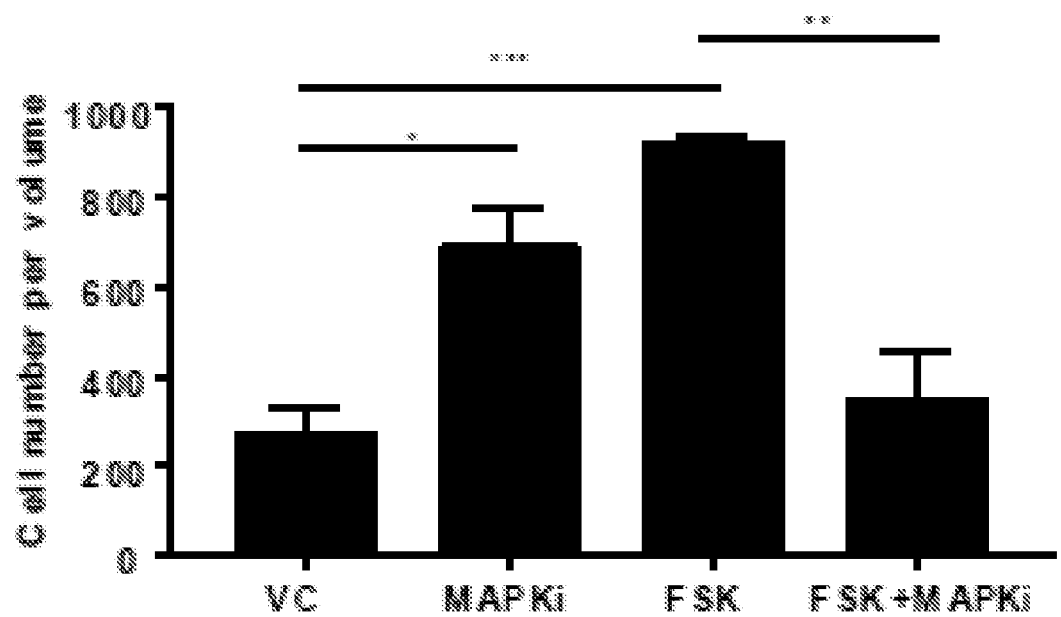
Figure 2E:
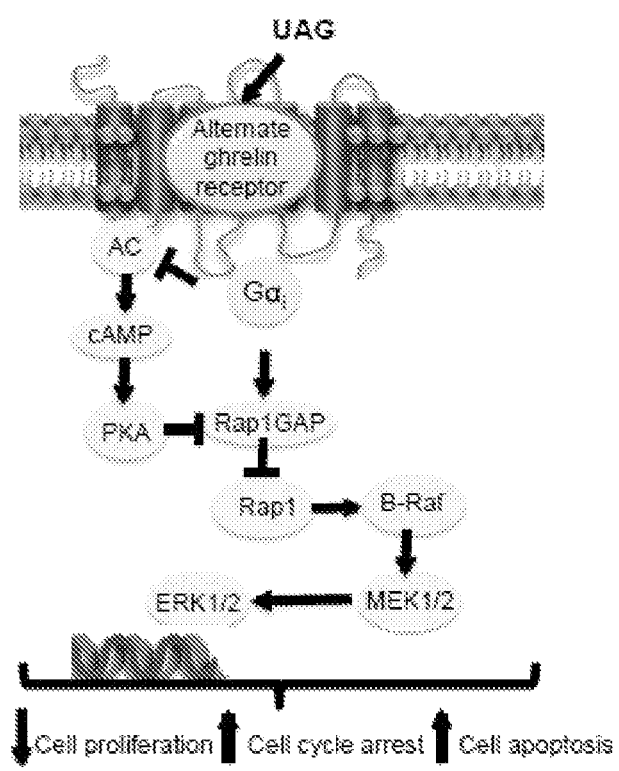
Figure 8A:
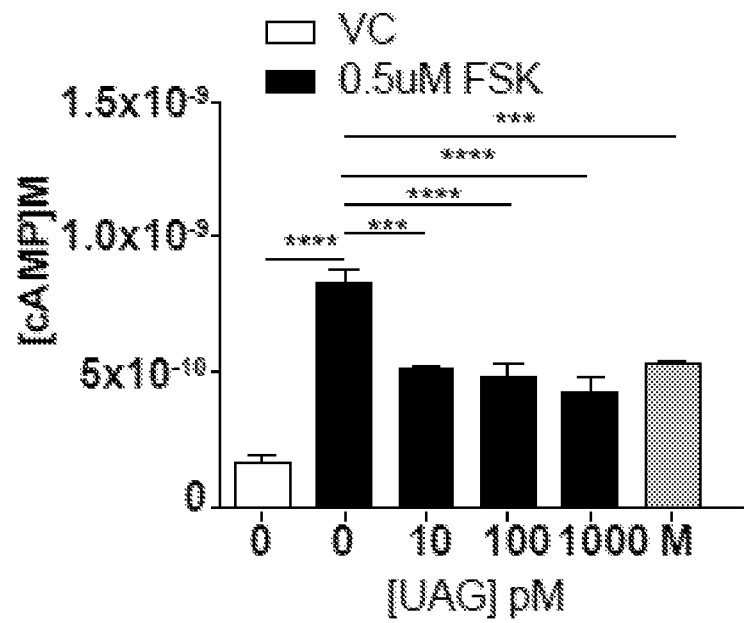
FIGS. 8A-8I show that unacylated ghrelin (UAG) suppressed breast cancer cell growth via Gαi-dependent inhibition of cAMP formation.
Figure 8B:
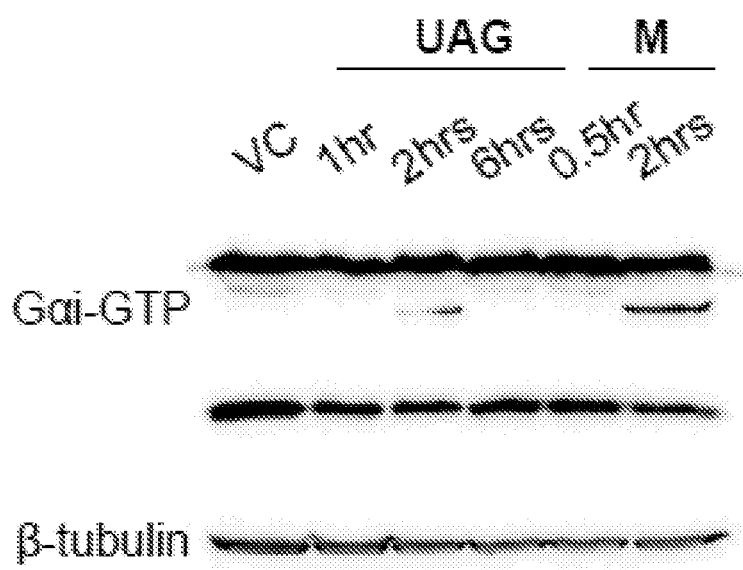
Figure 16A:
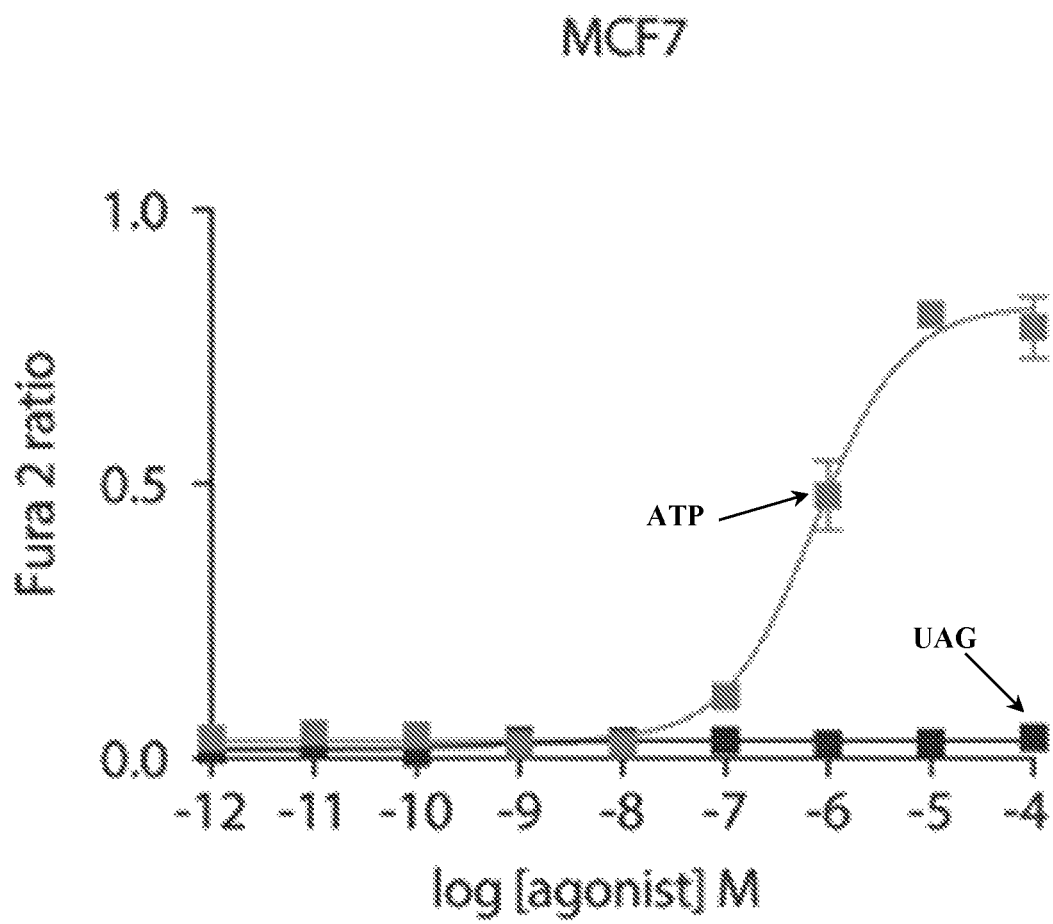
FIGS. 16A-16G show that unacylated ghrelin (UAG) suppresses breast cancer cell growth via $G\alpha_i$-dependent mechanisms.

Example 3: Unacylated Ghrelin Suppresses Breast Cancer Cell Growth via $G\alpha_i$-Dependent Inhibition of cAMP Formation The receptor for unacylated ghrelin is currently unknown, but hypothesized to be a GPCR. Effects of unacylated ghrelin on second messenger systems were assessed by measuring the formation of cAMP and the release of intracellular calcium in MCF7 cells. As shown in FIGS. 2A, 8A and 16A, unacylated ghrelin significantly suppressed the formation of cAMP, but had no effect on intracellular calcium release. Effects on cAMP suggested a Gardependent mechanism. As shown in FIG. 8B, activation of $G\alpha_i$ by unacylated ghrelin was observed after 2-hr treatment, as measured by pull-down of GTP-bound $G\alpha_i$.

Figure 8C:
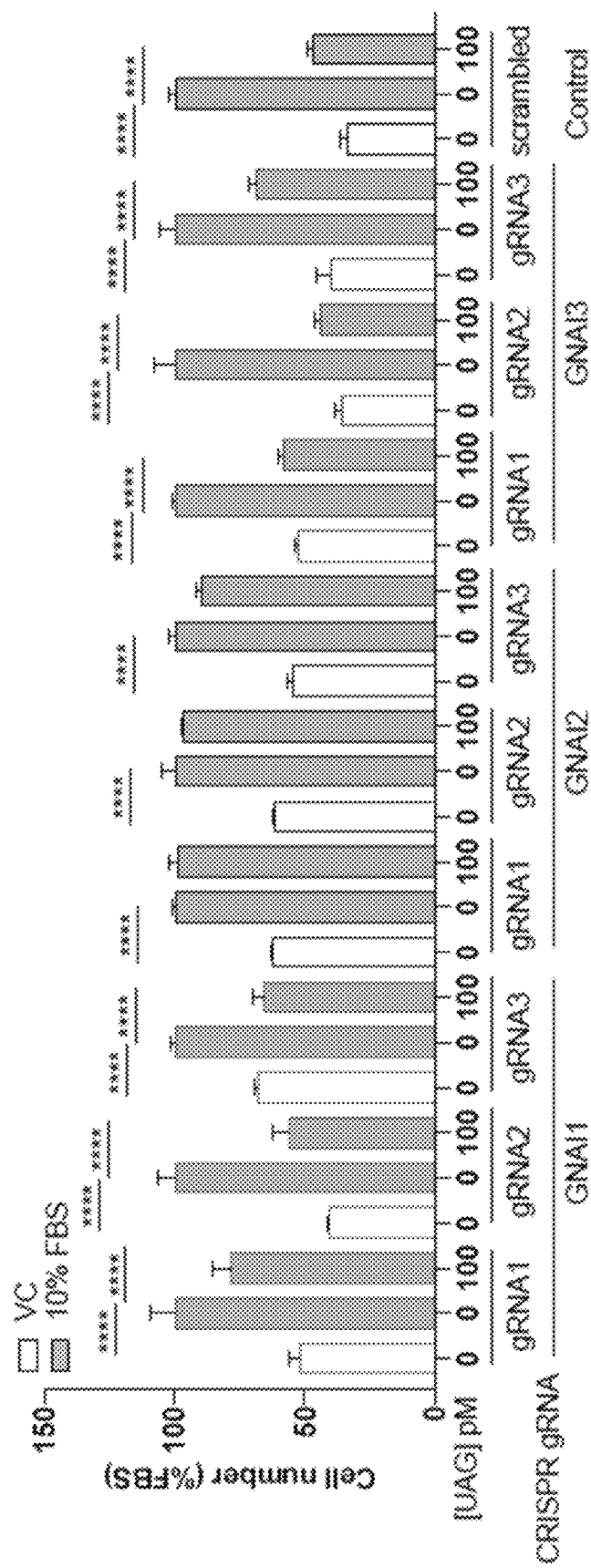
Figure 8D:
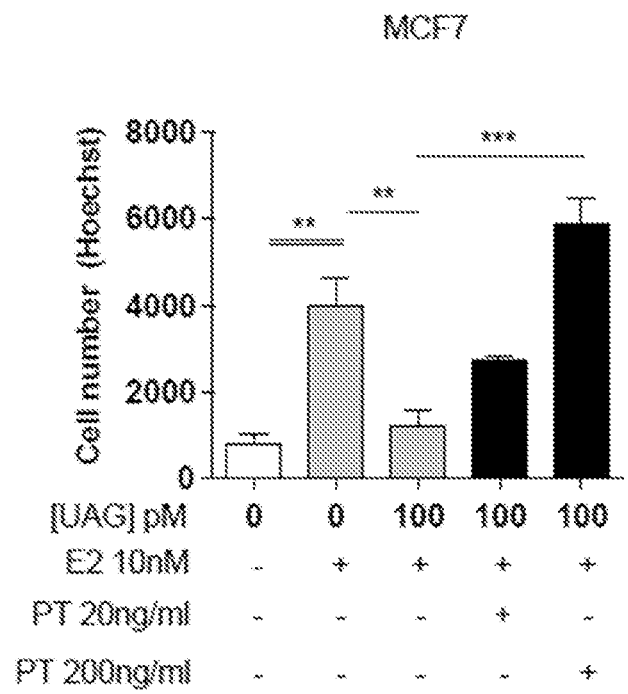
Figure 8E:
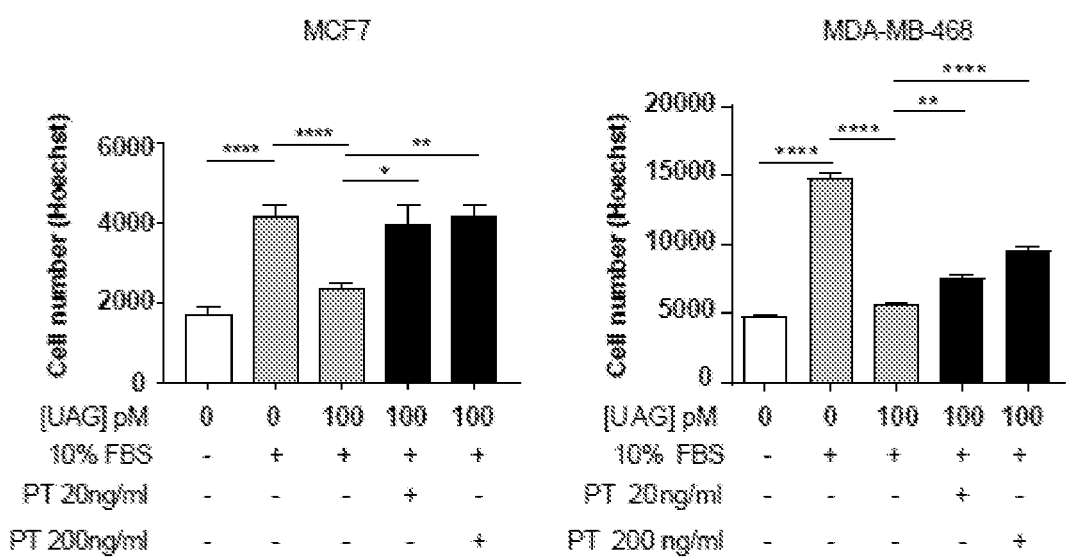
Figure 8F:
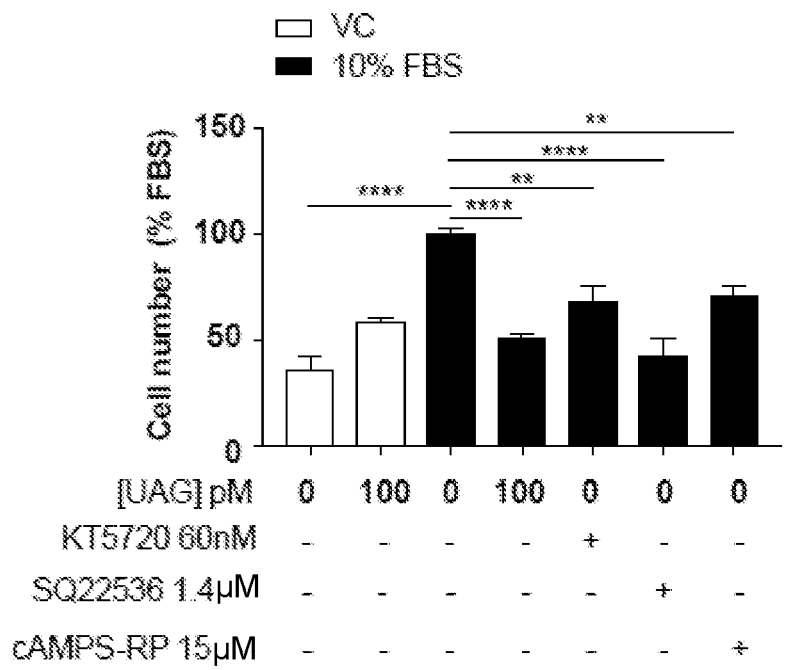
Figure 8G:
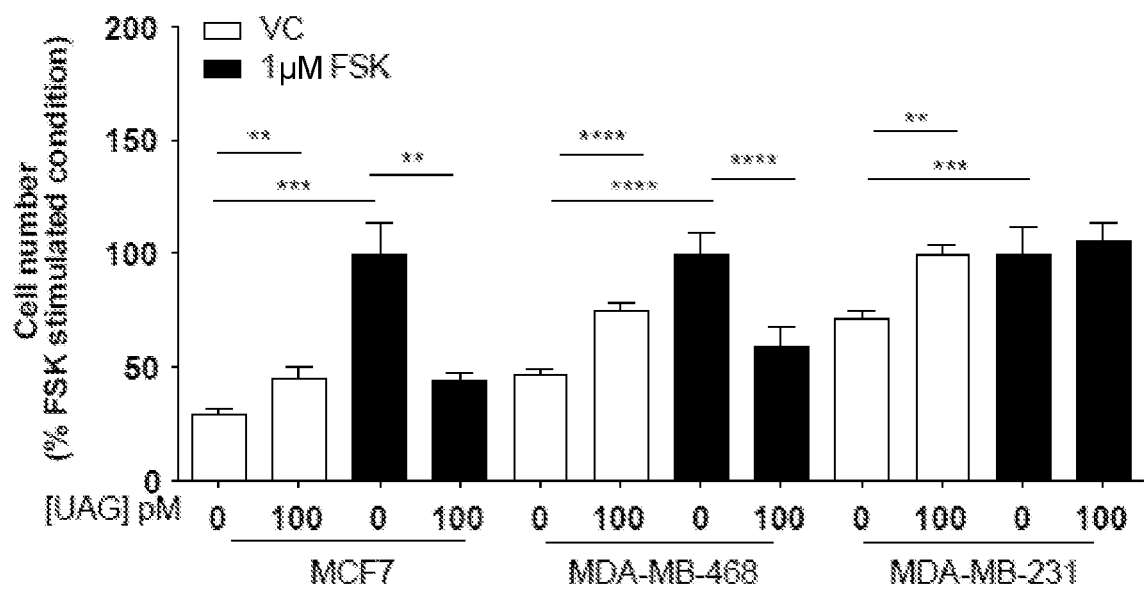
Figure 8H:
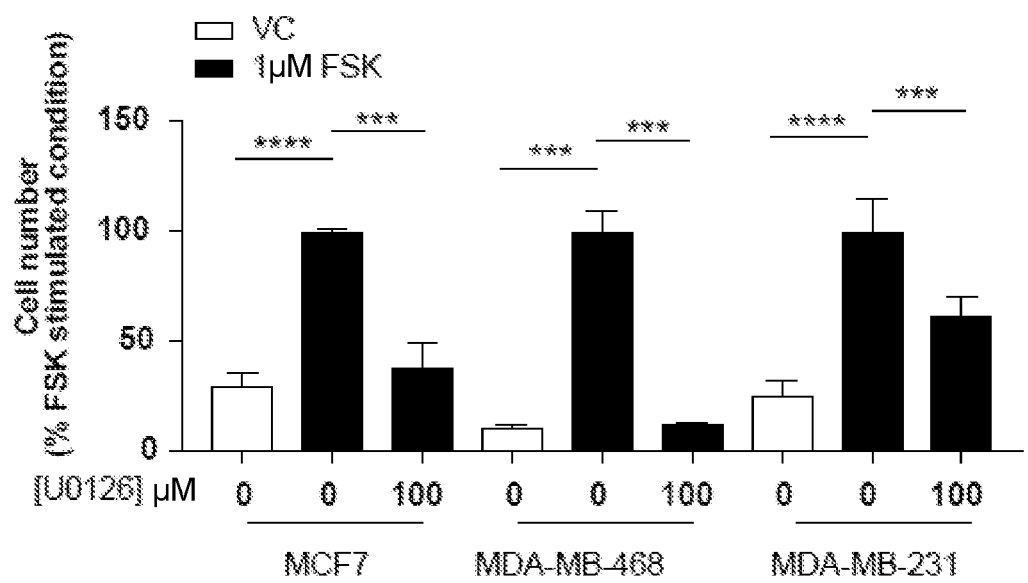
Figure 8I:
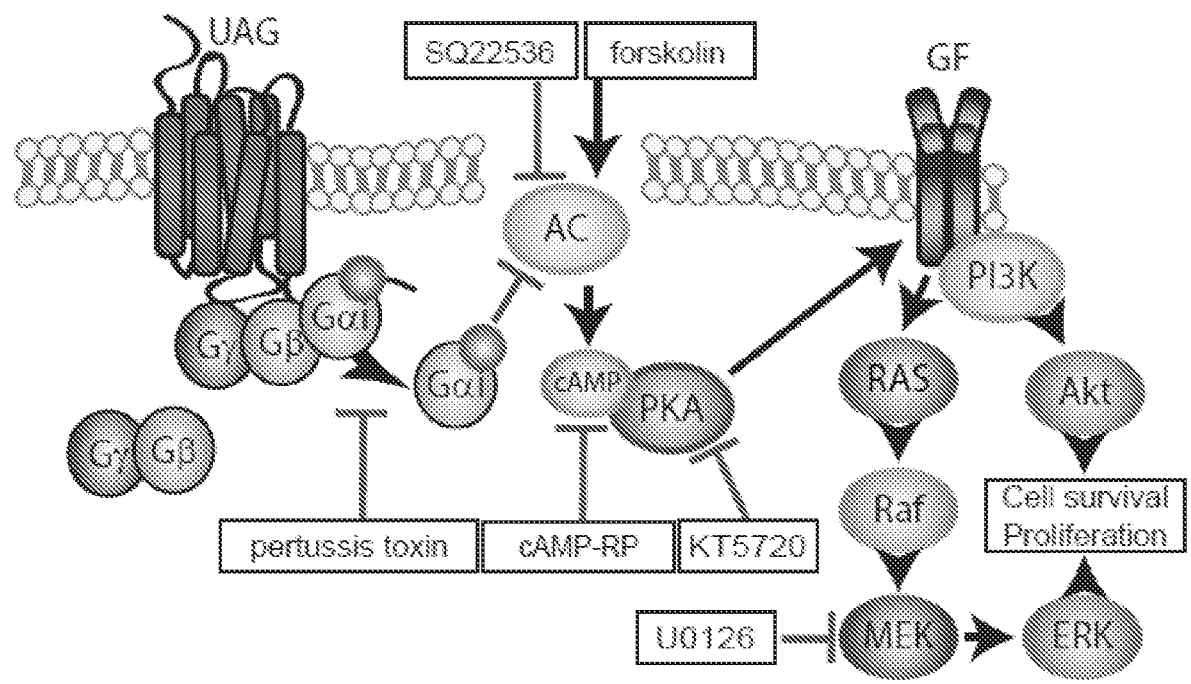
Figure 16B:
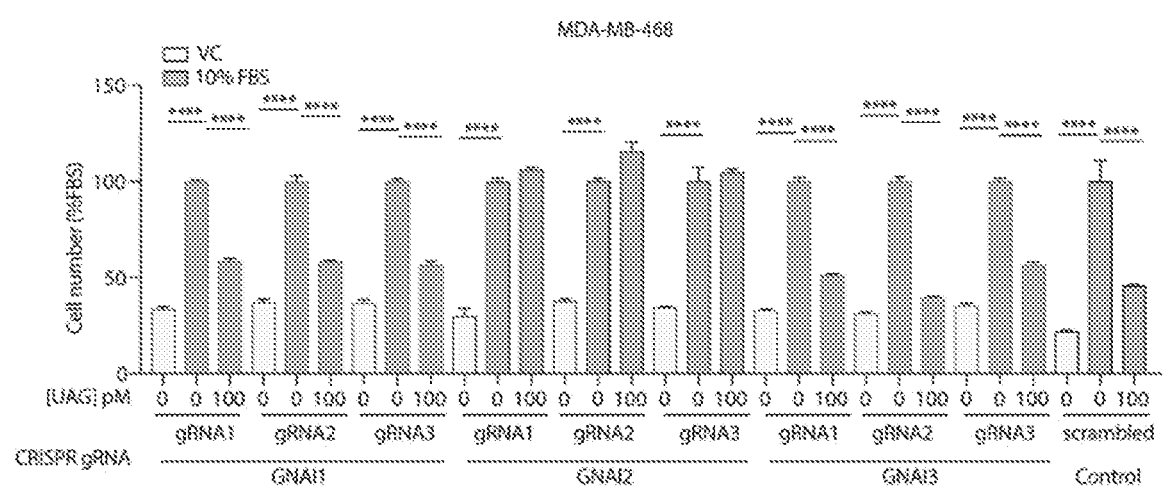
Figure 16C:
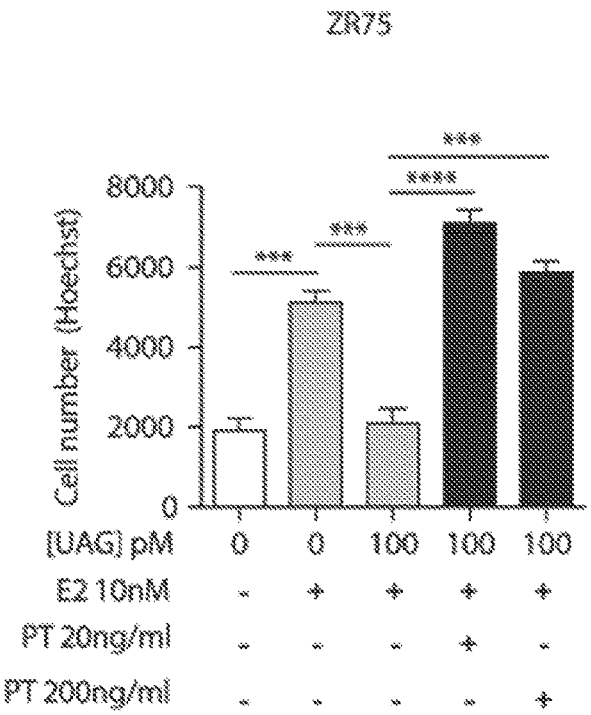
Figure 16D:
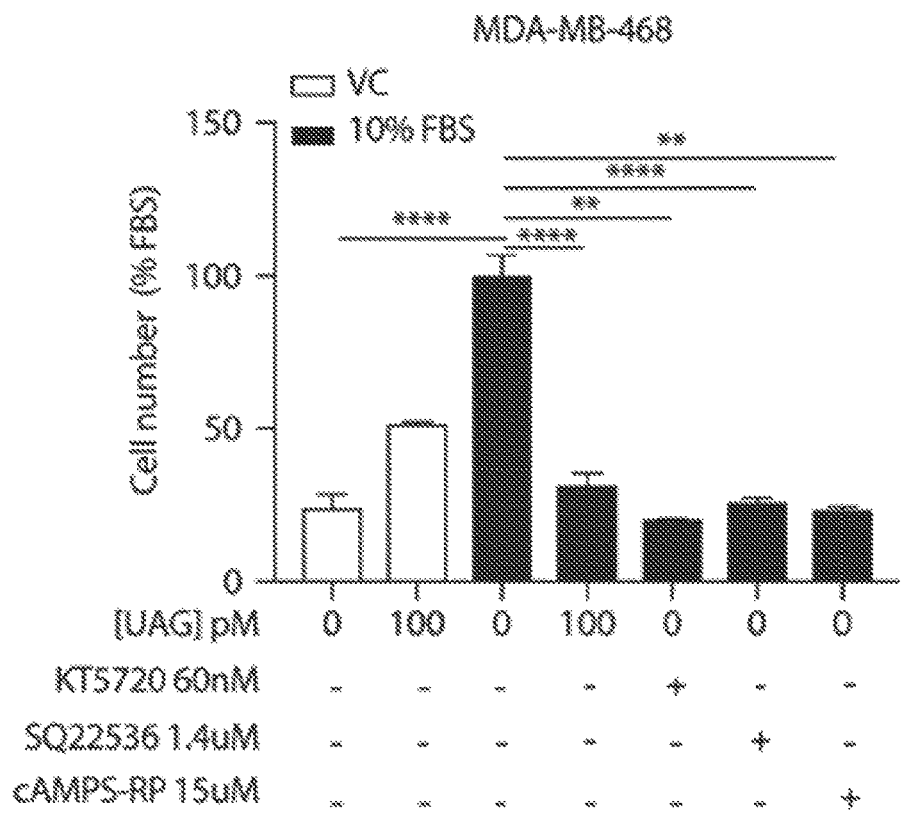
Figure 16E:
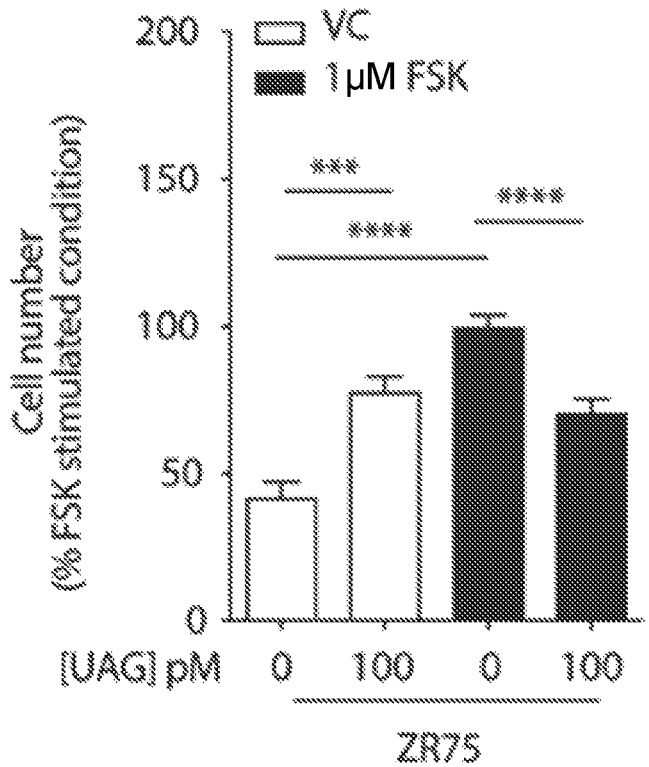
Figure 16F:
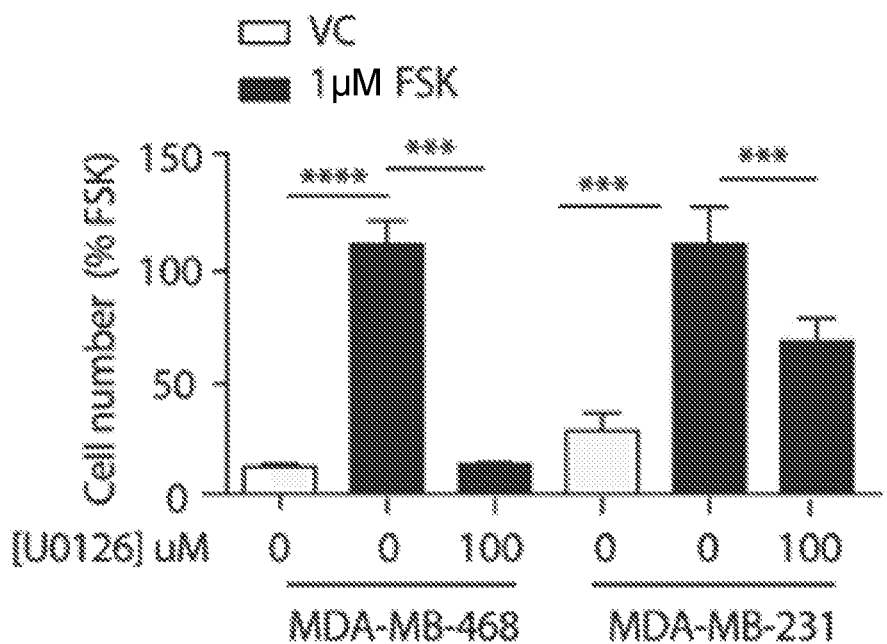
Figure 16G:
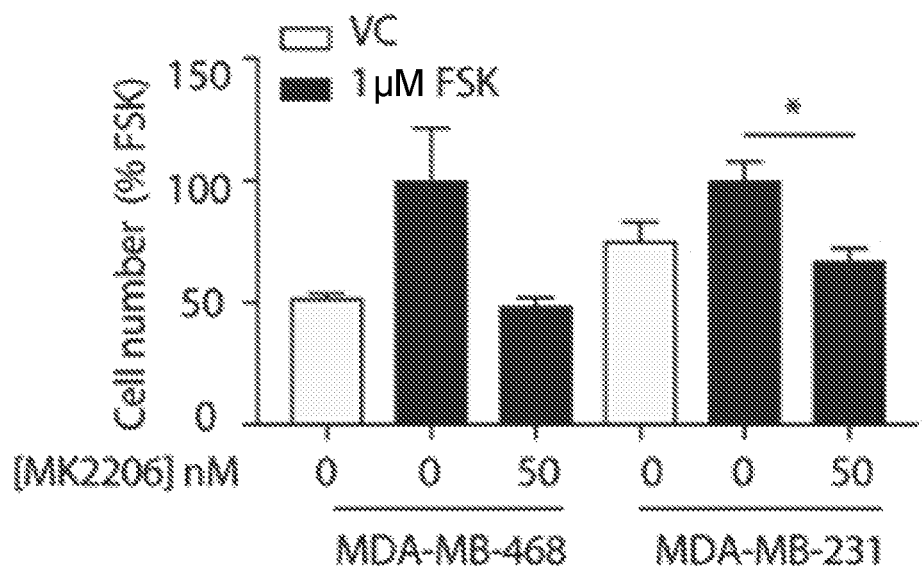

To test dependence of growth inhibitory effects of unacylated ghrelin on $G\alpha_i$, 3D growth assays were performed in cells where the Garencoding gene, guanine nucleotide-binding protein, alpha subunit (GNAI), was knocked out (CRISPR; FIGS. 8C, and 16B) or in the presence of $G\alpha_i$ inhibitor pertussis toxin (FIGS. 2B, 8D-8E, and 16C). Unacylated ghrelin had no effect on cells lacking Gα I subunit 2 (GNAI2), whereas the growth of cells where Gα I subunit 1 (GNAI1) and Gα I subunit 3 (GNAI3) were targeted were significantly suppressed. GNAI2 was also found to be required for unacylated ghrelin activity in MDA-MB-468 cells (FIG. 16D). Effects of unacylated ghrelin were also attenuated in cells treated with pertussis toxin, in the presence of estradiol or serum. To determine whether inhibition of cAMP is sufficient to suppress the serum-stimulated growth of breast cancer cells, MCF7 and MDA-MB-468 cells were treated with adenylyl cyclase and PKA inhibitors, SQ22536 and KT5720, and cAMP antagonist, cAMPS-RP (FIG. 8F and FIG. 16D). Inhibition of cAMP formation and PKA led to a significant reduction in cell number. Effects of cAMP on cell growth were then examined in cells treated with adenylyl cyclase stimulator, forskolin. As shown in FIGS. 2C, 8G, and 16E-16G, forskolin stimulated the growth of MCF7, MDA-MB-468 and MDA-MB-231 cells, and similar to effects of unacylated ghrelin in serum- or estradiol-stimulated conditions, unacylated ghrelin suppressed the forskolin-mediated induction of MCF7 and MDA-MB-468 cell growth, but not MDA-MB-231. As resistance to unacylated ghrelin was observed in cells that carry mutations in RAS and RAF, the link between cAMP and MAPK signaling was next examined in MCF7, MDA-MB-468 and MDA-MB-231 cells in 3D (FIG. 811). Inhibition of MEK activity using U0126 led to a significant reduction in the forskolin-stimulated growth of all cell lines.

Example 4: Unacylated Ghrelin Inhibits MAPK and Akt Signaling

Figure 9A:
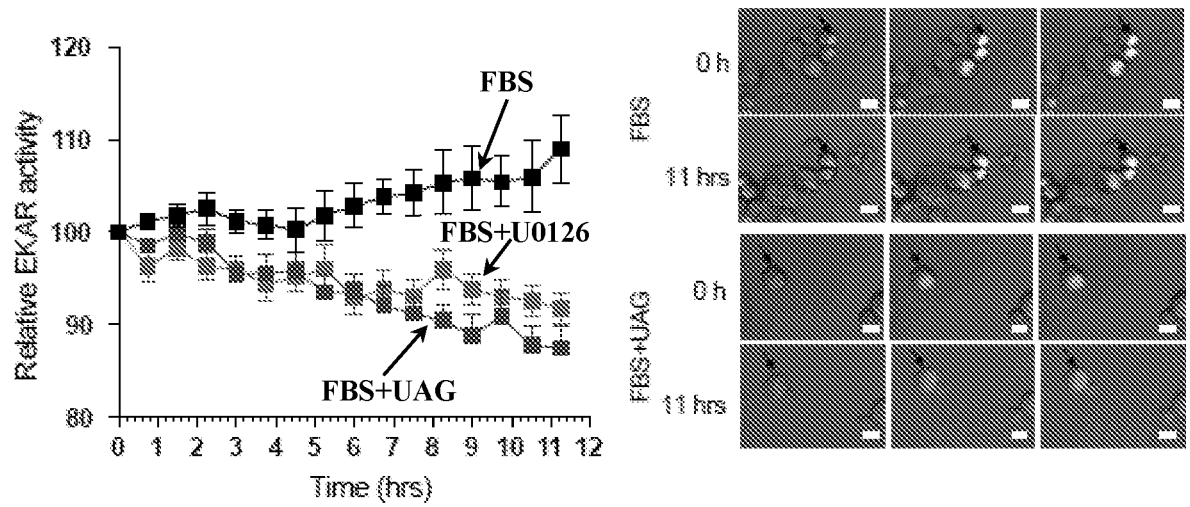
FIGS. 9A-9J show that unacylated ghrelin (UAG) inhibited MAPK and Akt signaling.
Figure 9B:
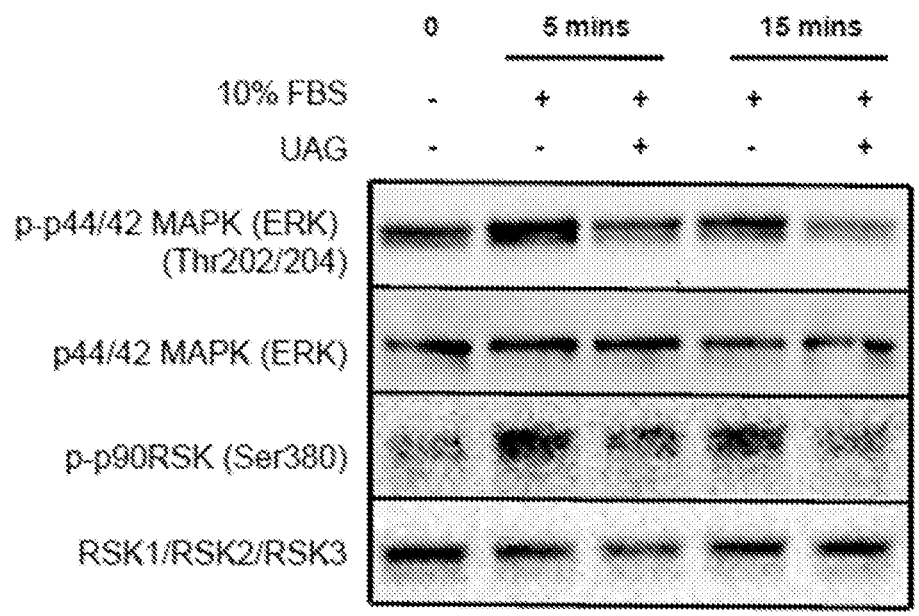
Figure 9C:
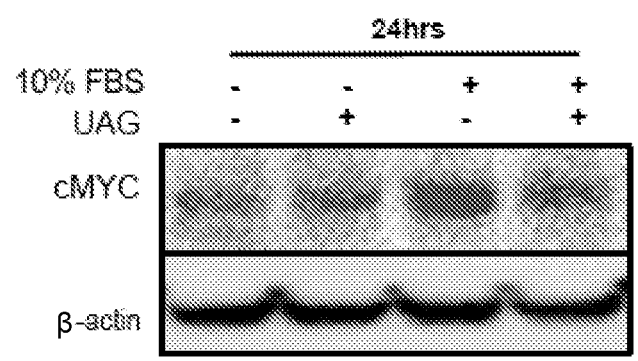
Figure 9D:
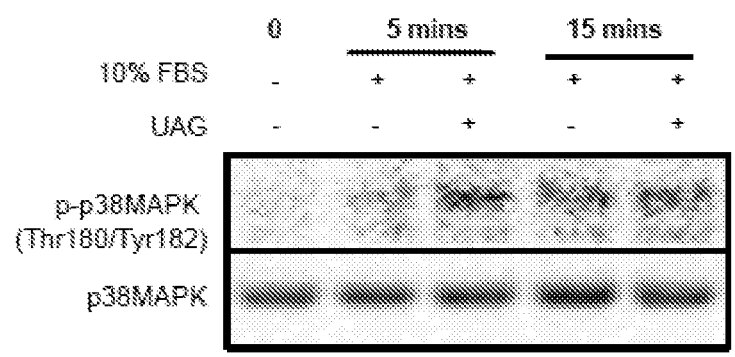
Figure 9E:
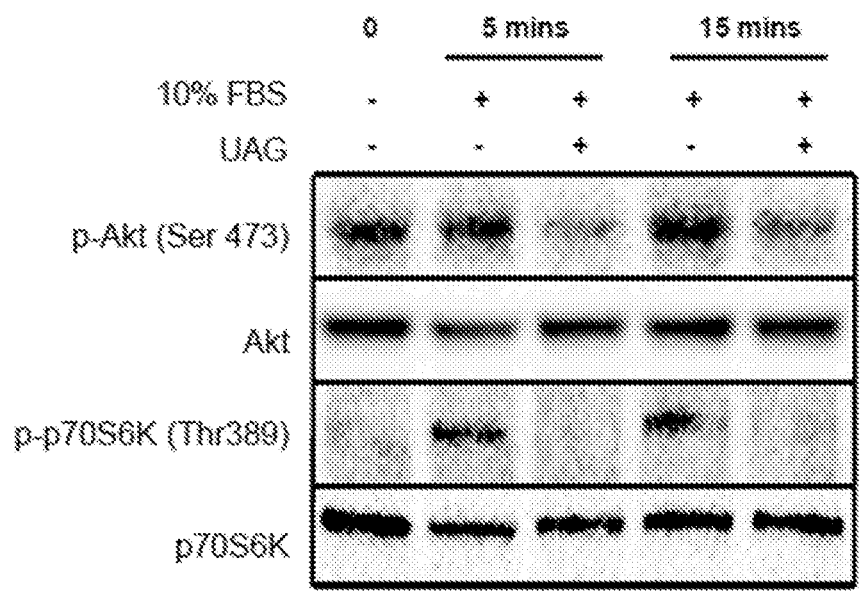
Figure 9F:
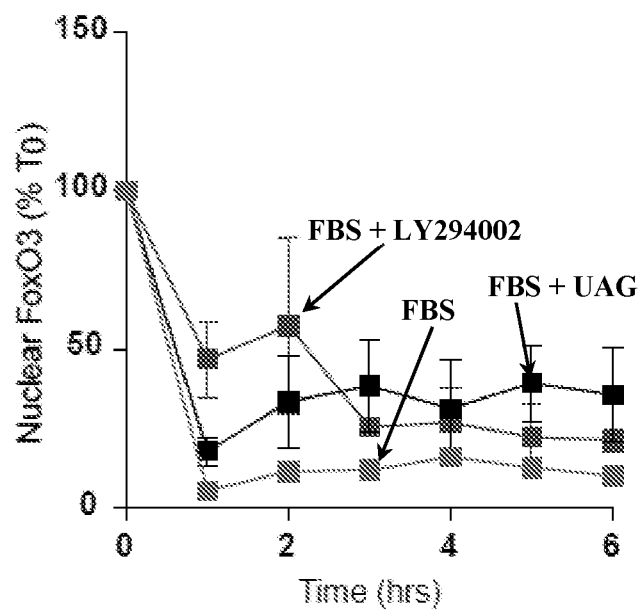
Figure 9G:
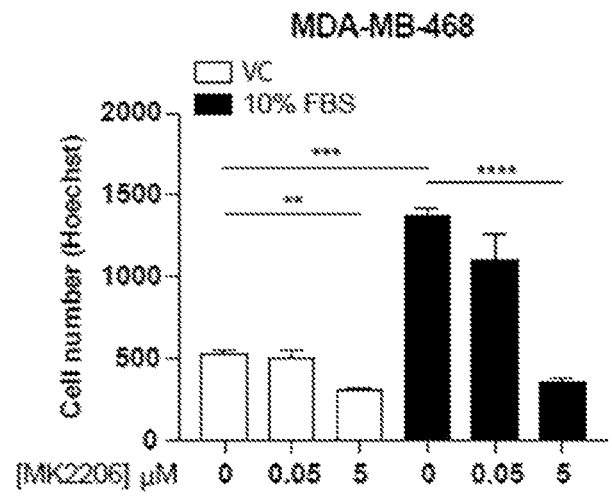
Figure 9H:
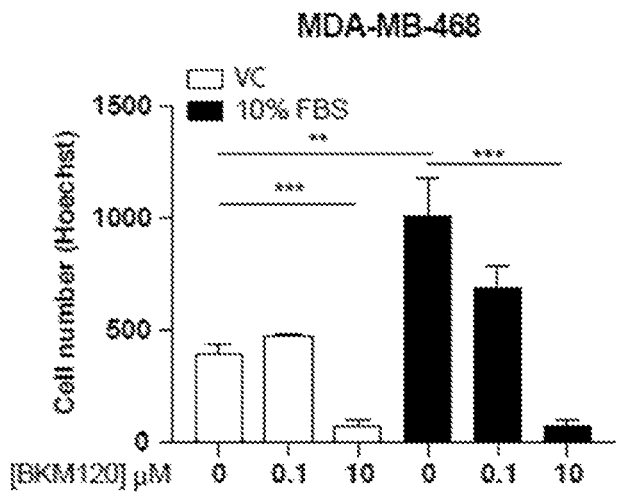
Figure 9I:
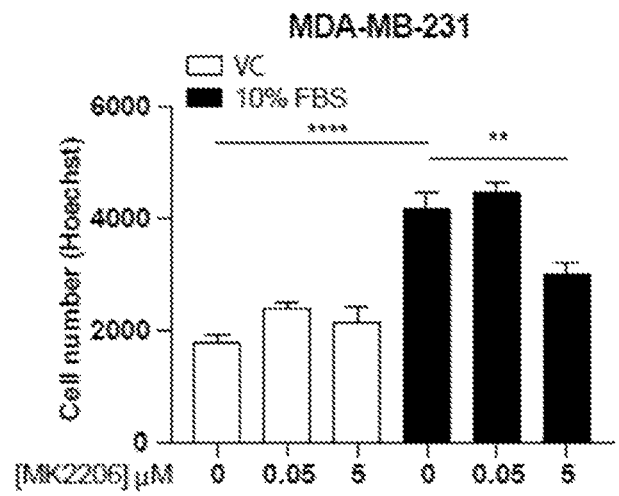
Figure 9J:
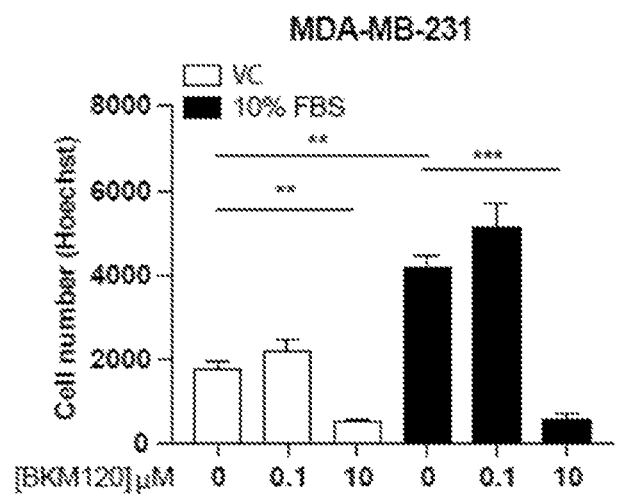
Figure 17A:
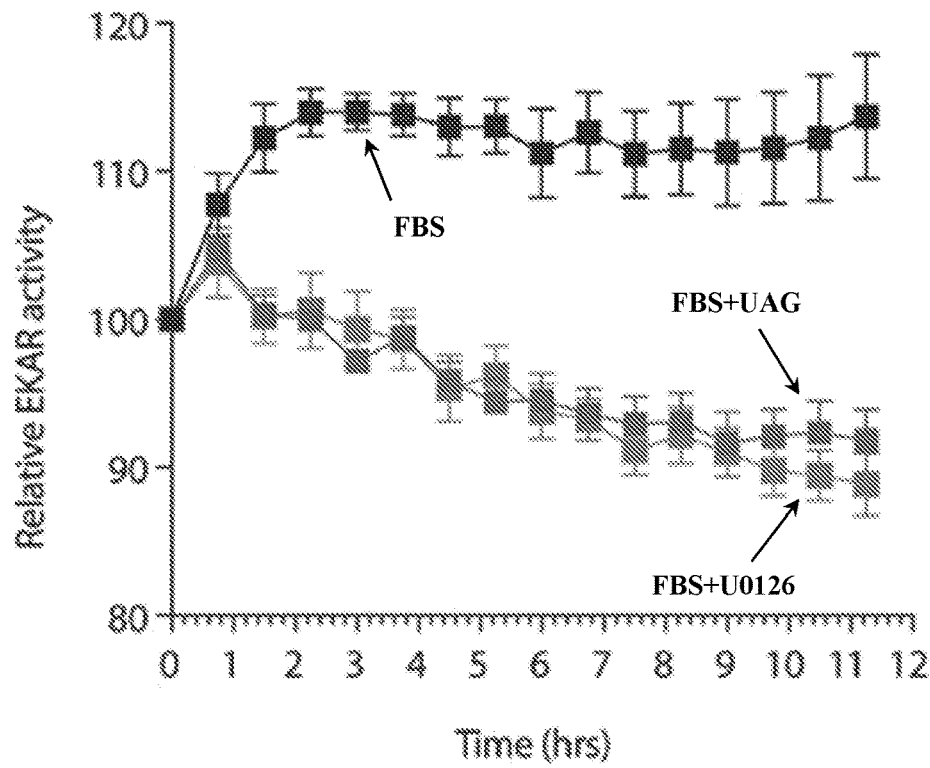
FIGS. 17A-17N show that unacylated ghrelin (UAG) inhibits MAPK and Akt signaling.
Figure 17B:
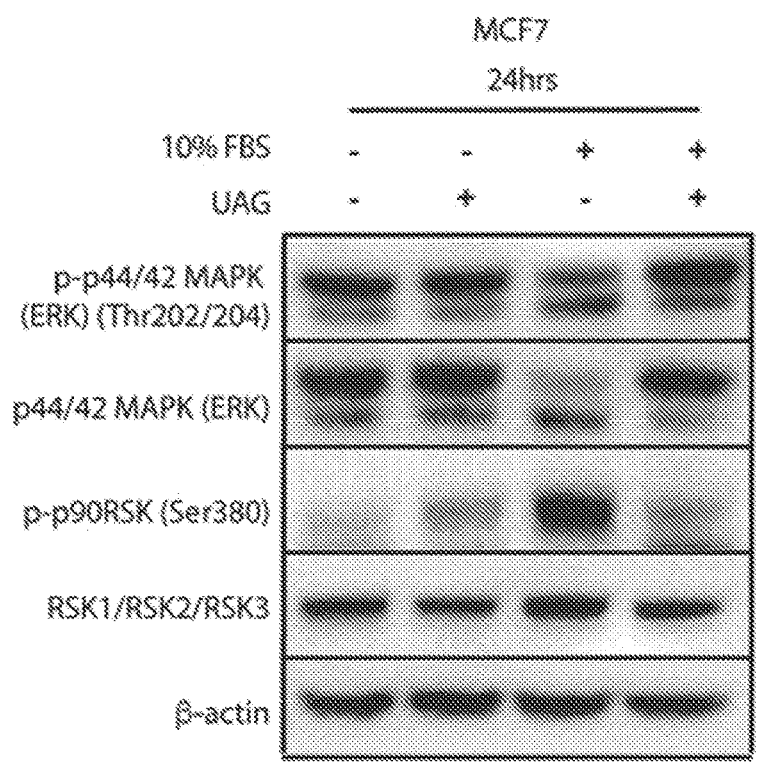
FIGS. 17B-17D show western blots demonstrating effects of UAG on phosphorylation of ERK1/2 and downstream target, p90RSK, after 24h treatment of MCF7 (FIG. 17B), MDA-MB-468 (FIG. 17C) and MDA-MB-231 cells (FIG. 17D).
Figure 17C:
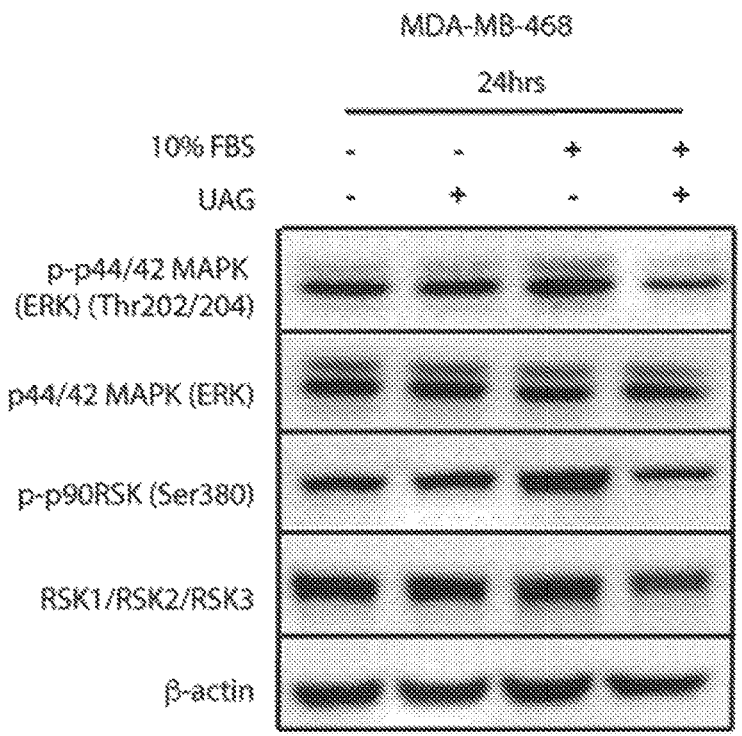
Figure 17D:
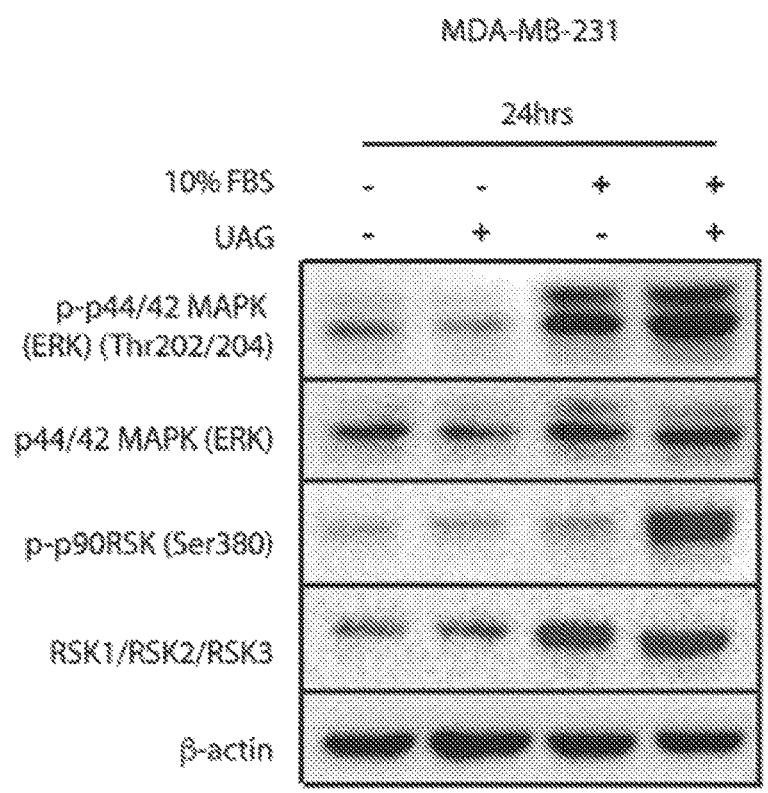
Figure 17E:
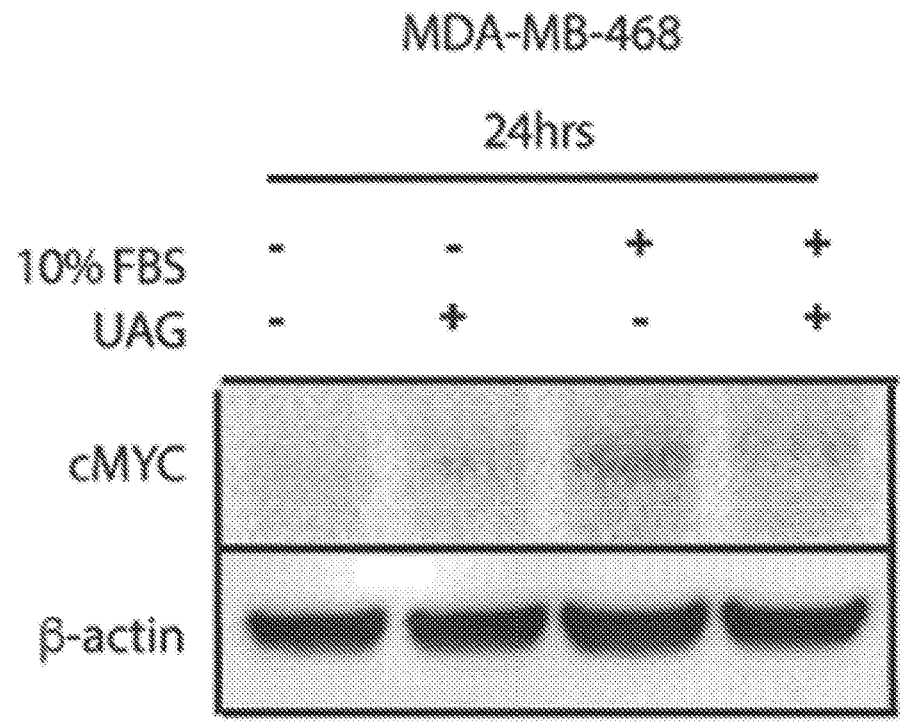
FIGS. 17E-17F show western blots demonstrating that UAG suppressed cMYC in MDA-MB-468 (FIG. 17E), but not in MDA-MB-231 cells (FIG. 17F).
Figure 17F:
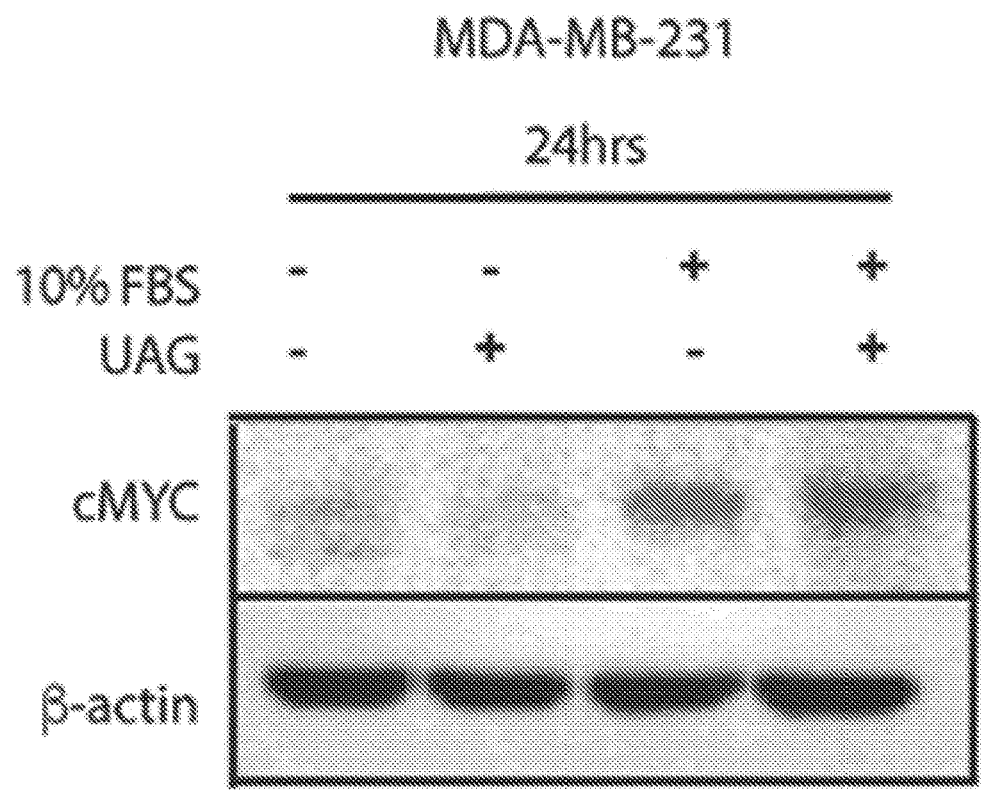
Figure 17G:
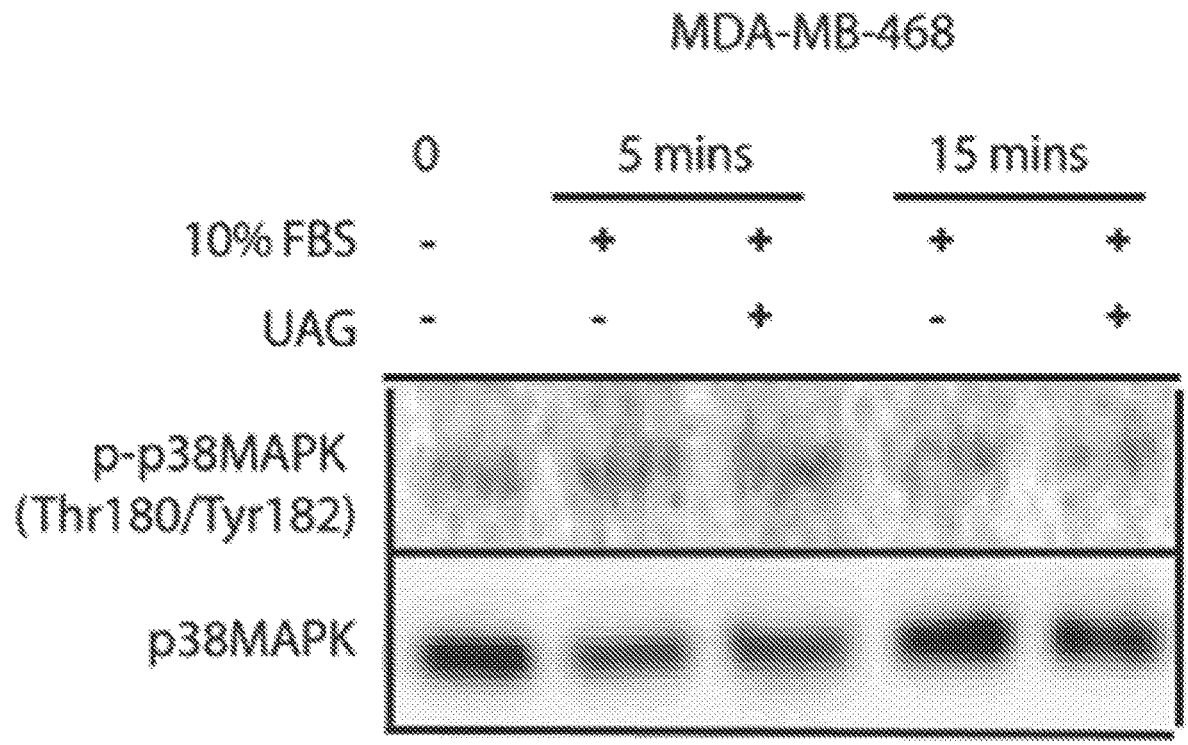
FIGS. 17G-17H show western blots demonstrating that UAG had no effect on phosphorylation of p38MAPK in MDA-MB-468 (FIG. 17G) and MDA-MB-231 (FIG. 17H).
Figure 17H:
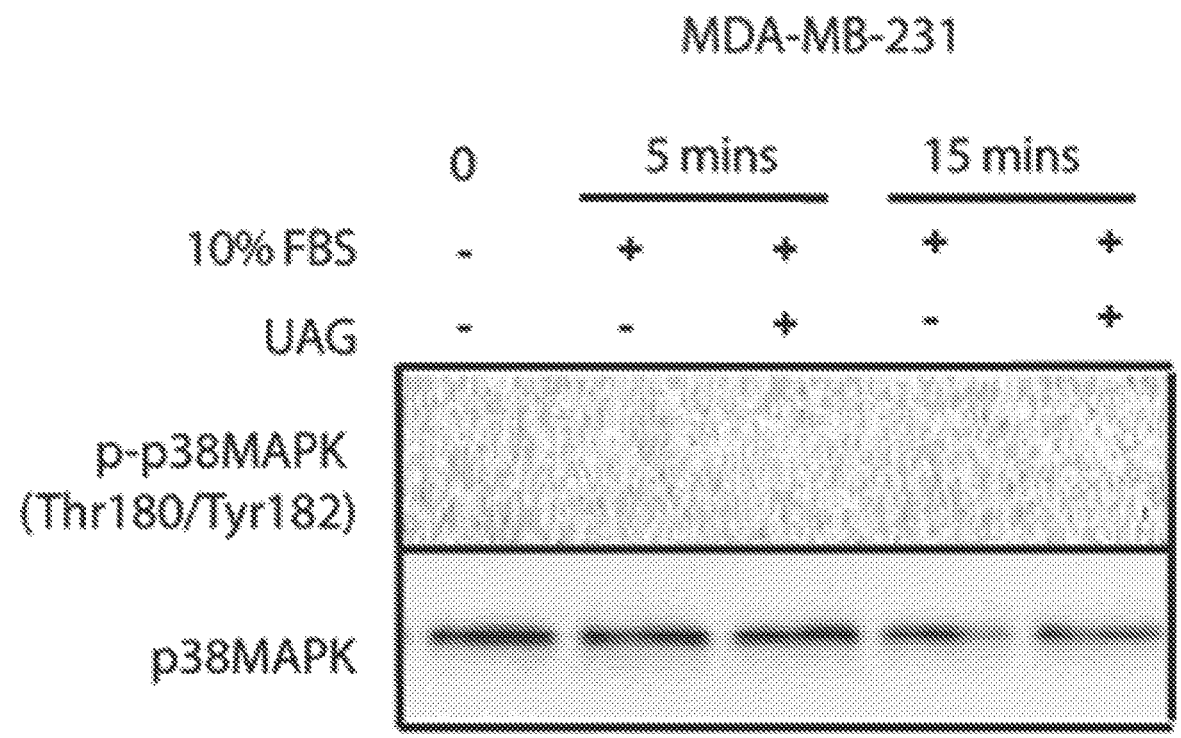
Figure 17I:
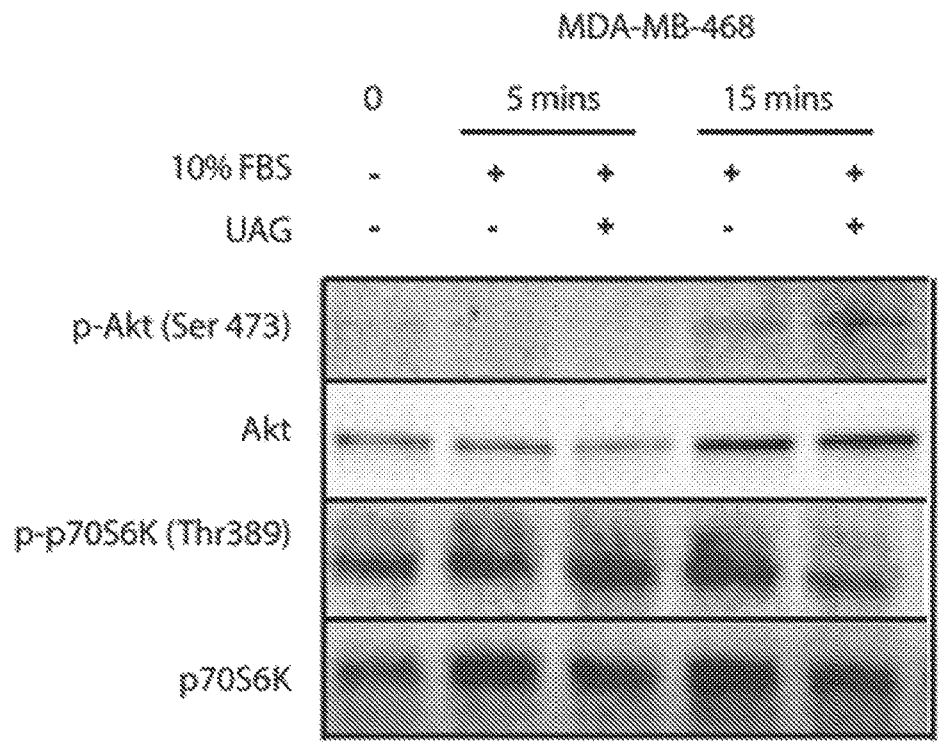
Figure 17J:
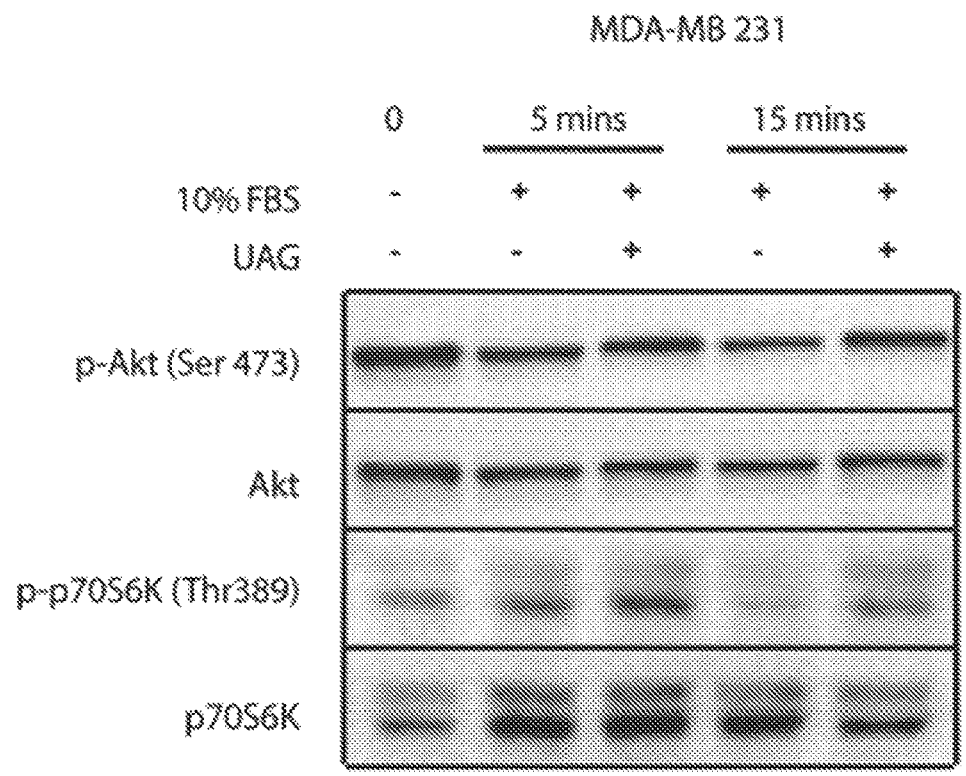
Figure 17K:
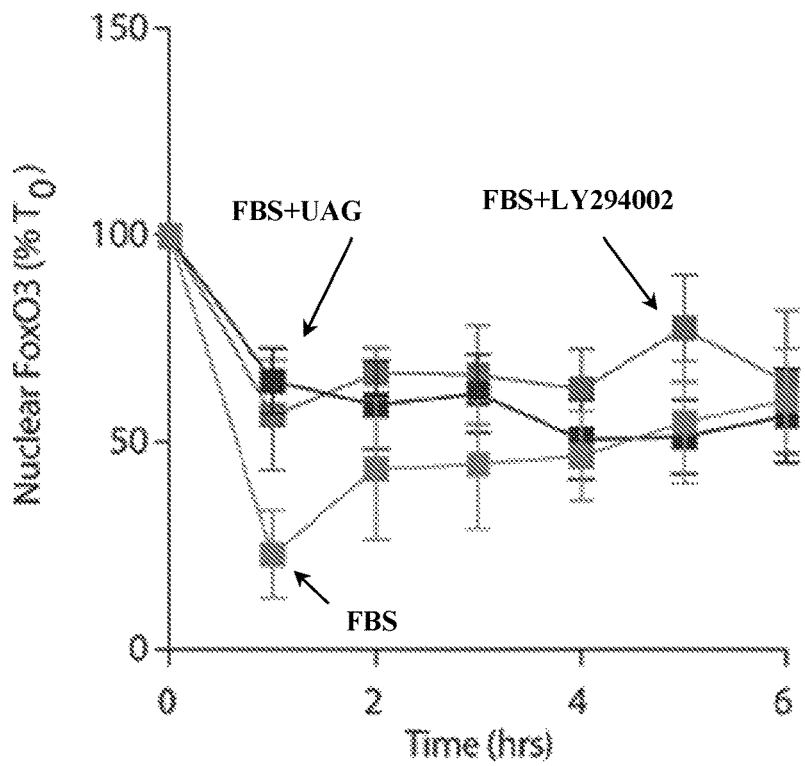
FIG. 17K shows the effect of UAG on FoxO3-RFP nuclear localization in MDA-MB-468 cells. Data represent mean±SEM with n≥3. Experiments were repeated at least twice. UAG: unacylated ghrelin; FBS: fetal bovine serum.
Figure 17L:
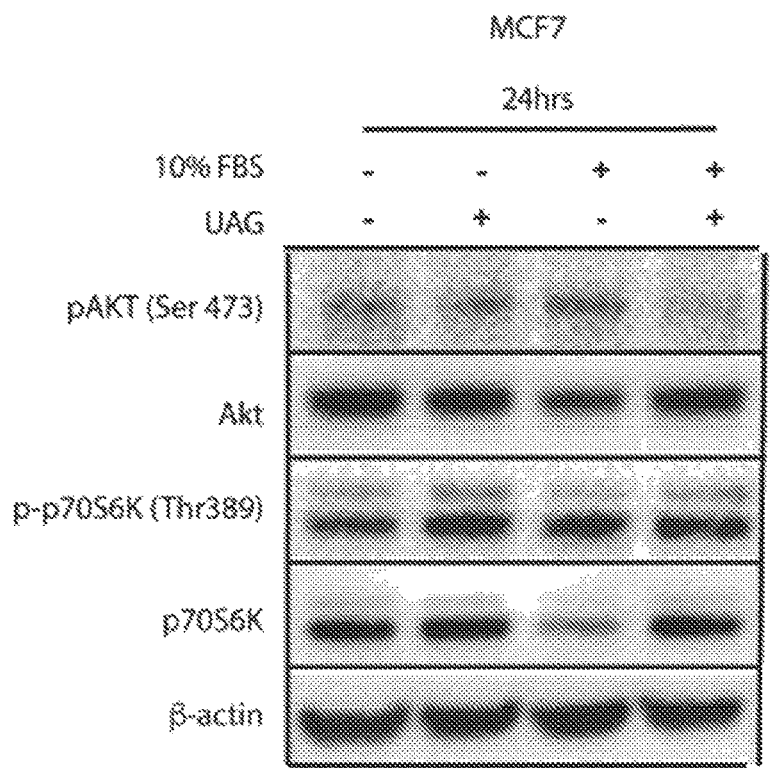
Figure 17M:
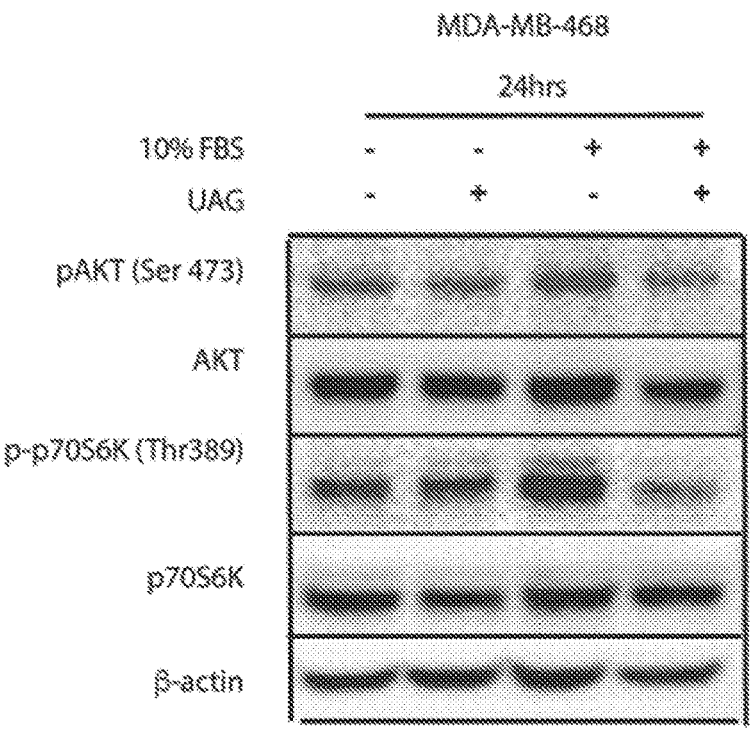
Figure 17N:
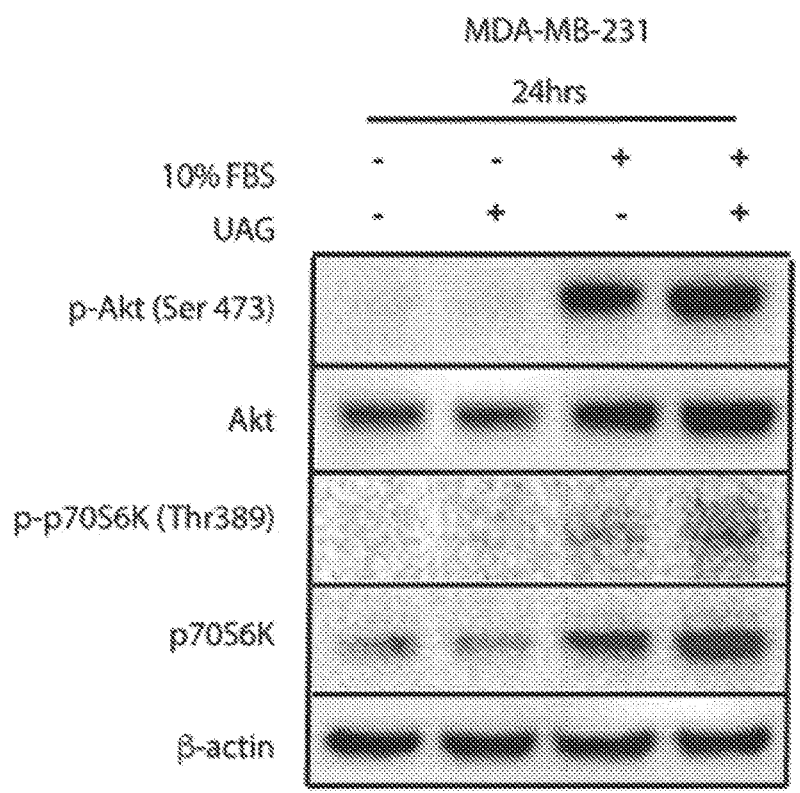

Effects of unacylated ghrelin on ERK activity were examined in 3D cultures in real-time using time-lapse confocal microscopy of the FRET-based extracellular signal-regulated kinase activity reporter (EKAR) in MCF7, MDA-MB-468 and MDA-MB-231 cells (FIGS. 9A-9B and 17A). As shown in FIG. 9A, serum stimulated EKAR activity, whereas unacylated ghrelin and the MEK inhibitor, U0126, inhibited this effect. Effects of unacylated ghrelin on MAPK signaling were then examined. As shown in FIG. 9B, unacylated ghrelin caused a rapid decrease in the phosphorylation of ERK and downstream target, $p90^{RSK}$. The effect on $p90^{RSK}$ was sustained for 24 hrs in MCF7 and MDA-MB-468 cells, but this suppression was not observed in MDA-MB-231 cells, at any time point (FIGS. 17B, 17C, 17D, 17I, 17J, and 17L-17N). As shown in FIGS. 9C, and 17E-17F, the levels of MAPK target cMyc, induced by serum, were also suppressed in cells treated with unacylated ghrelin. No effect on p38 MAPK was observed (FIGS. 9D, and 17G-17II). Effects on Akt phosphorylation and activity were then examined by immunoblotting and by quantifying levels of FoxO3 nuclear localization. As shown in FIG. 9E, unacylated ghrelin inhibited the serum-stimulated phosphorylation of Akt (Ser473) and downstream target p70S6K (Thr389). Consistently, as shown in FIGS. 9F, and 17K, it also prevented the serum-mediated exclusion of FoxO3 from the nucleus.

Example 5: Unacylated Ghrelin Causes Cell Cycle Arrest and Apoptosis

Figure 3A:
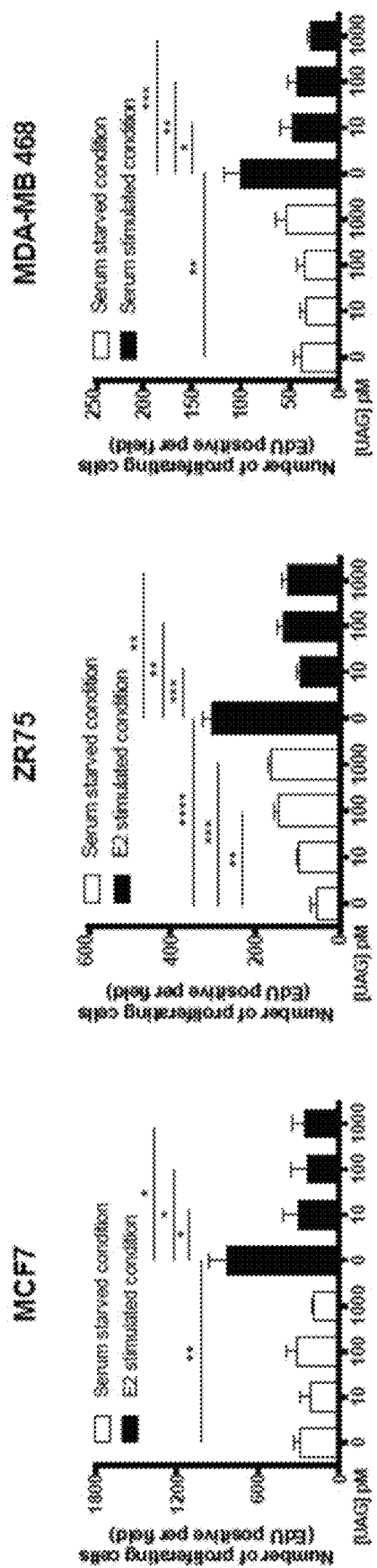
FIGS. 3A-3B show that des-acyl ghrelin inhibited breast cancer cells via effects on cell proliferation, cell cycle, apoptosis and migration.
Figure 3B:
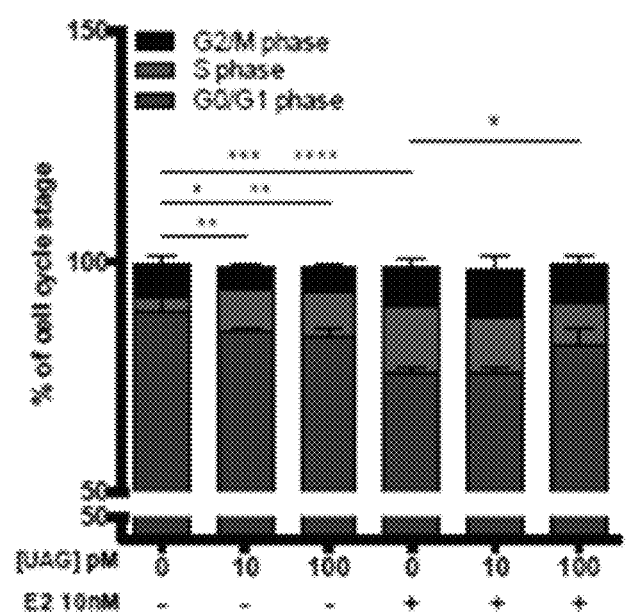
Figure 3B:
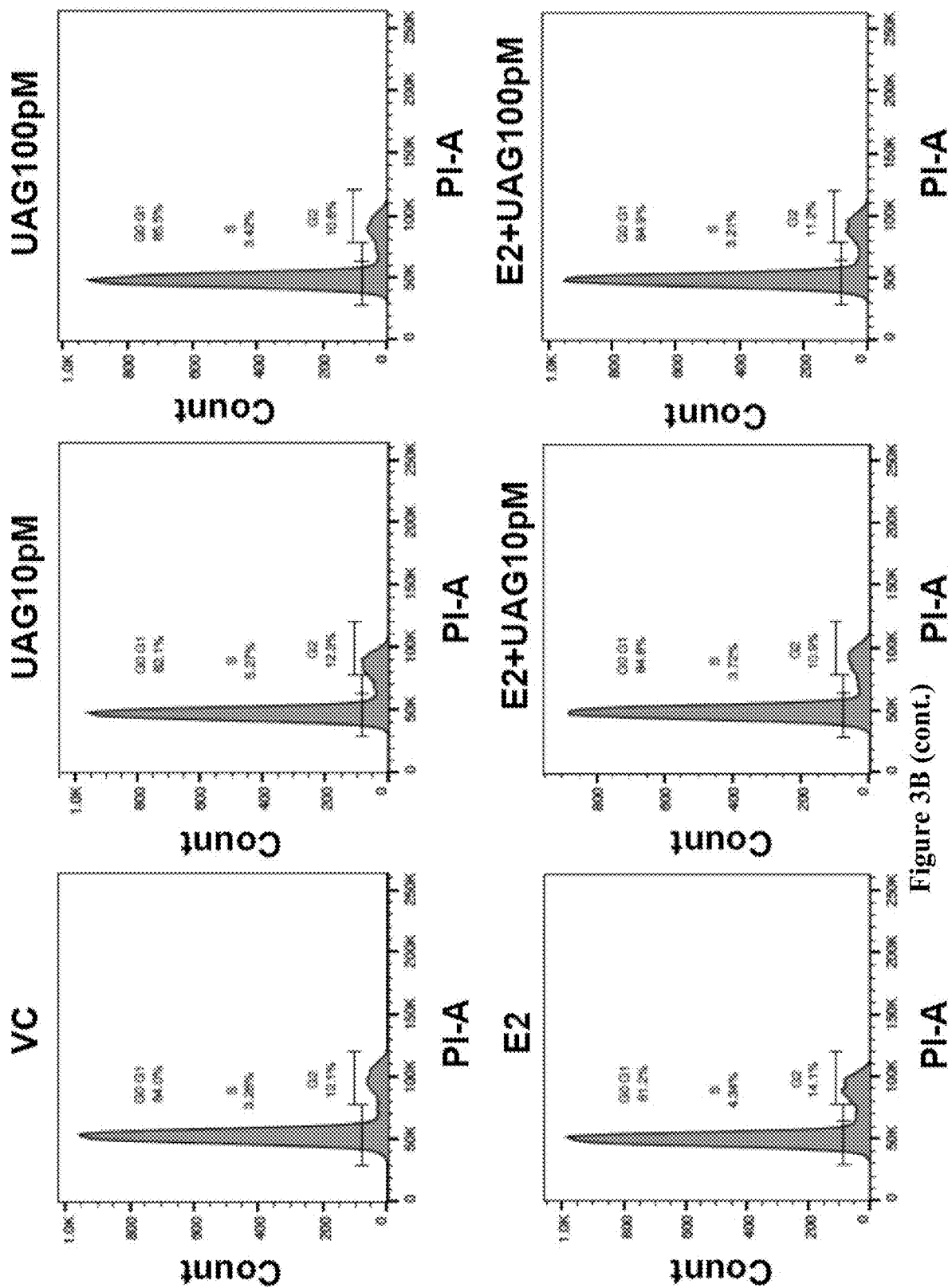
Figure 3C:
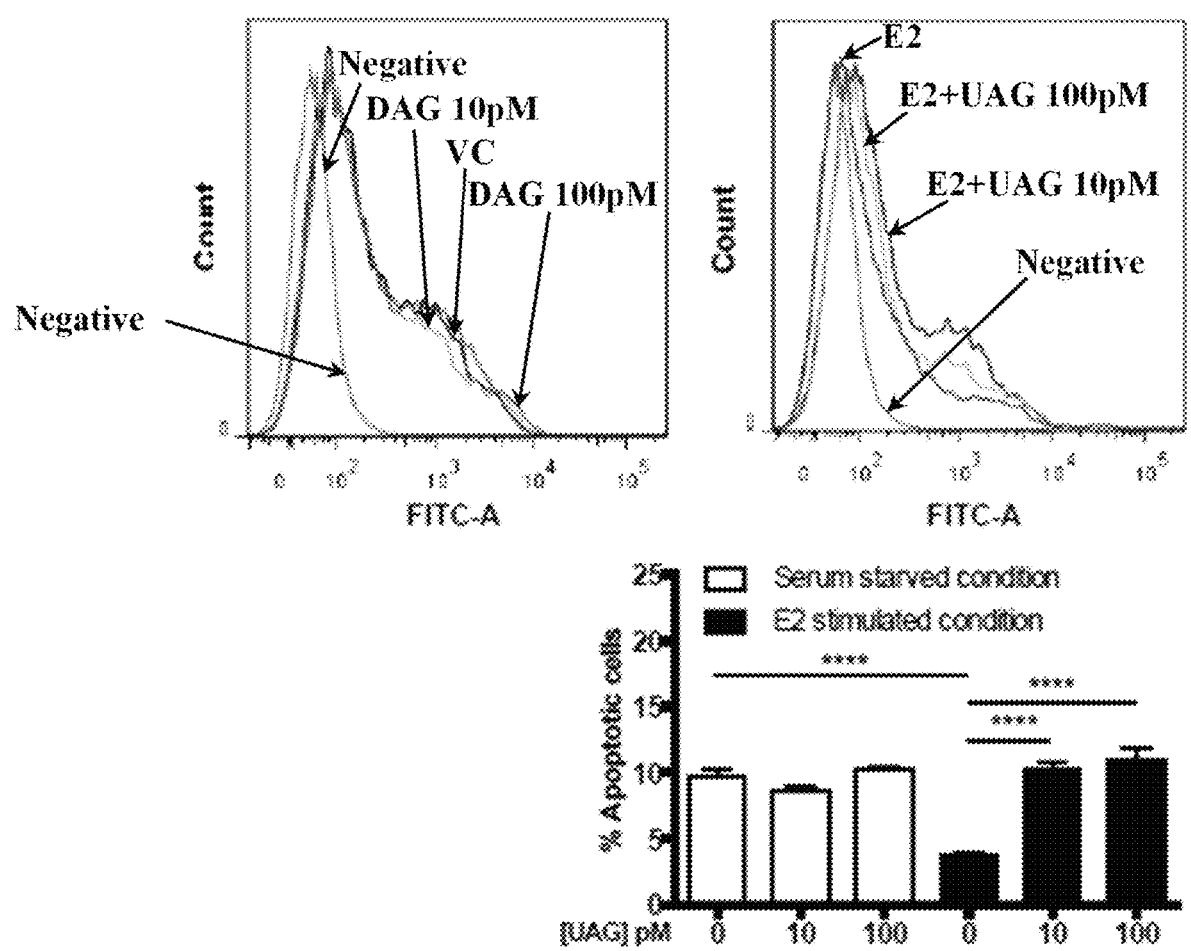
Figure 3D:
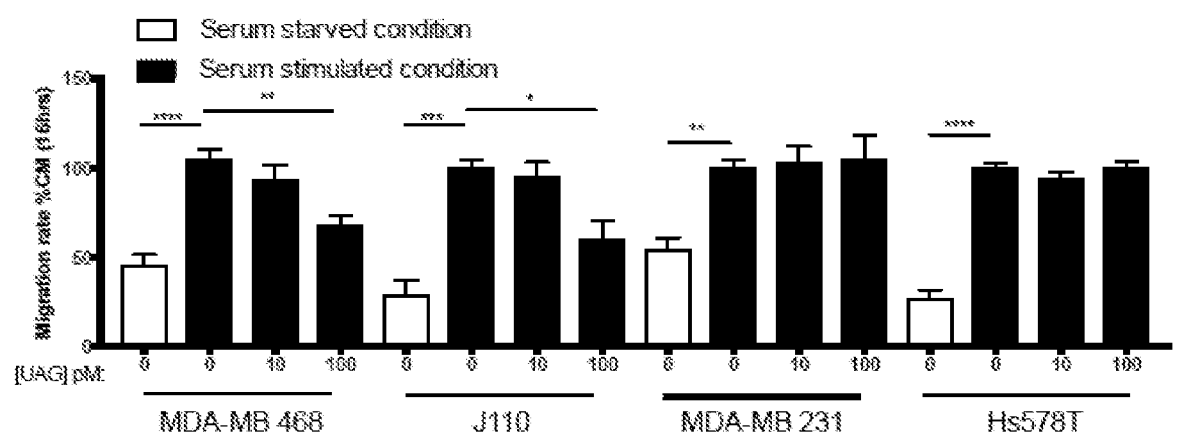
FIG. 3D shows that des-acyl ghrelin significantly inhibited the migration of all breast cancer subtypes except the cells carrying RAS/RAF mutations. UAG: des-acyl ghrelin; E2: estradiol; FSK: forskolin; VC: vehicle control.
Figure 10A:
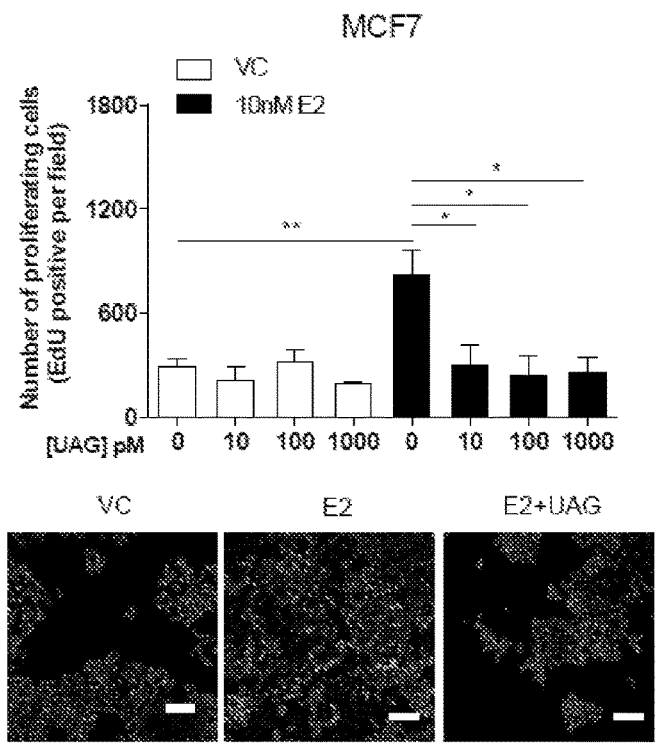
FIGS. 10A-10H show that unacylated ghrelin (UAG) caused cell cycle arrest and apoptosis.
Figure 10B:
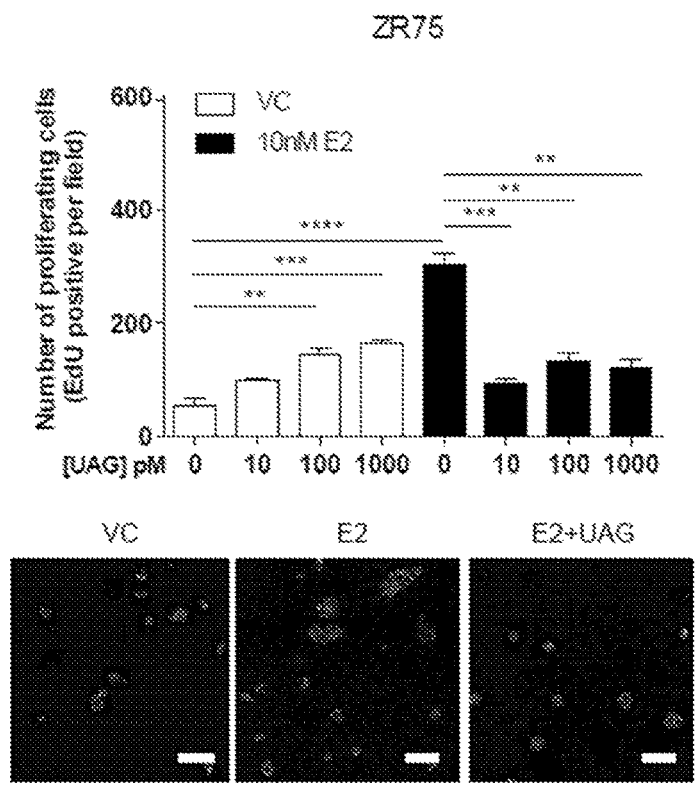
Figure 10C:
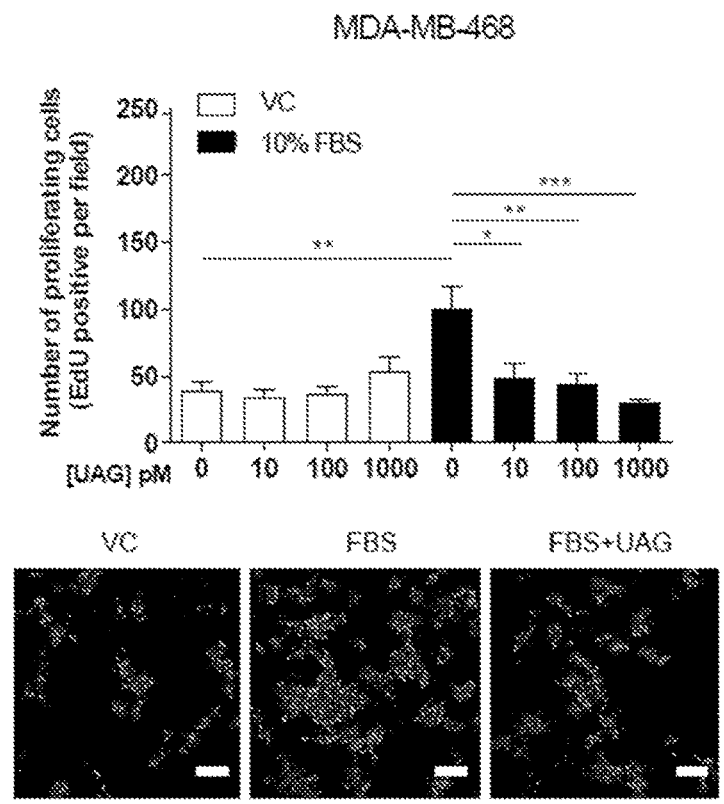
Figure 10D:
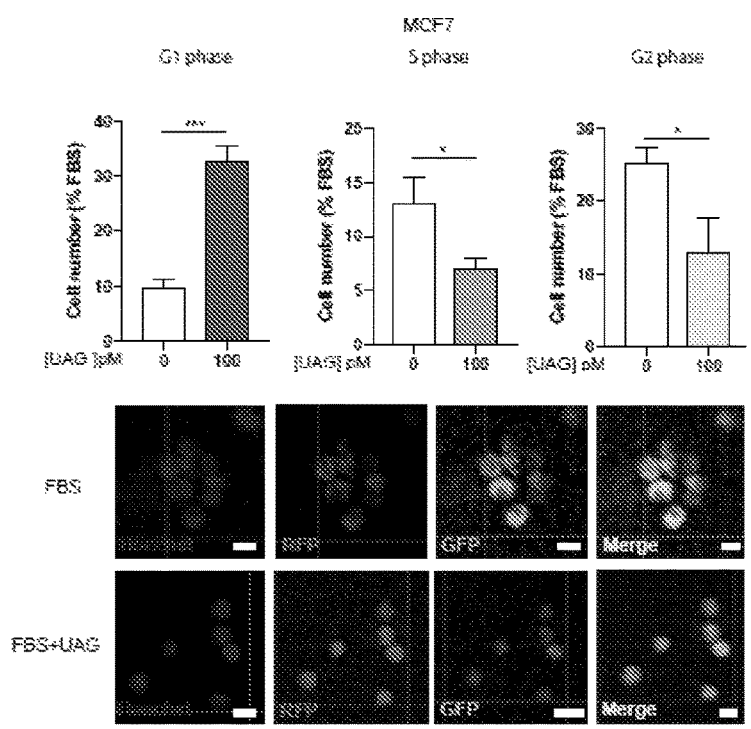
Figure 10E:
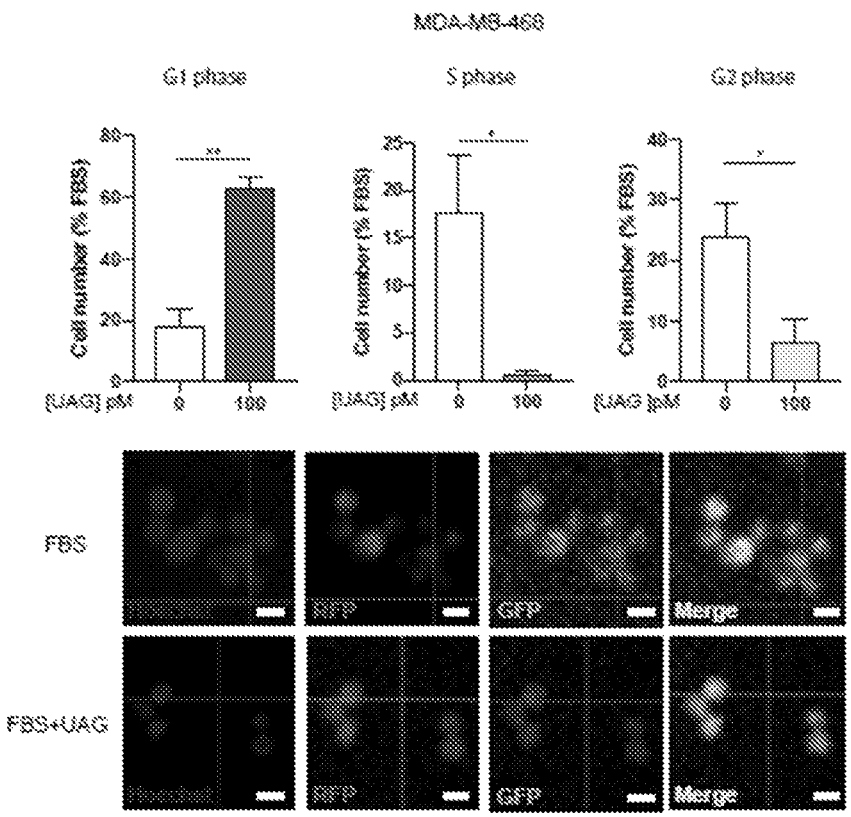
Figure 10F:
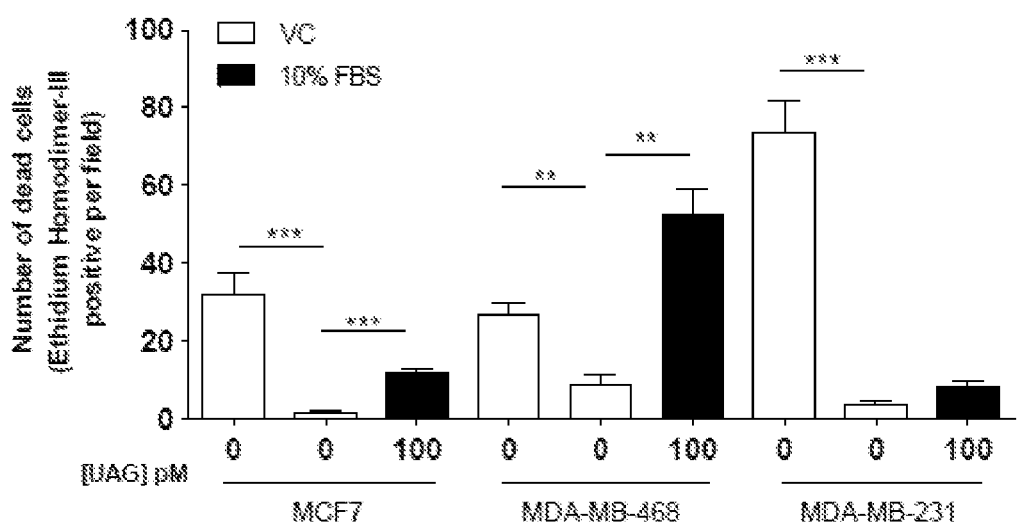
Figure 10G:
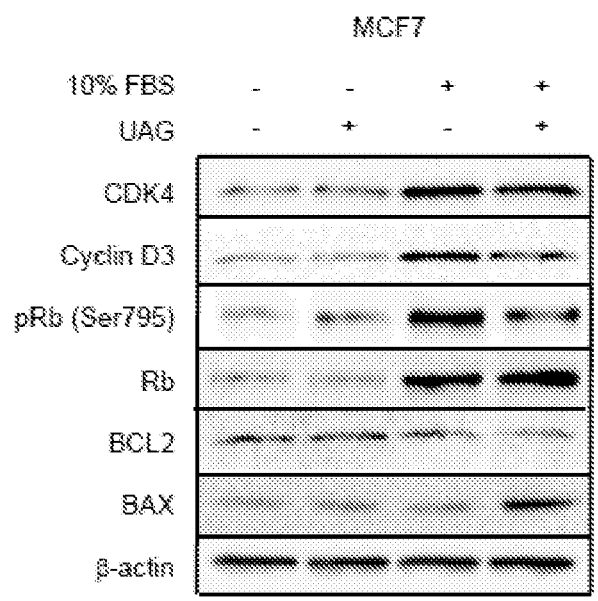
Figure 10H:
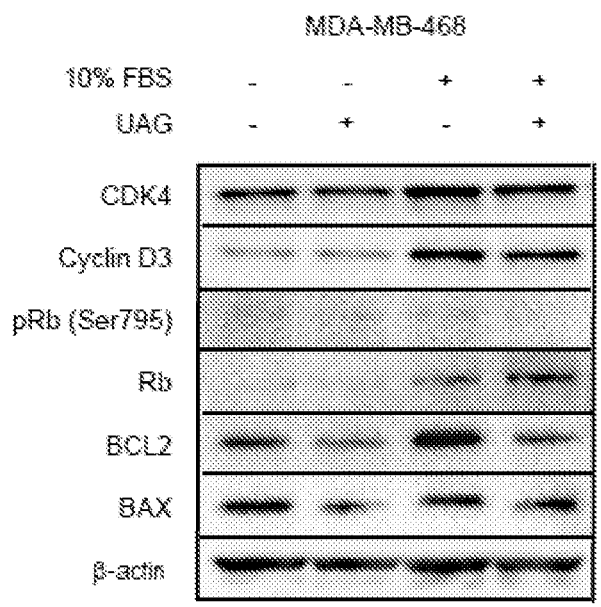
Figure 18A:
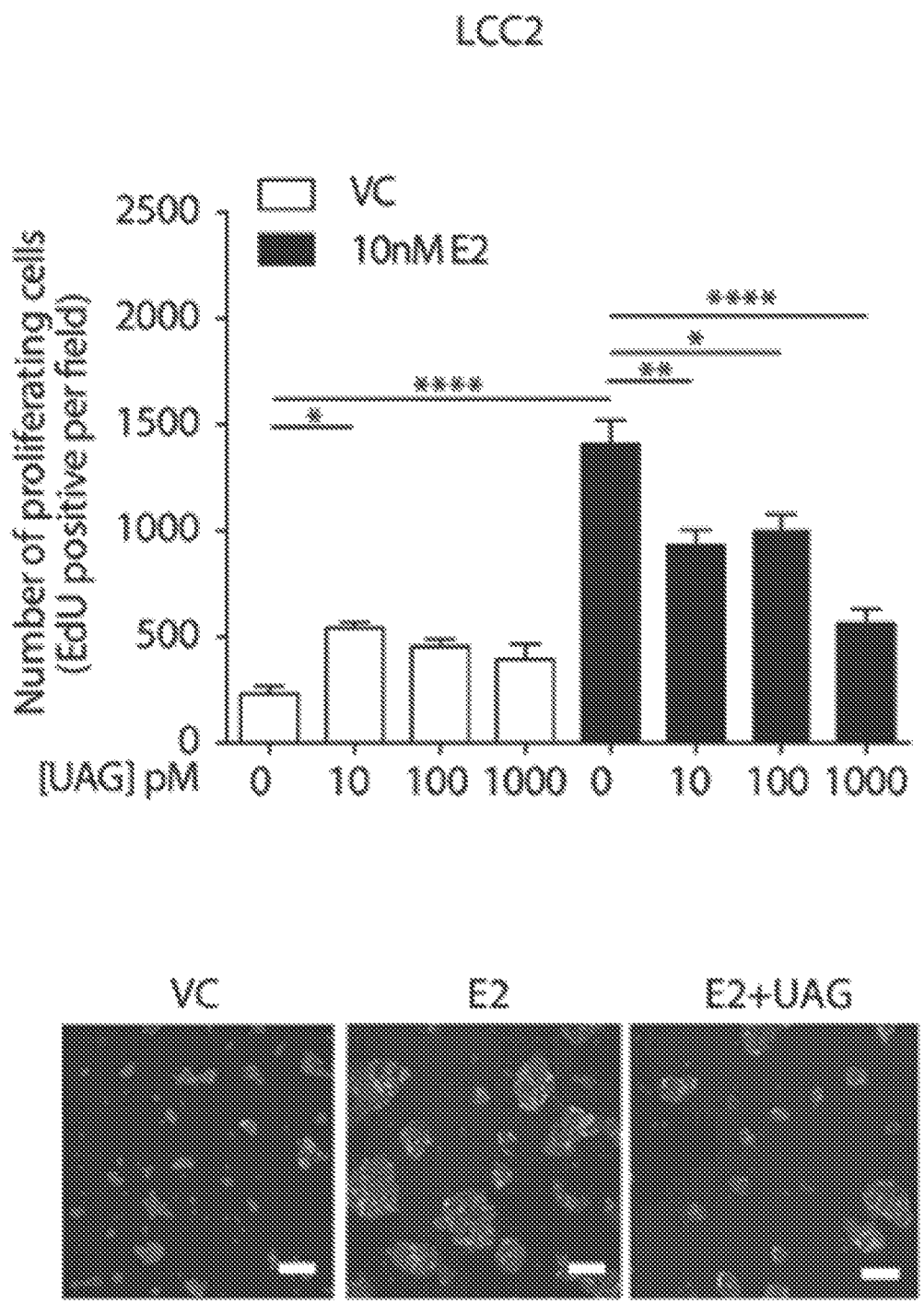
FIGS. 18A-18I shows that unacylated ghrelin (UAG) causes cell cycle arrest and apoptosis.
Figure 18B:
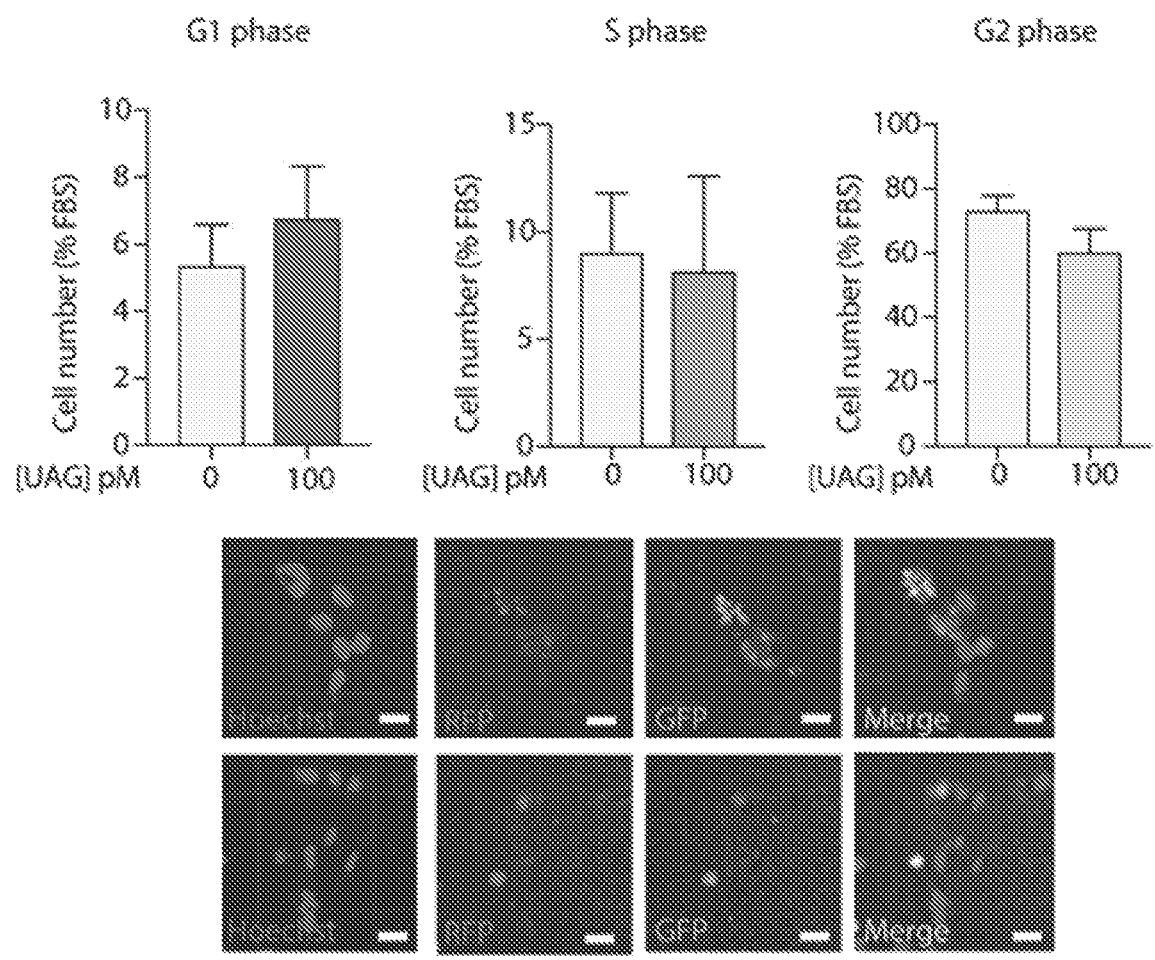
Figure 18C:
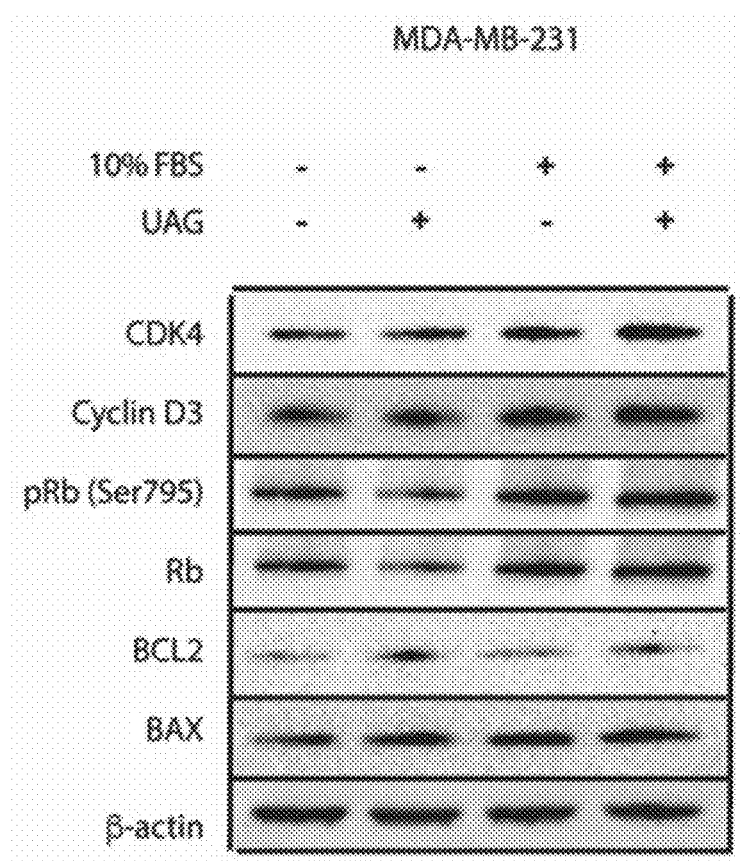
Figure 18D:
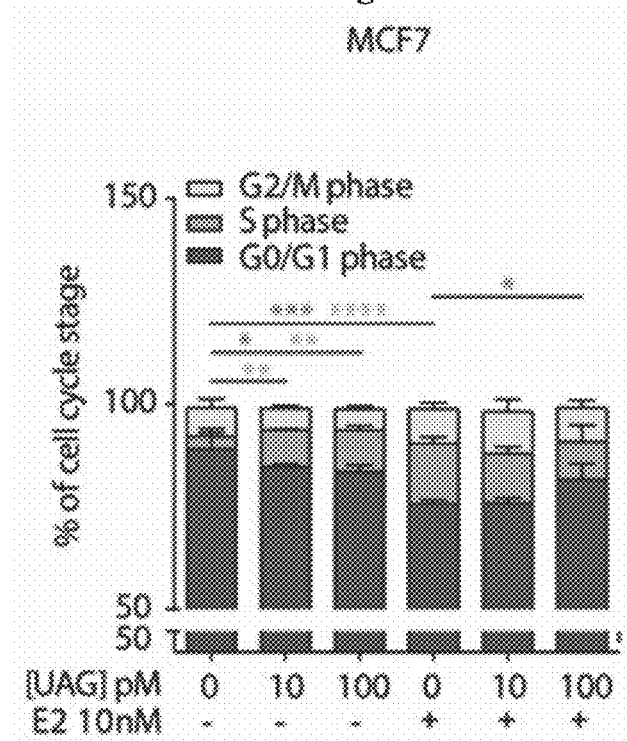
Figure 18D:
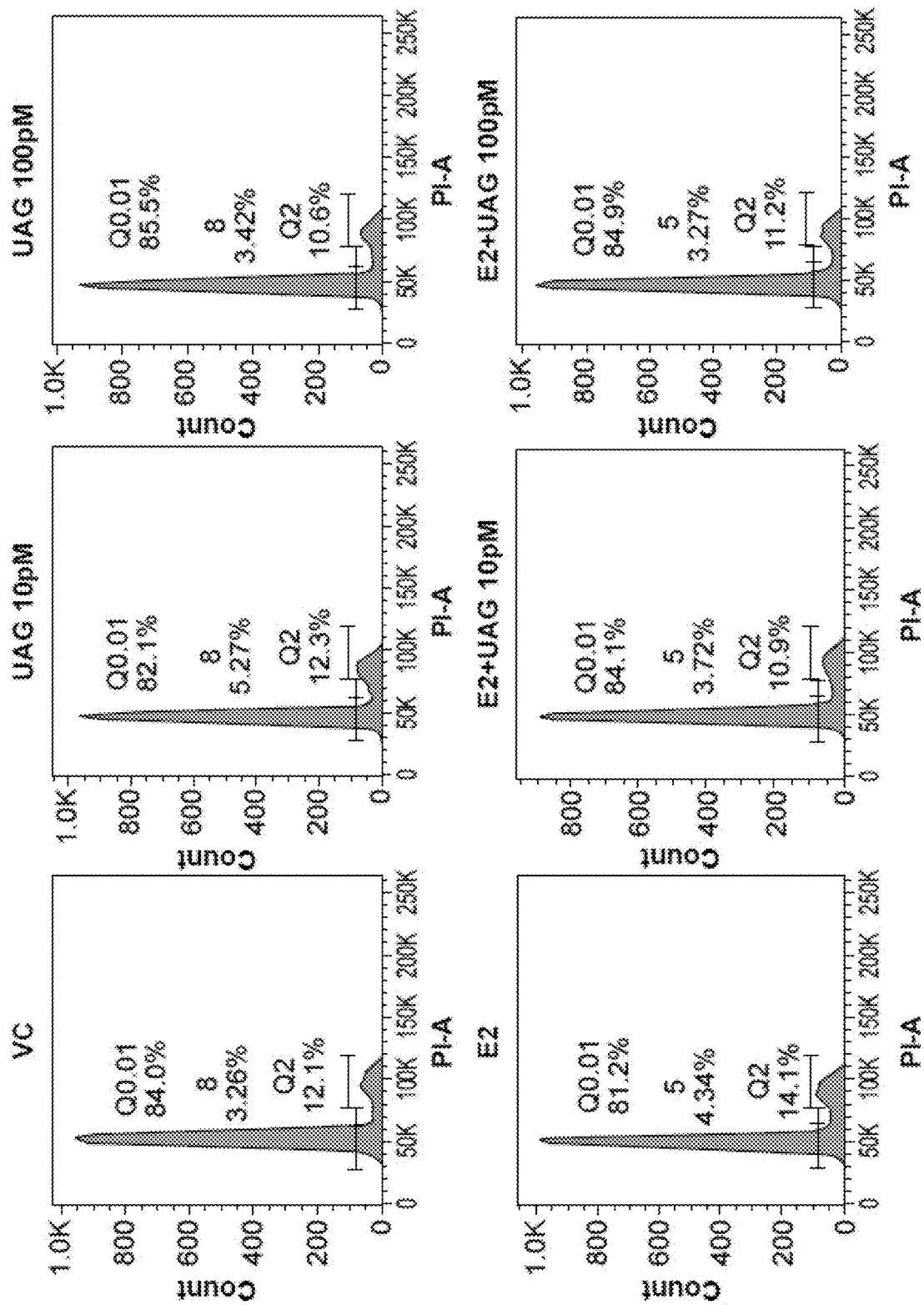
Figure 18E:
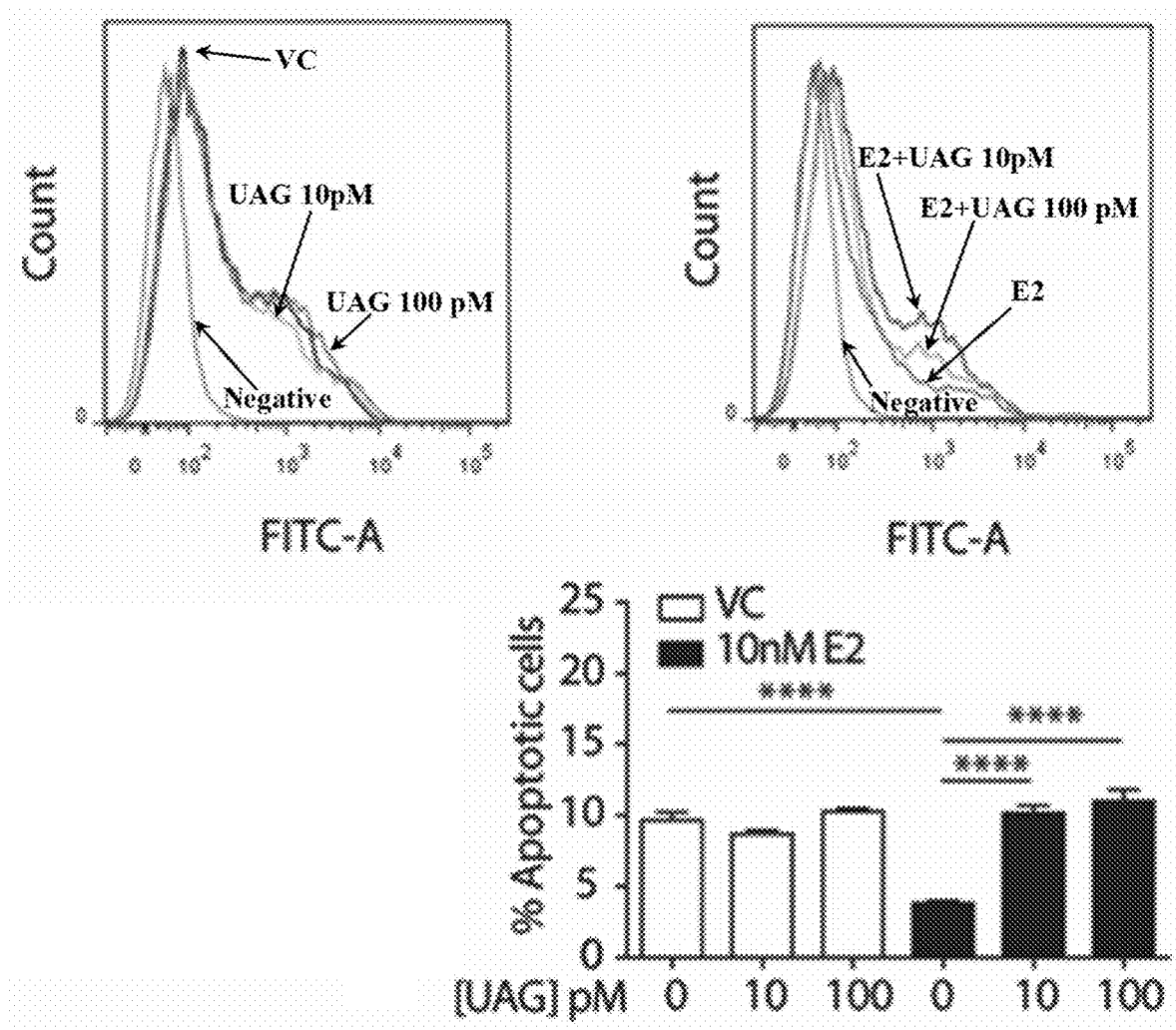
Figure 18F:
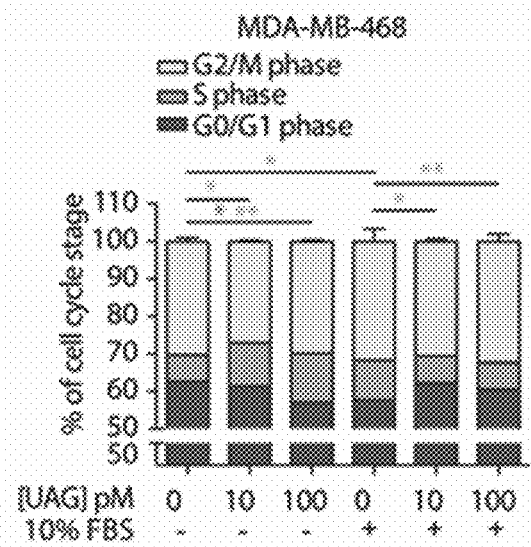
Figure 18F:
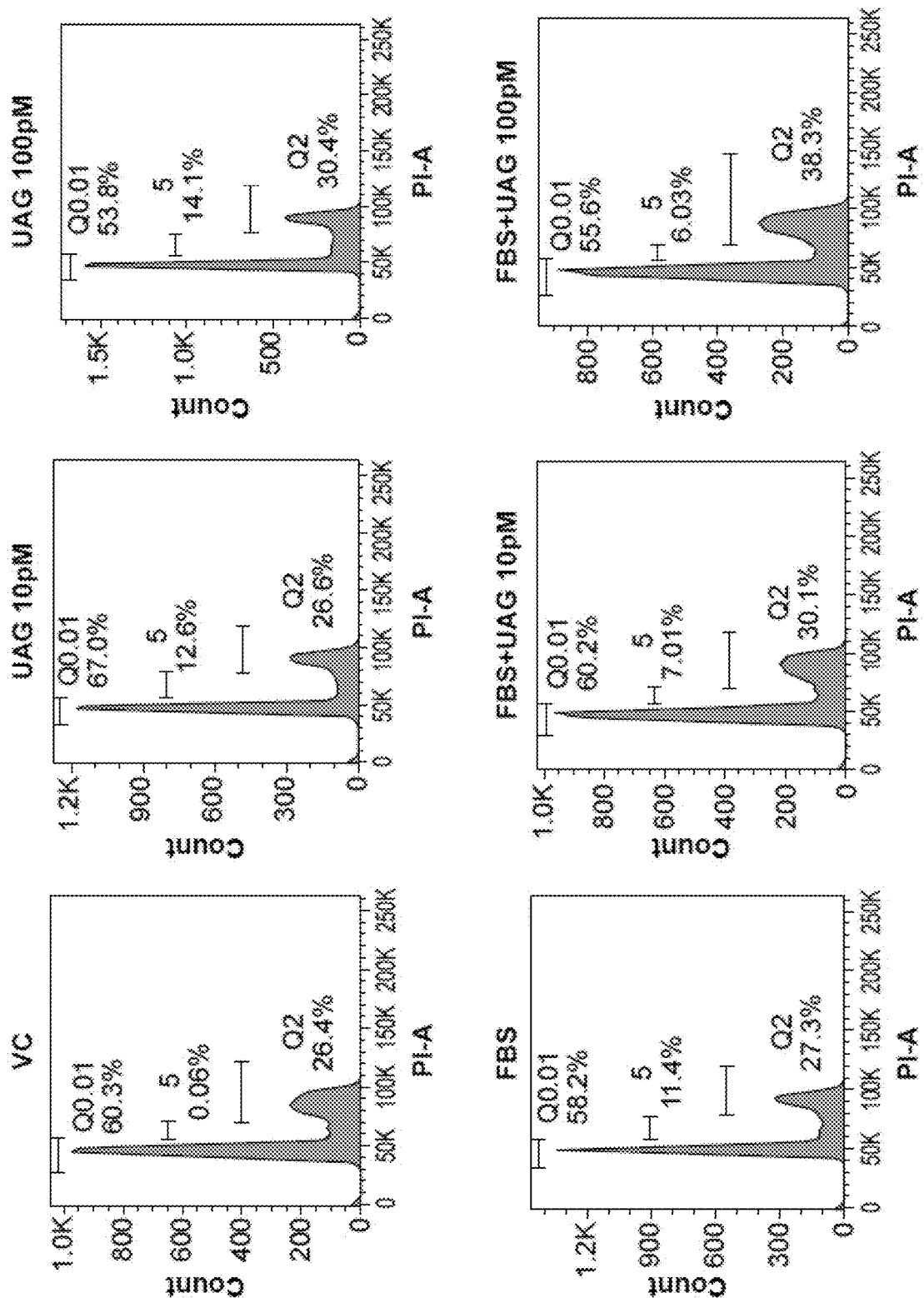
Figure 18G:
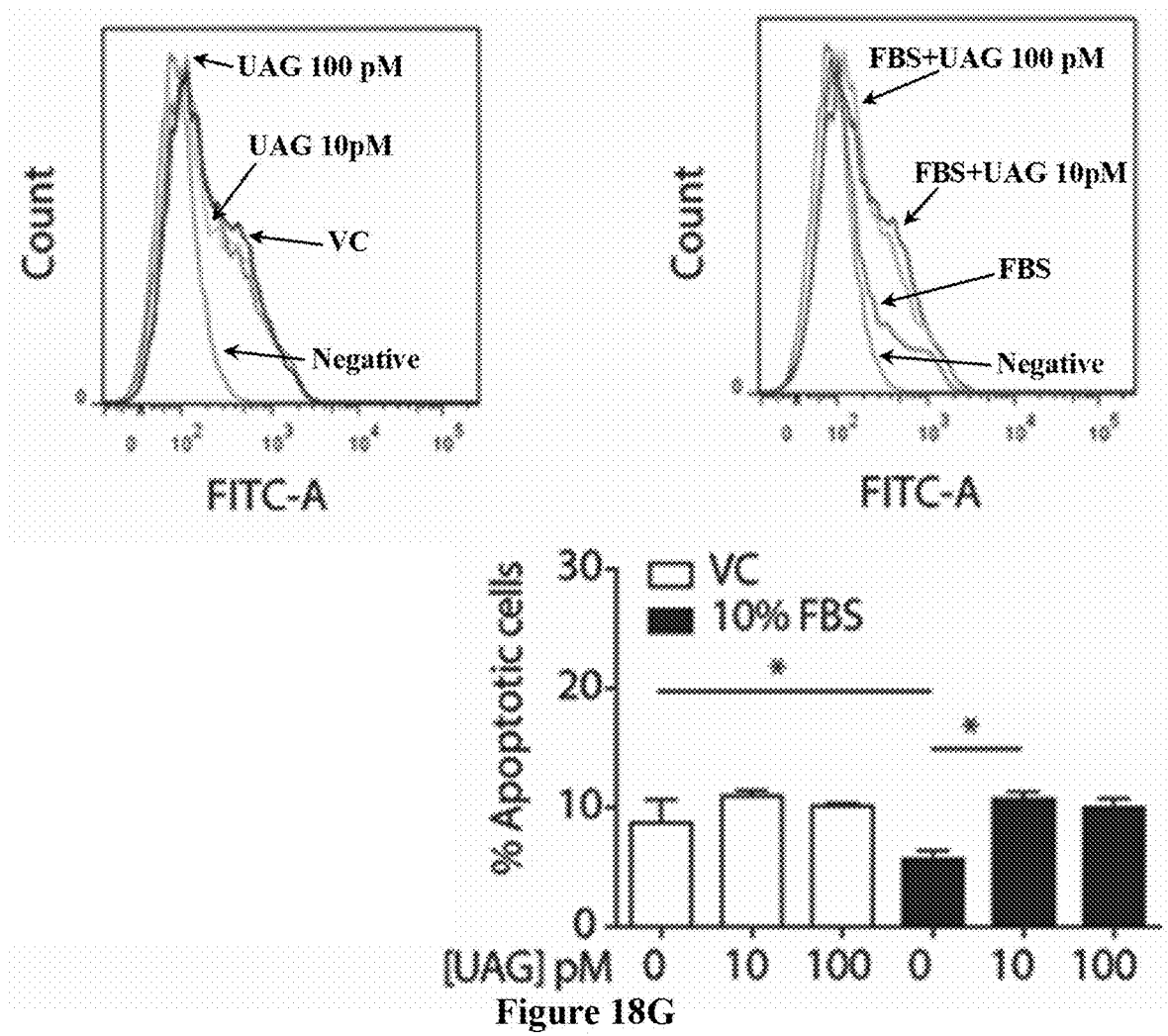
Figure 18H:
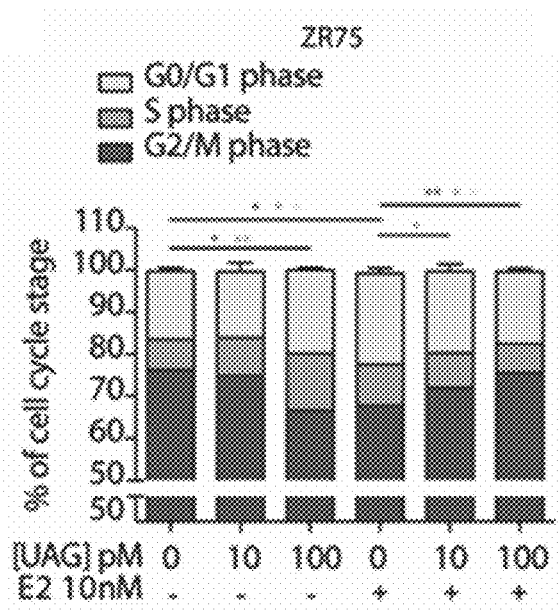
Figure 18H:
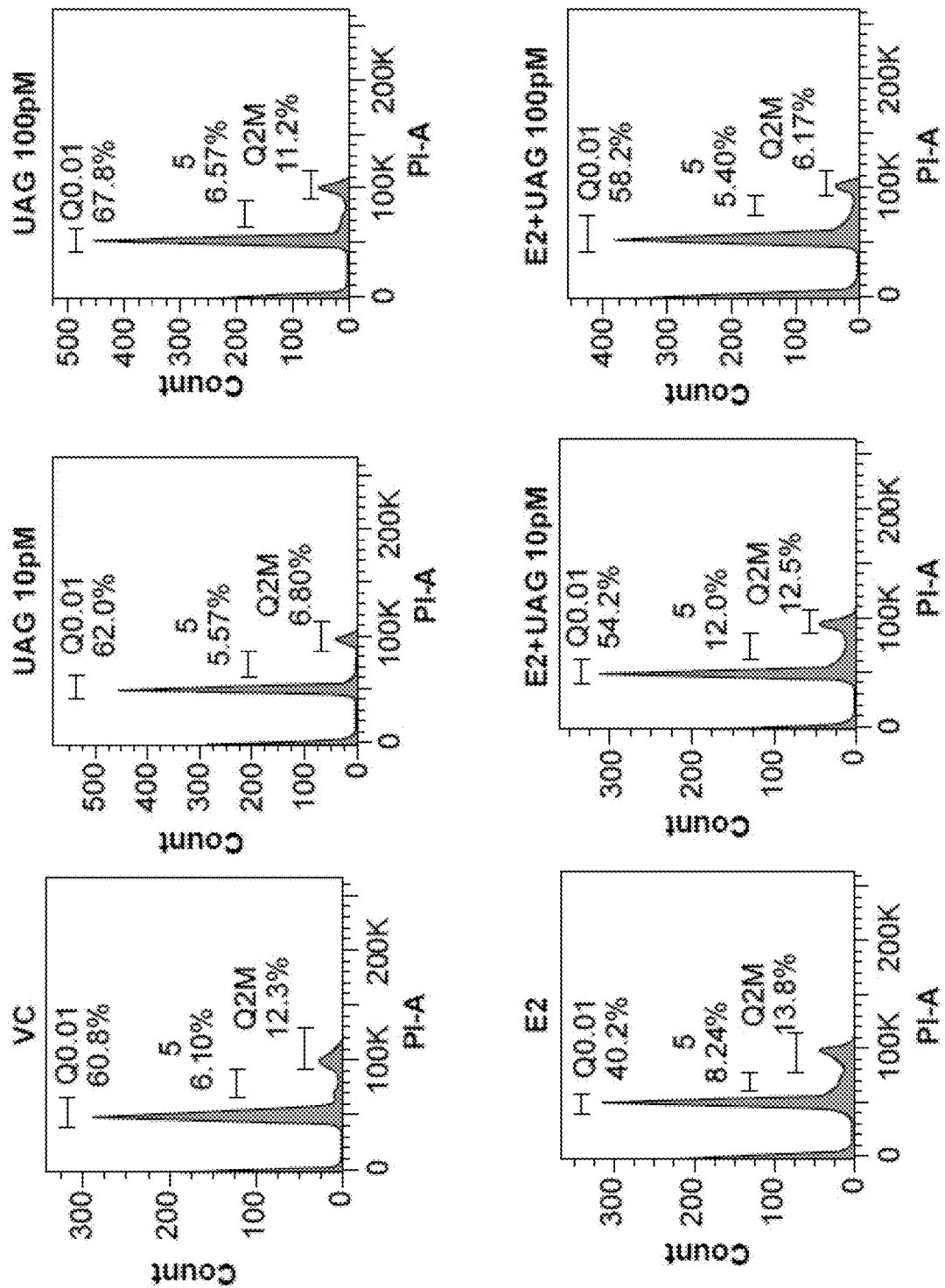
Figure 18I:
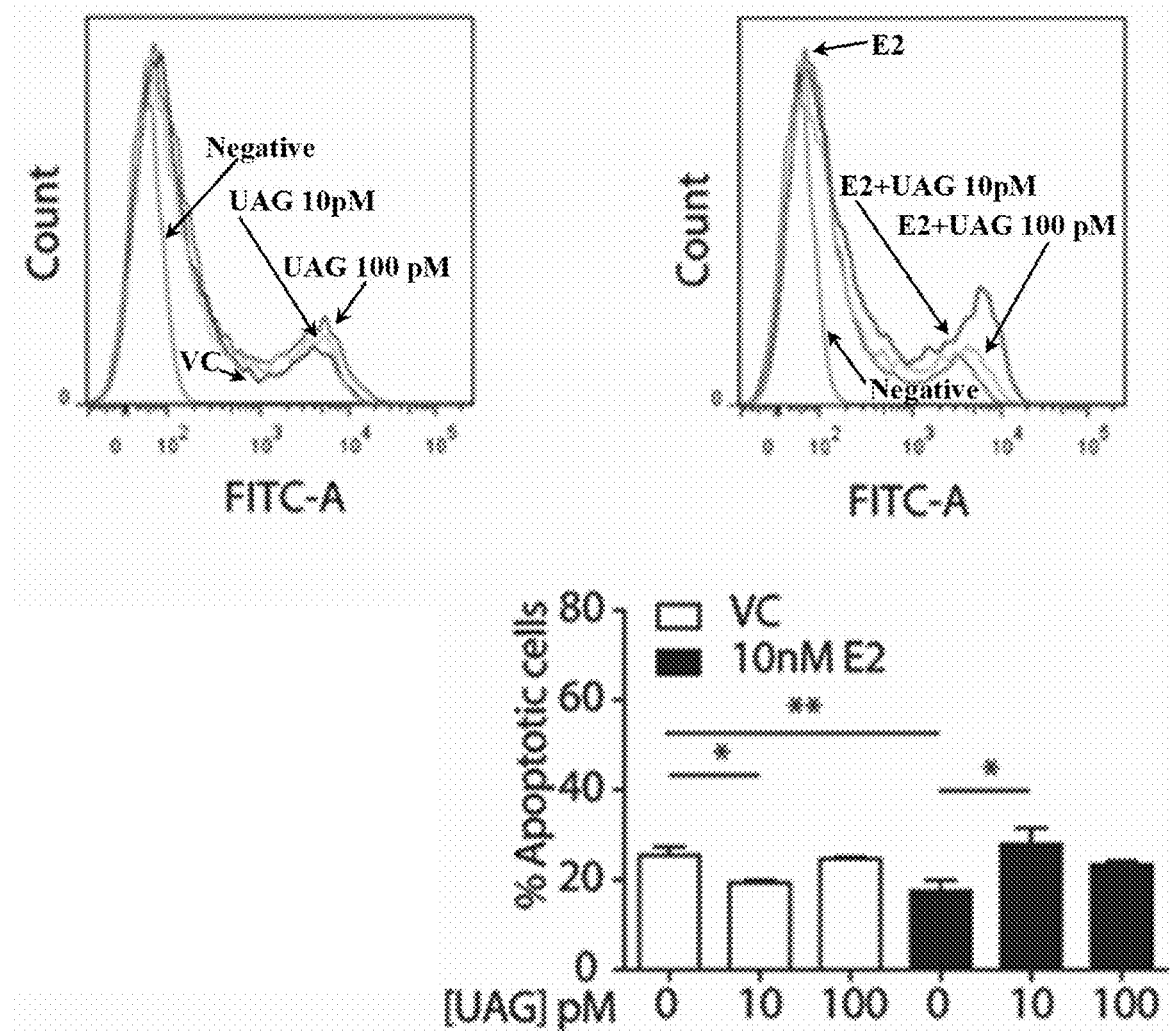

The effects of unacylated ghrelin on cell proliferation were examined by assessing EdU incorporation in breast cancer cell lines grown in 3D. As shown in FIGS. 3A, 10A, 18A, estradiol and serum caused a significant increase in EdU incorporation and unacylated ghrelin suppressed DNA synthesis at 10, 100 and 1000 pM. The effect of unacylated ghrelin on cell cycle was assessed in breast cancer cell lines in 3D using the Premo FUCCI Cell Cycle Sensor. As shown in FIGS. 10A-10C, 10E and 18B, suppression of EdU incorporation was associated with an increase in cells arrested at the G1 phase in MCF7 and MDA-MB-468 cells, with no significant effect in MDA-MB-231 cells (see also FIGS. 18D, 18F and 18H). Unacylated ghrelin also caused apoptosis in serum-stimulated MCF7 and MDA-MB-468 cells, measured in 3D and using FACS analysis of Annexin V-stained cells (FIGS. 3B, 3C, 10D, 10F and 18E, 18G and 18I). Consistently, as shown in FIGS. 10G-10H unacylated ghrelin suppressed the serum-stimulated expression of CDK4, cyclin D3, BCL2 and the phosphorylation of Rb at Ser795, while stimulating the expression of BAX. This effect was not observed in MDA-MB-231 cells (FIG. 18C). As shown in FIG. 3D, des-acyl ghrelin significantly inhibited the migration of all breast cancer subtypes except the cells carrying RAS/RAF mutations.

Figure 4A:
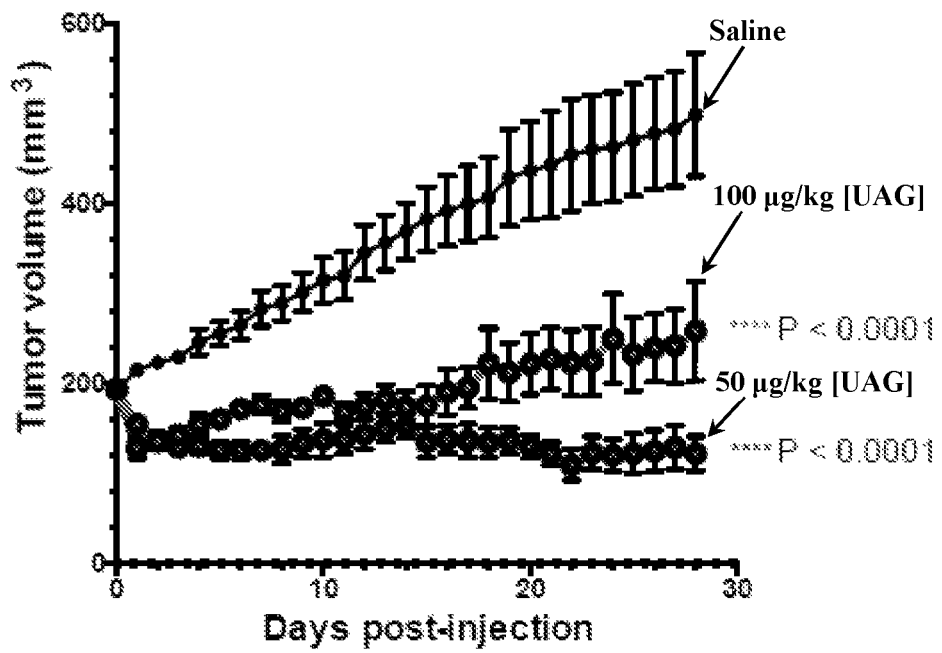
Figure 4B:
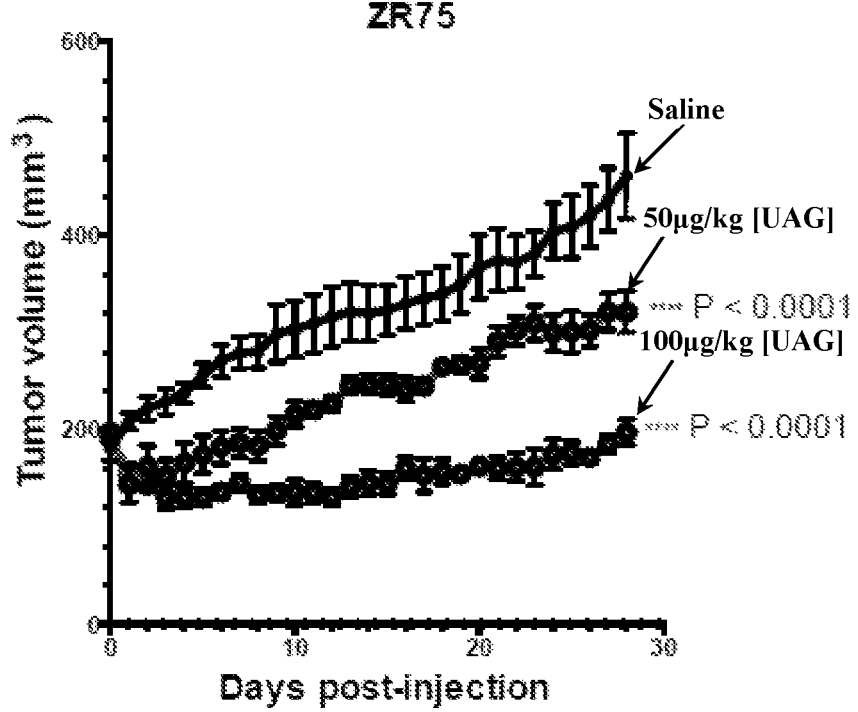
Figure 4C:
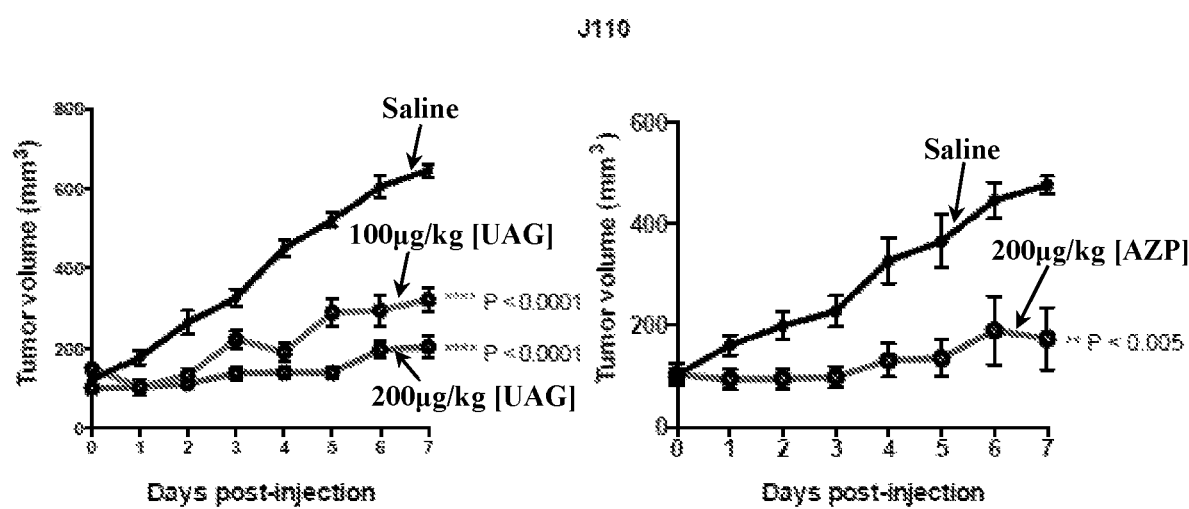
FIG. 4C shows the tumor volume in response to treatment with 100 mg/kg or 200 mg/kg des-acyl ghrelin (UAG) in mice allografted with J110 cells (FVB mice).
Figure 4D:
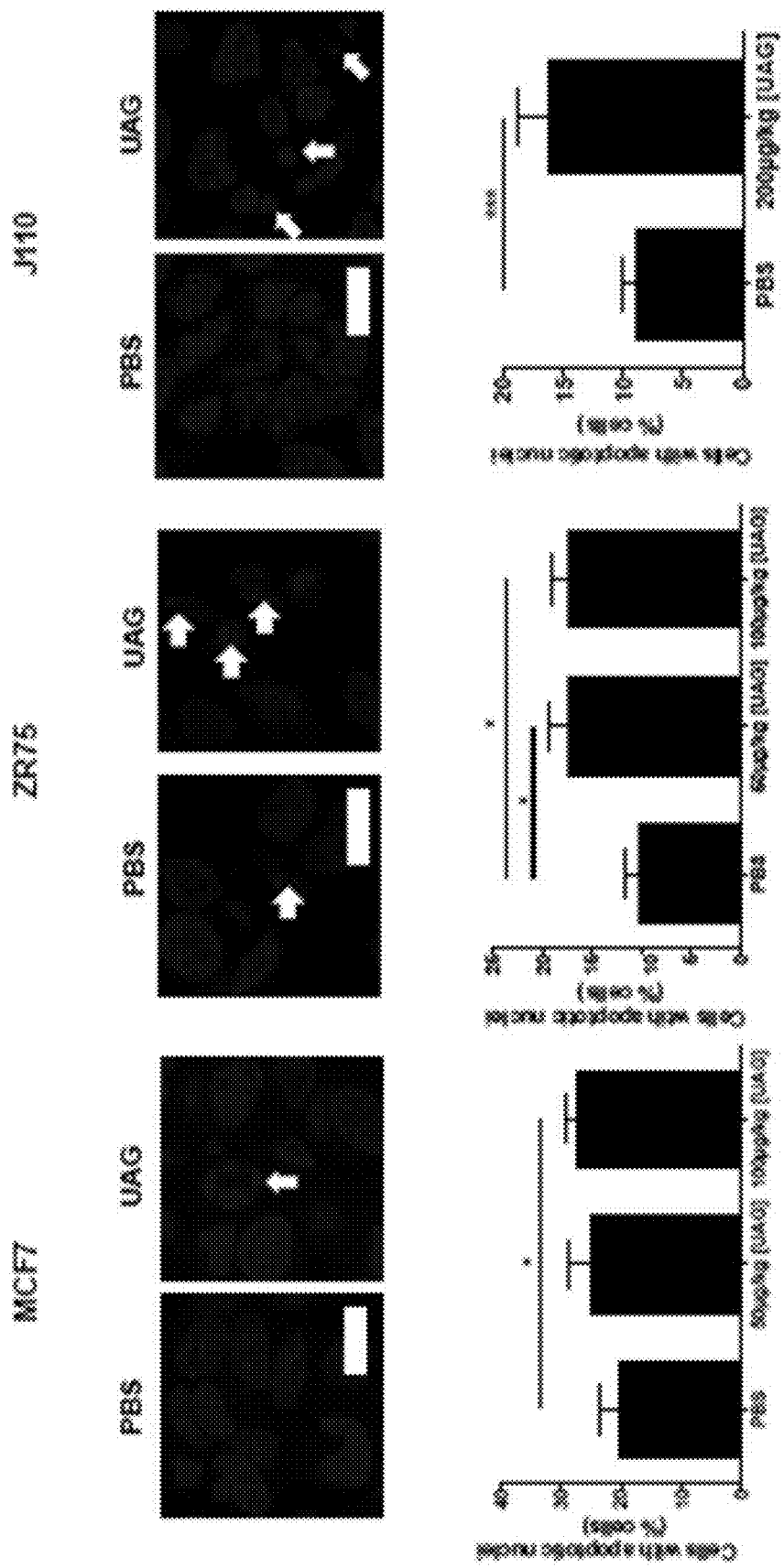
FIG. 4D shows the changes in nuclear morphology in MCF7, ZR75 and J110 tumor cells post-treatment with UAG. White arrows indicate apoptotic nuclei defined as having fragmented or condensed chromatin. Scale bars (10 μm). Percentage of MCF7, ZR75 and J110 cells with apoptotic nuclei are shown in the bottom panel.
Figure 4E:
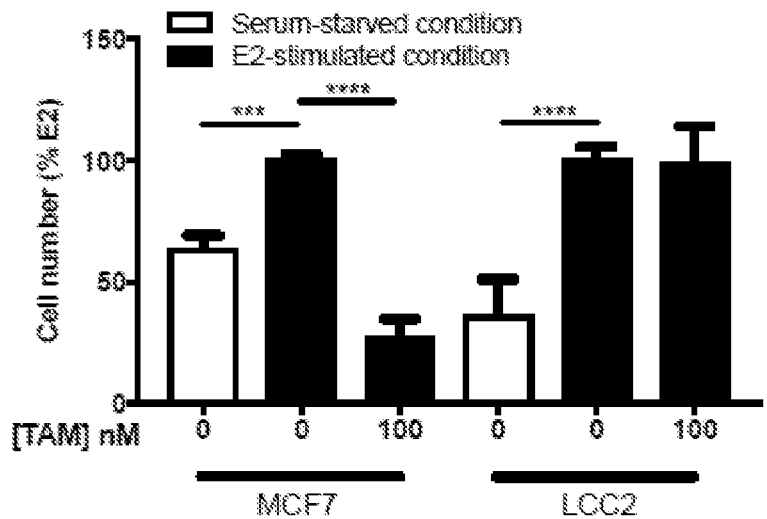
FIG. 4E shows the effect of tamoxifen on growth of MCF7 and tamoxifen-resistant breast cancer cells (LCC2). MCF7 and LCC2 cells were treated with 100 nM tamoxifen under basal conditions and under E2-stimulated conditions (in the presence of 10 nM estradiol).
Figure 4F:
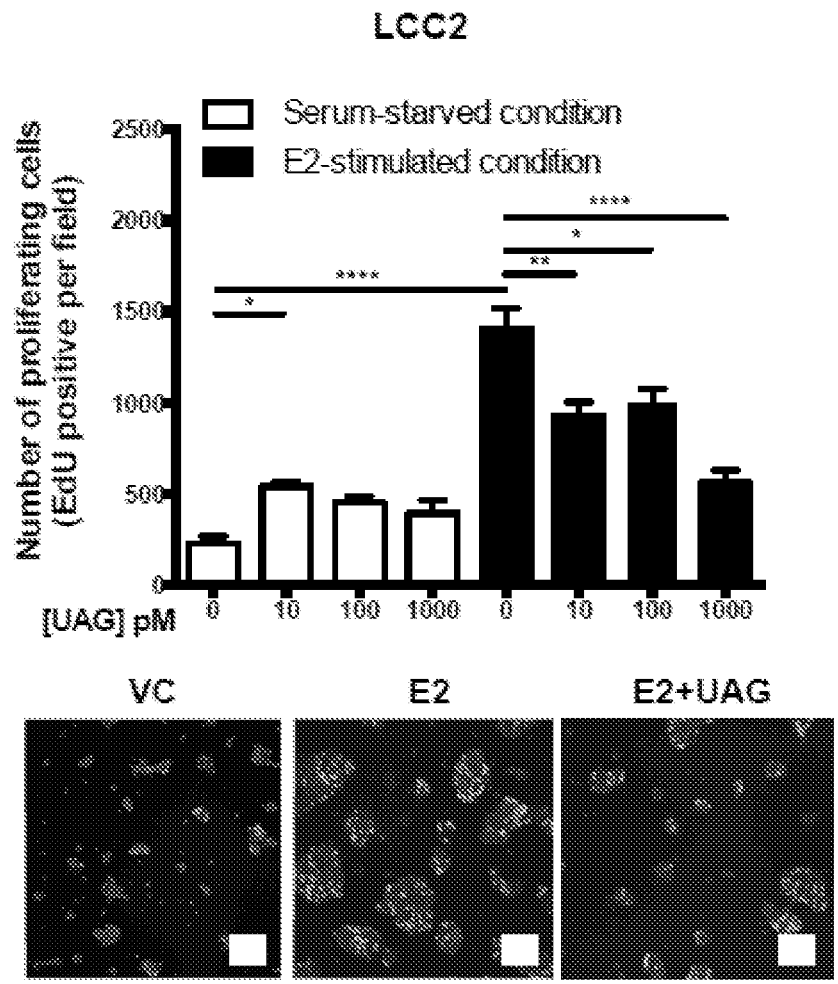
FIGS. 4F-4G shows the effect of des-acyl ghrelin on LCC2 cells under basal, serum-stimulated and in the presence of oestradiol (10 nM). Representative images (10× magnification) of LCC2 treated under basal conditions and in the presence of oestradiol (10 nM). Hoechst nuclear stain (blue) and EdU (green) measure proliferating cells. Scale bars represent 100 μm. Experiment was performed in triplicate and repeated at least twice. (n=3; * P<0.05,  P≤0.005, * P≤0.0005, **** P≤0.0001).
Figure 4G:
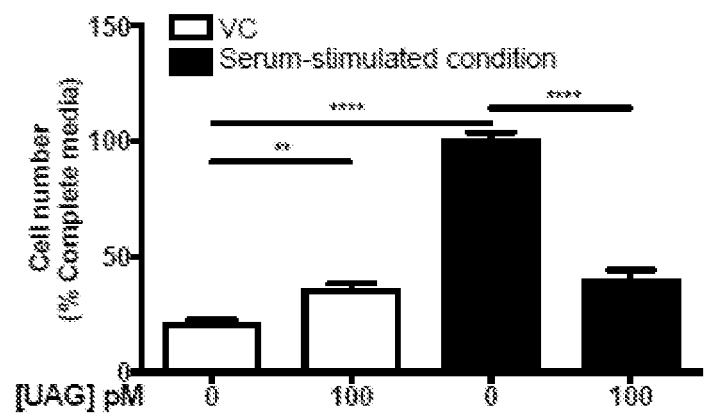
Figure 4H:
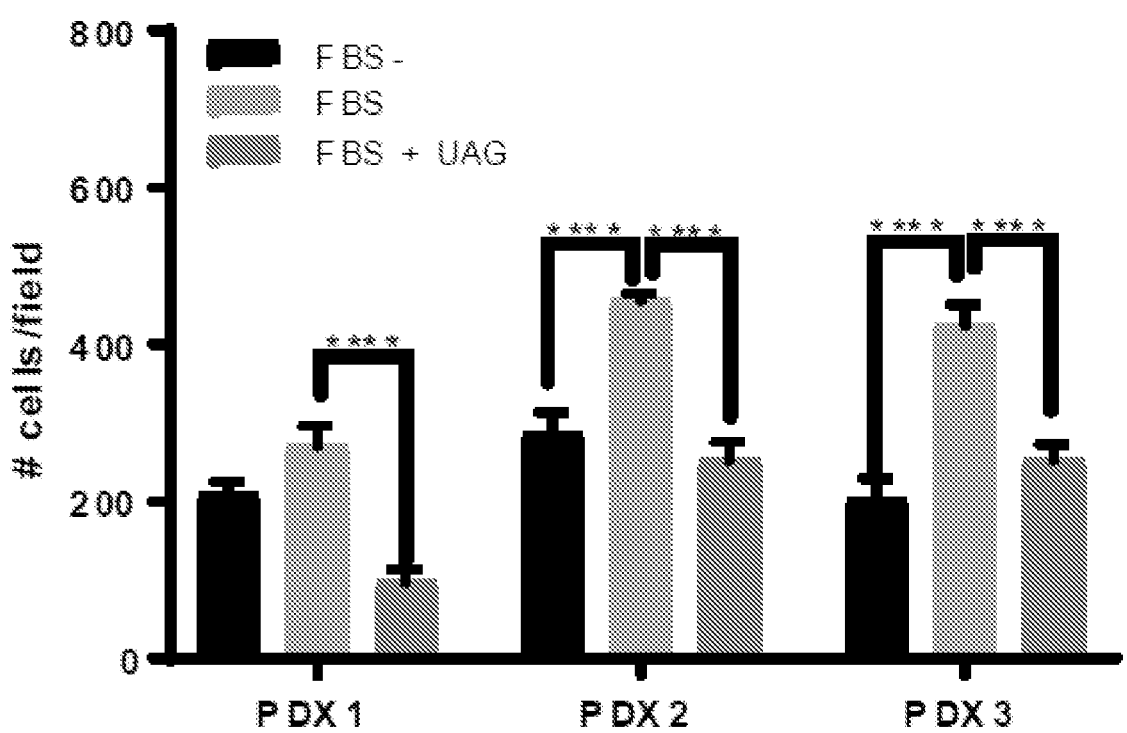
FIG. 4H shows that des-acyl ghrelin (100 μM) significantly inhibited the growth of WT RAS/RAF patient-derived breast cancer cells under serum-starved and serum-stimulated condition. UAG: des-acyl ghrelin; VC: vehicle control.
Figure 5A:
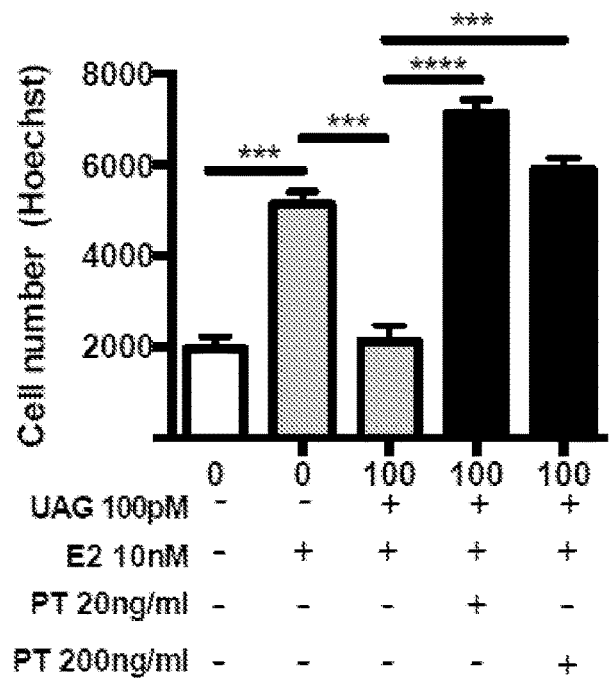
FIGS. 5A-5E show that the effect of des-acyl ghrelin on proliferation involves $G\alpha_i$, and MAPK signaling.
Figure 5B:
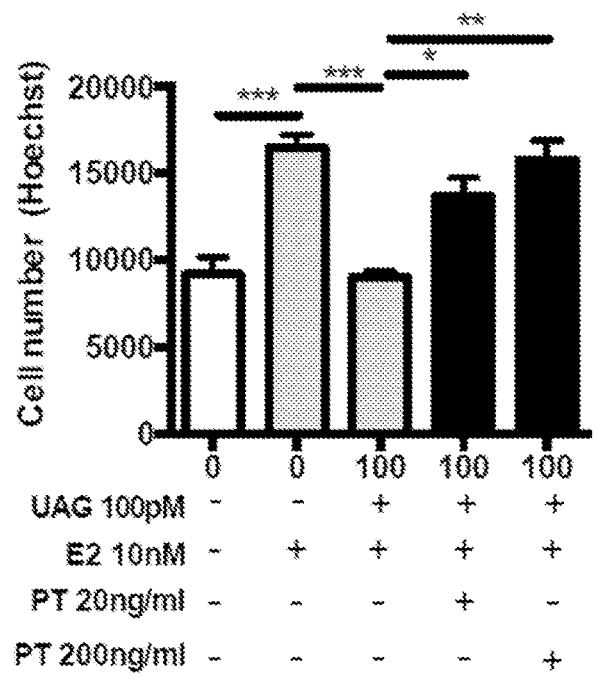
Figure 5C:
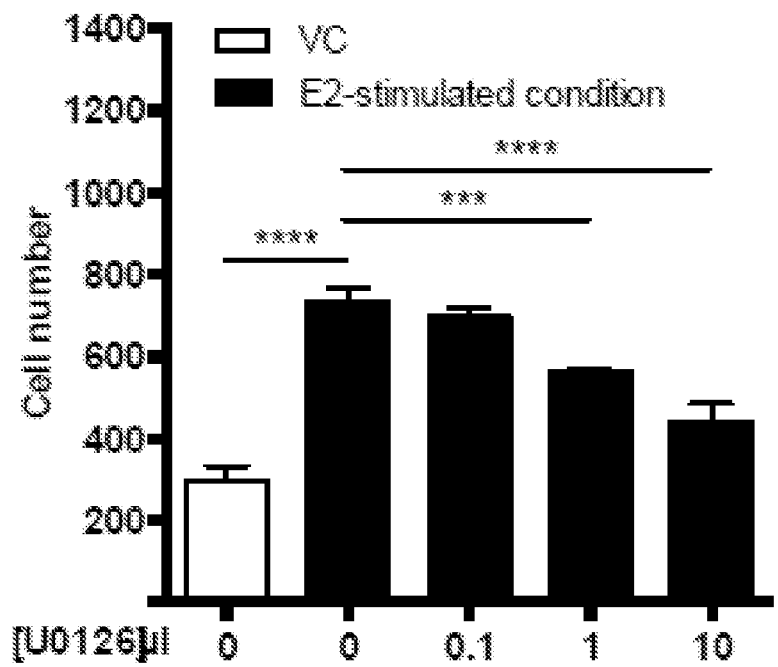
Figure 5D:
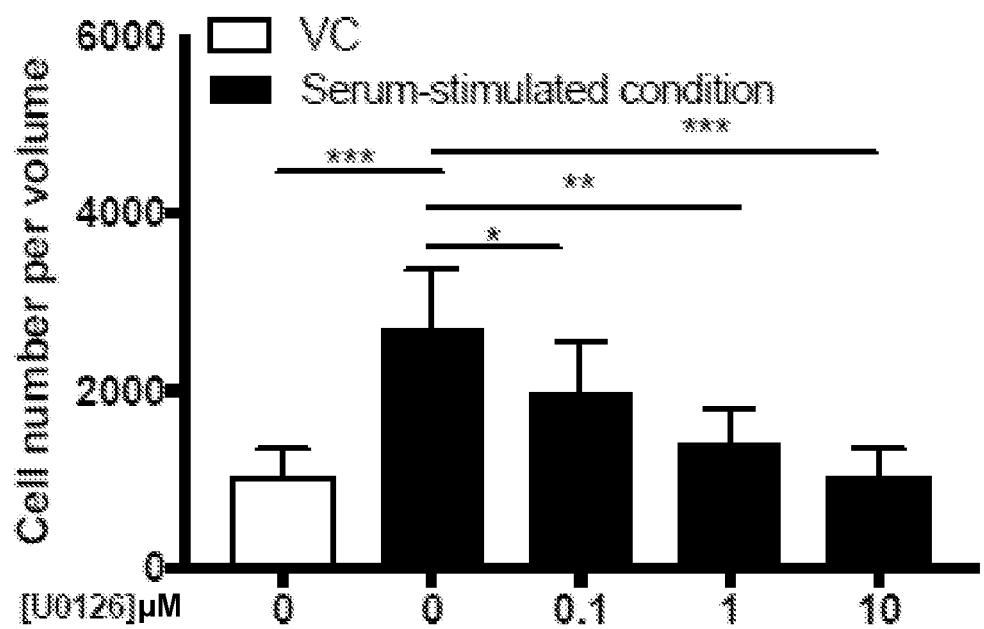
Figure 5E:
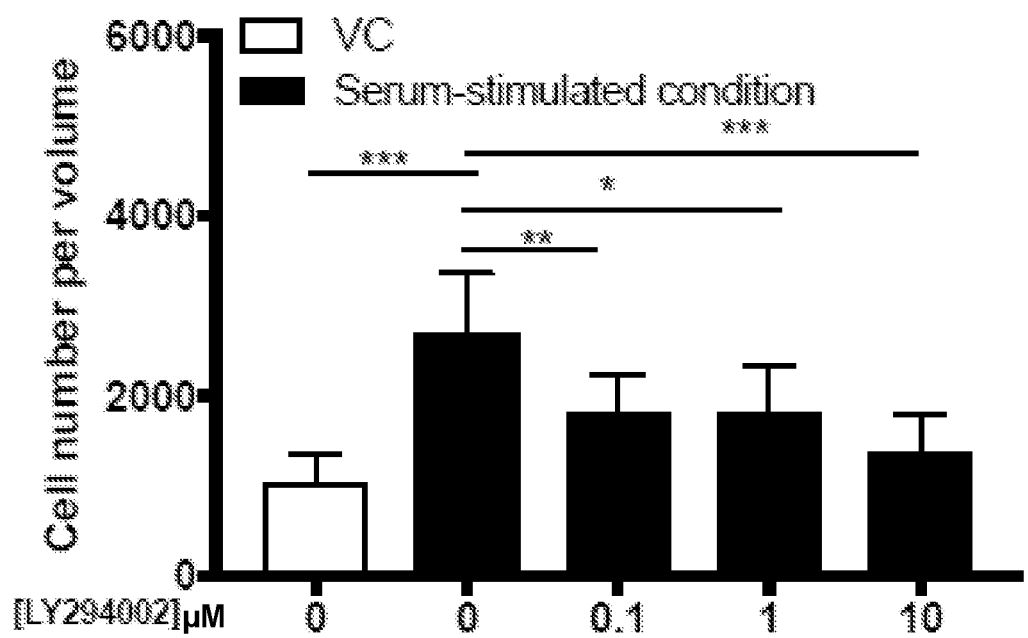
Figure 11A:
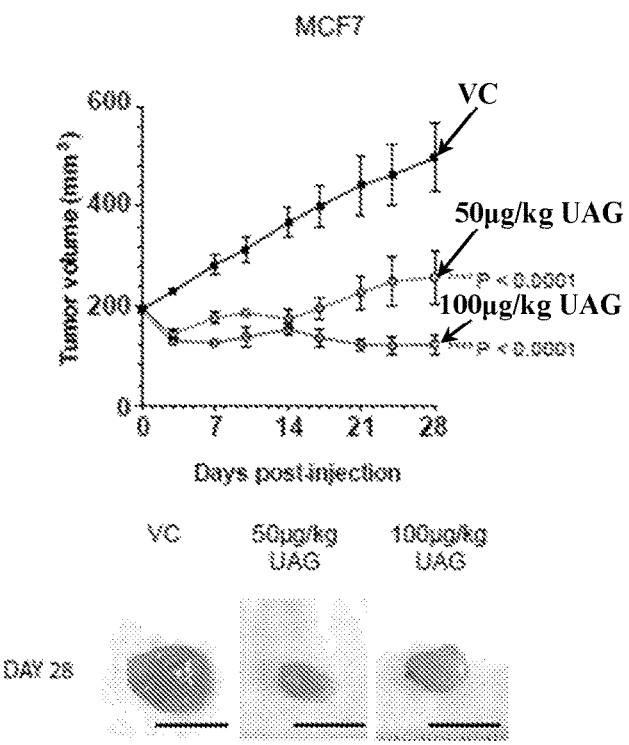
Figure 11B:
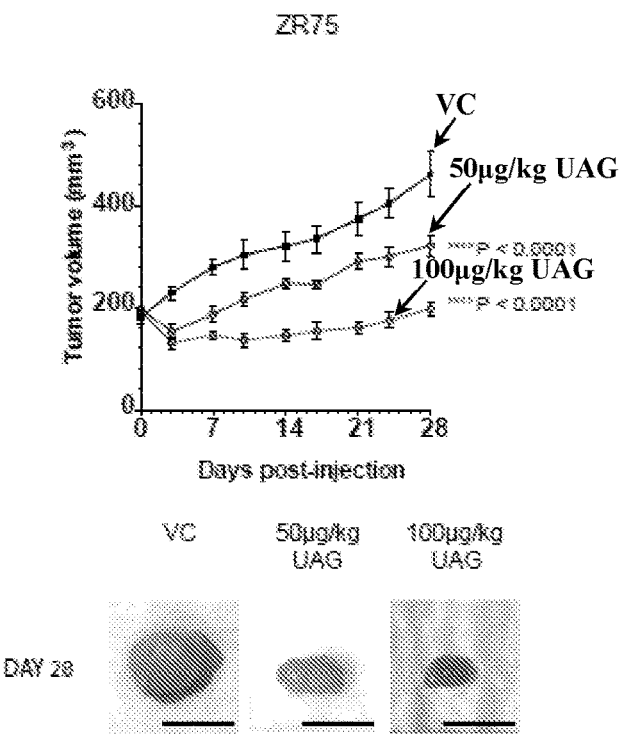
Figure 11C:
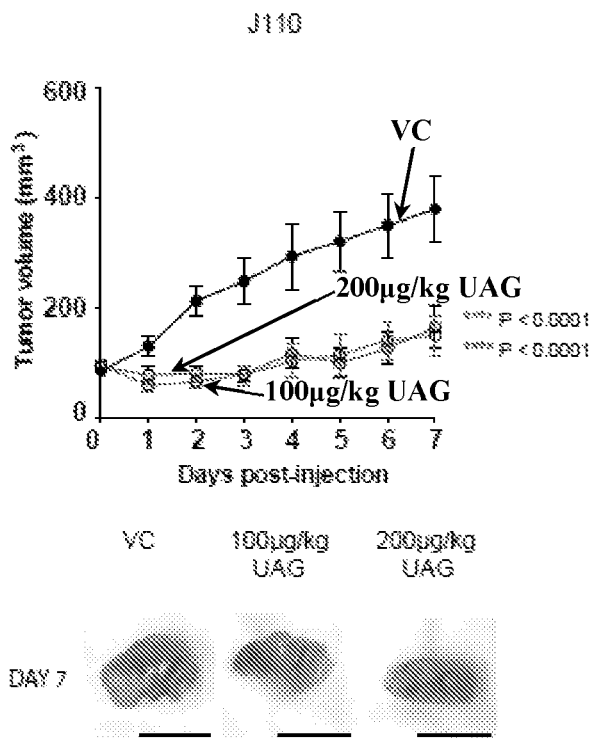
Figure 11D:
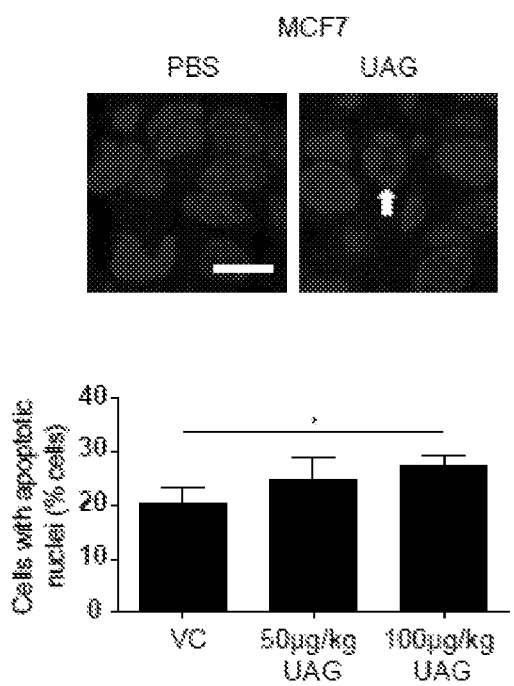
Figure 11G:
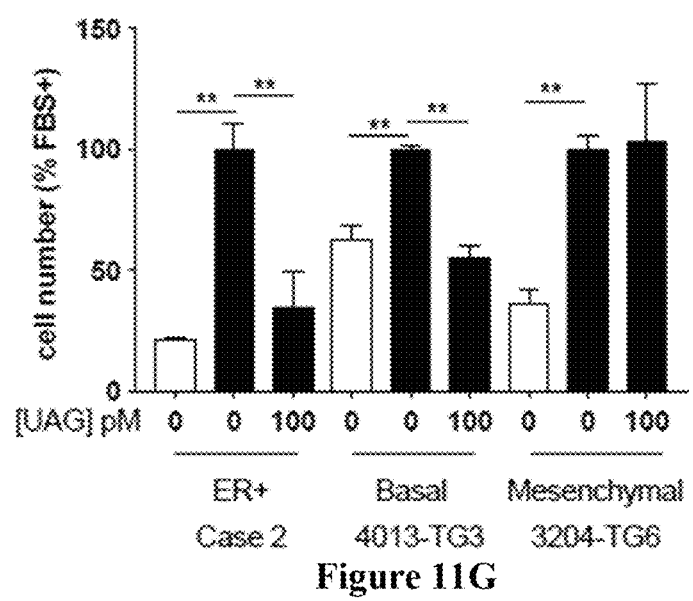
Figure 11H:
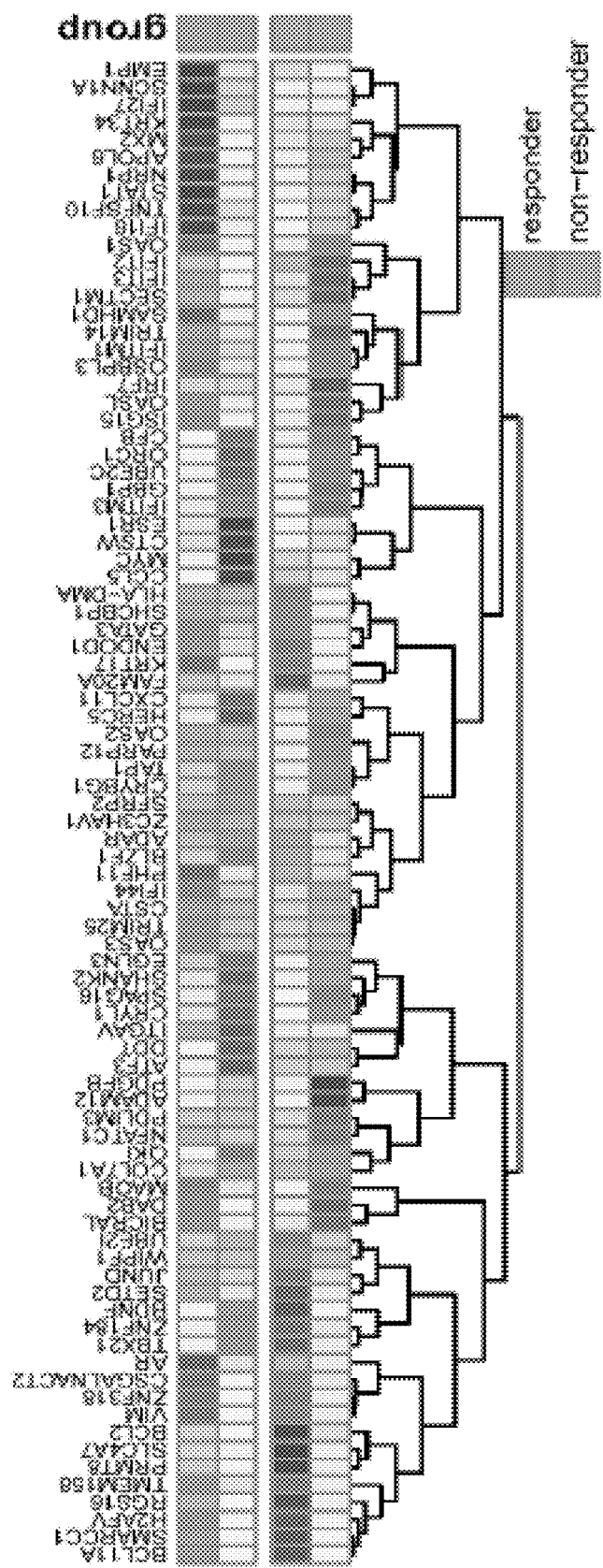
Figure 19A:
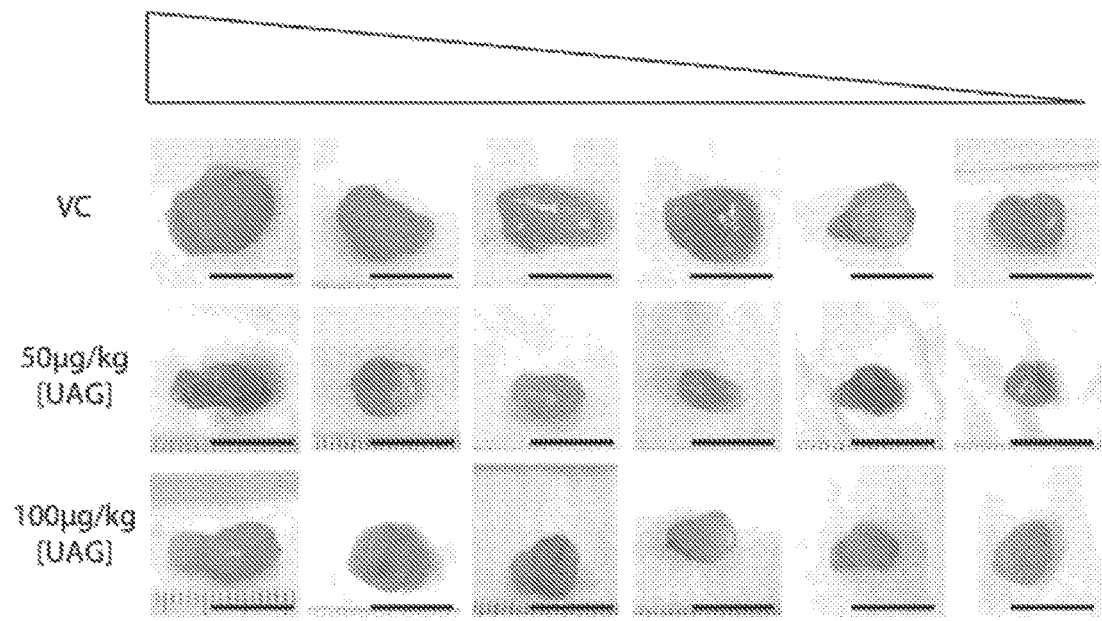
FIGS. 19A-19G show that unacylated ghrelin (UAG) and cyclic analog AZP531 inhibit tumor growth in xenograft models and patient-derived tumor cells.
Figure 19B:
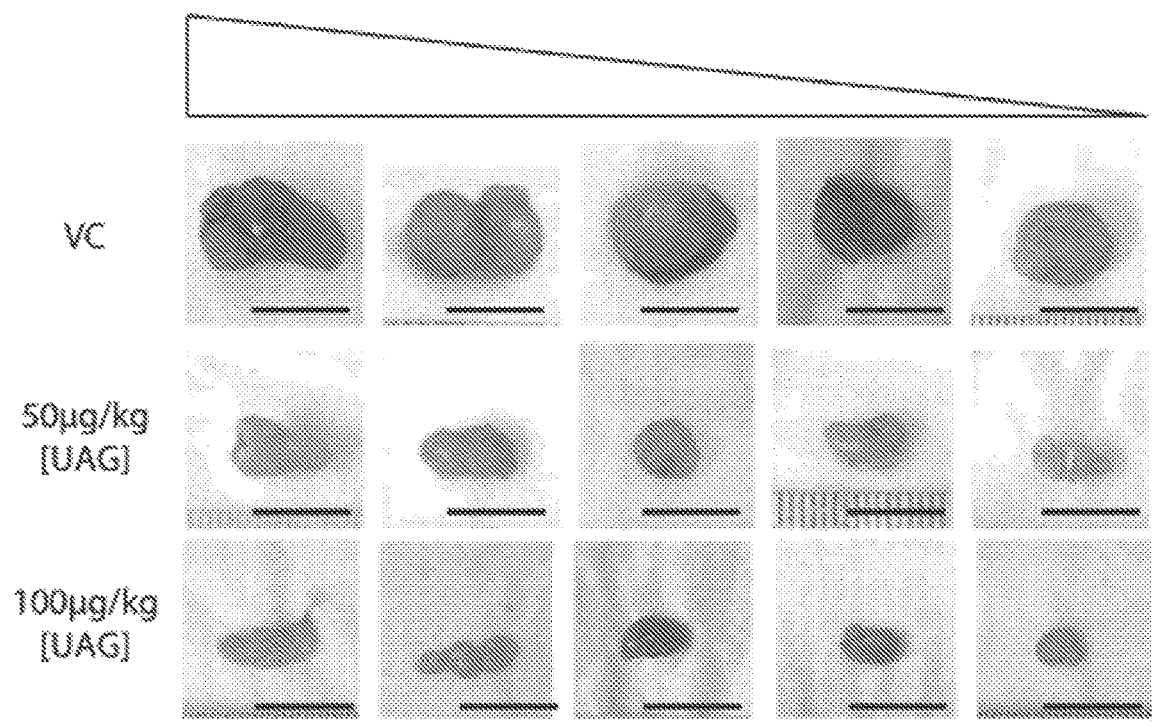
Figure 19C:
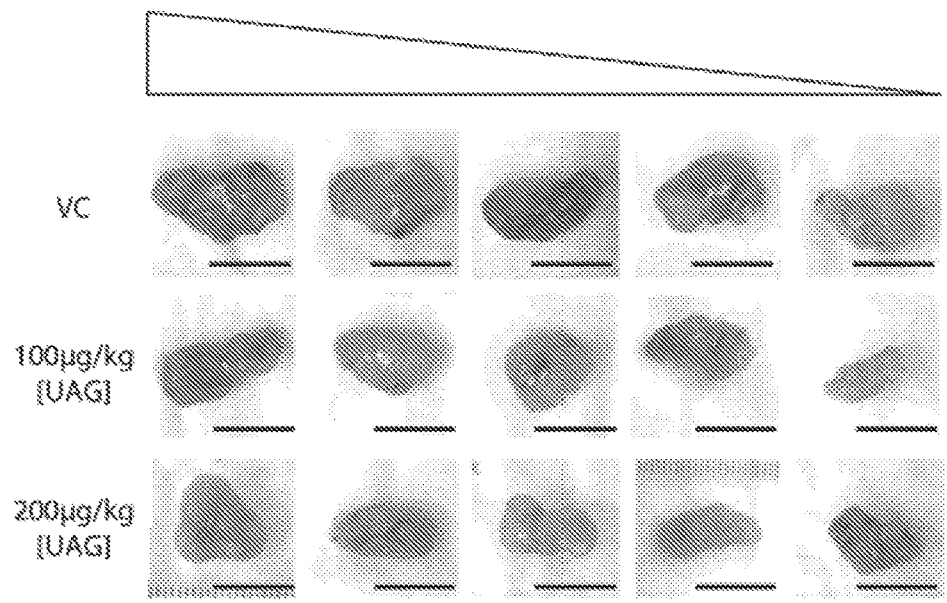
Figure 19D:
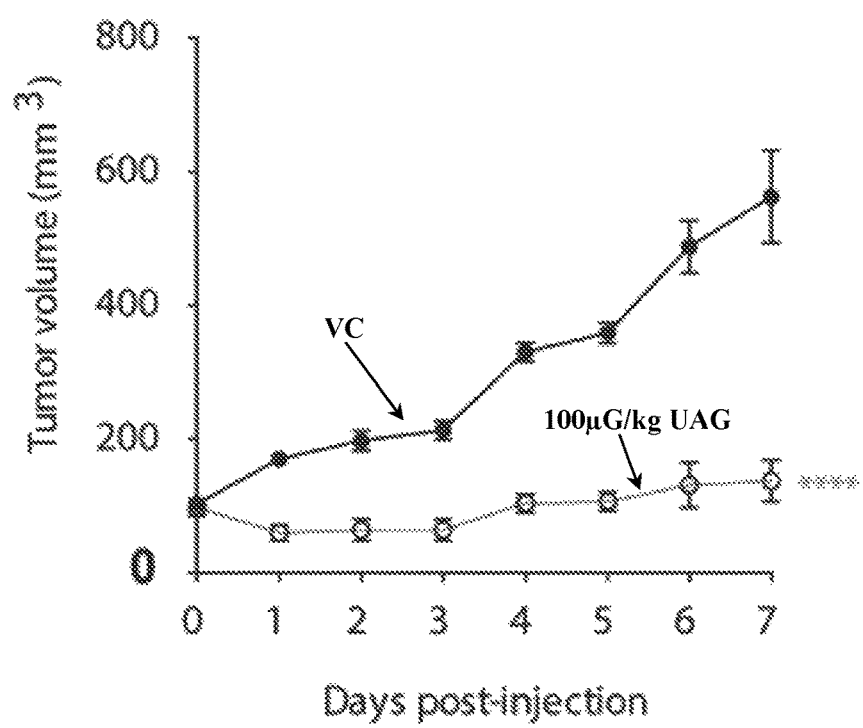
Figure 19E:
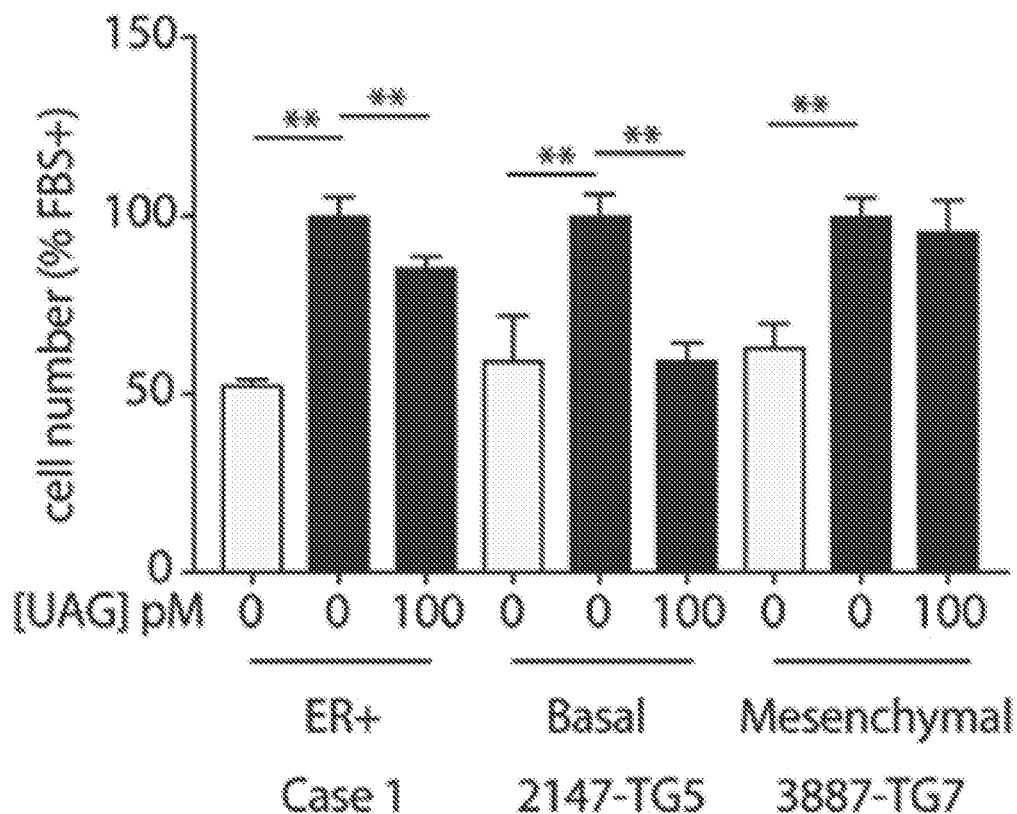

Example 6: Unacylated Ghrelin and Cyclic Analog AZP-531 Inhibit Tumor Growth in Xenograft Models and Patient-Derived Tumor Cells The effect of unacylated ghrelin on tumor growth in vivo was examined in orthotopic xenograft and allograft mouse models. As shown in FIGS. 4A-4B, 11A-11B, and 19A-19B in MCF7 and ZR75 xenografts, daily s.c. injection of 50 µg/kg and 100 µg/kg unacylated ghrelin led to a significant reduction in tumor volume. In the J110 allograft model, unacylated ghrelin caused a significant reduction in tumor growth at 100 µg/kg and 200 µg/kg, as shown in FIGS. 4C and 11C). Effects of unacylated ghrelin to suppress the growth of J110 cells was not dependent on the host immune context, as similar results were obtained when cells were xenografted in Balb/c nude immunocompromised mice (FIGS. 19C-19D). The degree of apoptosis in tumors at endpoint was quantified by counting the percentage of cells with pyknotic nuclei in tumors. As shown in FIGS. 4D and 11D-11F, unacylated ghrelin significantly increased the number of apoptotic cells in MCF7, ZR75 and J110 xenografts/allografts. The effects of unacylated ghrelin were also examined in patient-derived breast cancer cells. Unacylated ghrelin at 100 pM caused a significant reduction in the serum-induced growth of ER+ breast cancer cells and the basal-like subset of TNBC cells, but not mesenchymal TNBCs (FIGS. 11G, 19E and 13). BRAF and KRAS mutation status has not been characterized in these patient samples. Interestingly, Ingenuity Pathway Analysis (causal analysis) of gene expression indicated that MAPK-target genes were differentially expressed between responsive and non-responsive TNBC patient-derived samples, such that non-responsive cells had gene expression consistent with activation of MAPK signaling.

Figure 12A:
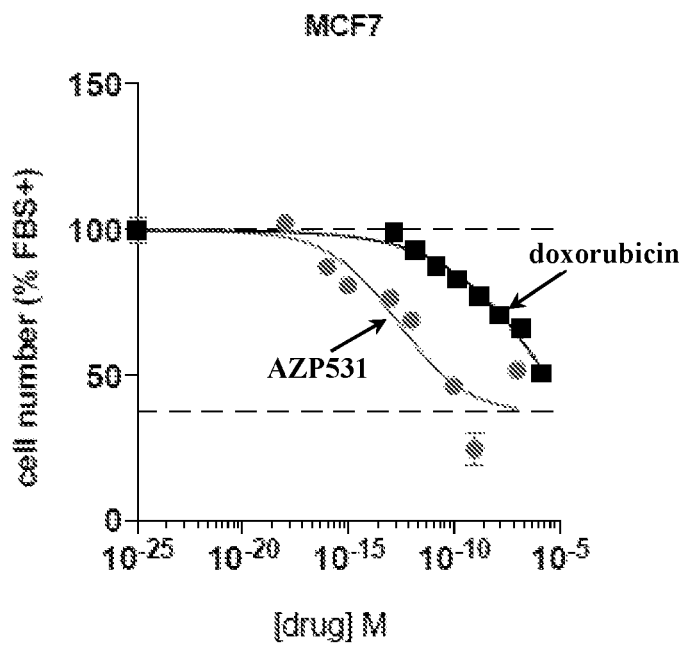
Figure 12B:
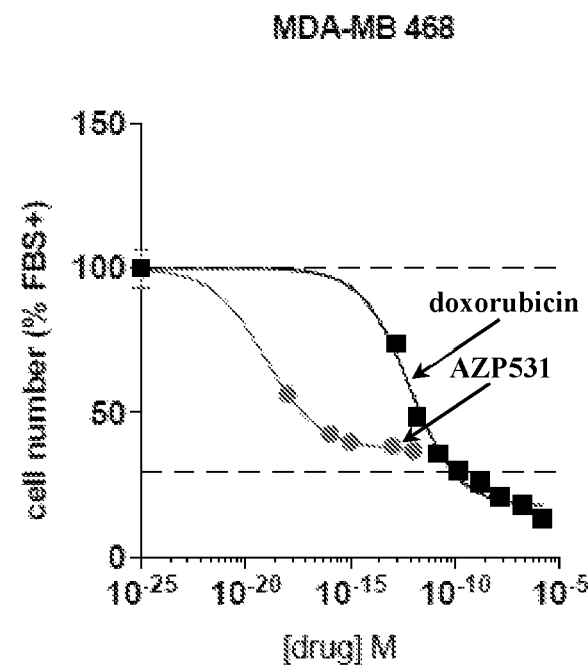
Figure 12E:
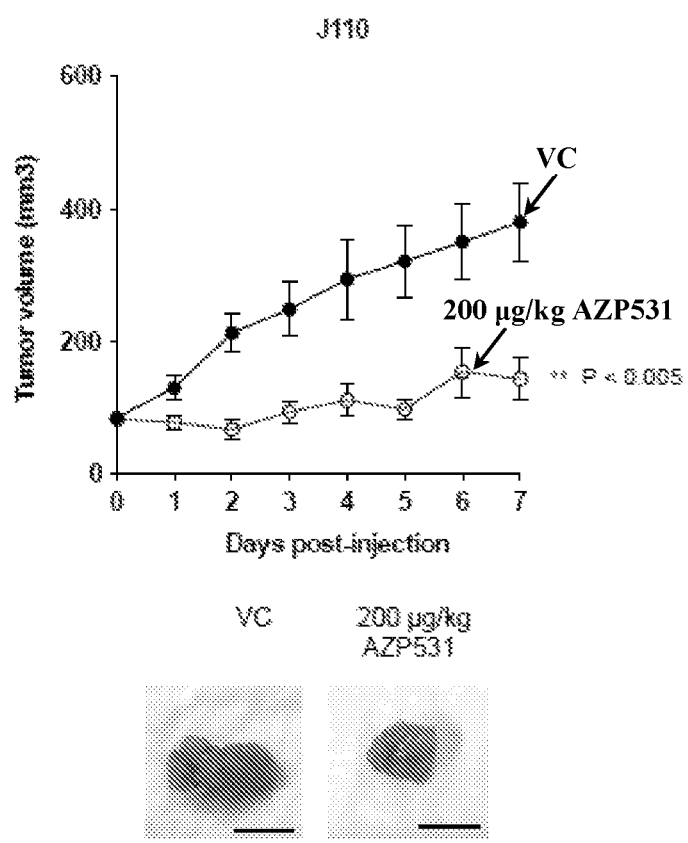
Figure 19F:
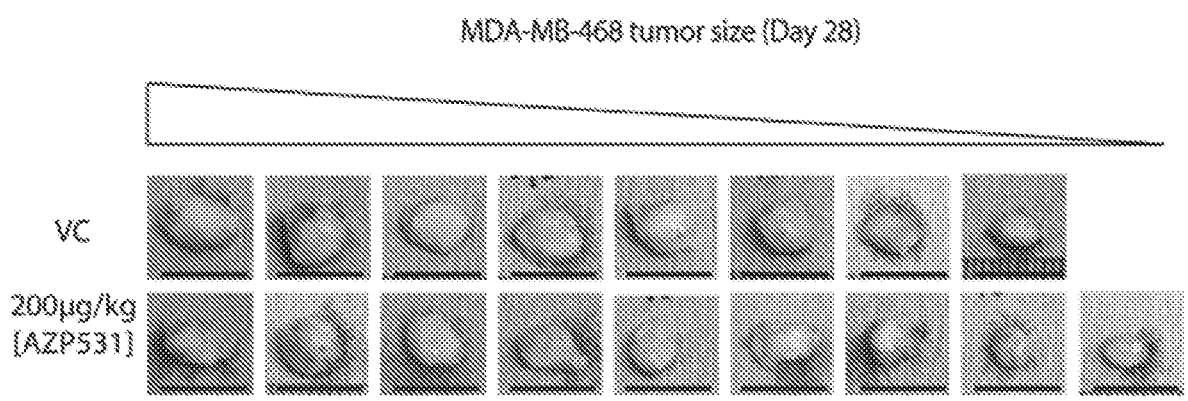
Figure 19G:
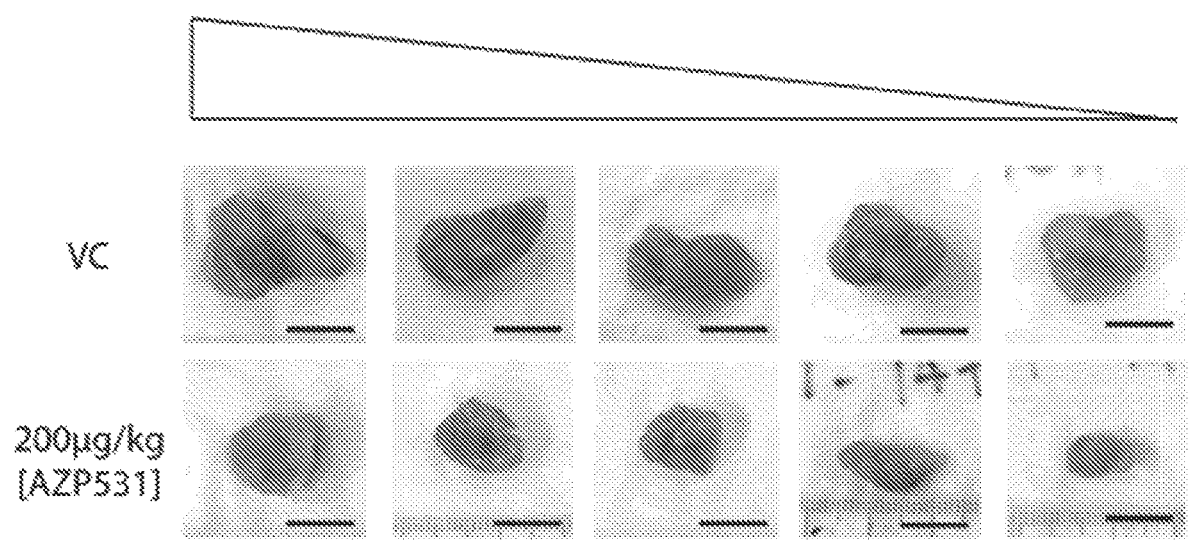

Example 7: Unacylated Ghrelin and Cyclic Analog AZP531 Inhibit Breast Cancer Cell Growth In Vitro, Ex Vivo and In Vivo The effect of unacylated ghrelin analog, AZP531, on breast cancer cell growth was next examined in MCF7, MDA-MB-468, and patient-derived TNBC cells, and compared to chemotherapeutic doxorubicin. As shown in FIGS. 12A-12C, AZP531 caused the dose-dependent inhibition of the serum-stimulated growth of cells with greater potency than doxorubicin, but unlike doxorubicin, did not reduce cell number beyond that which was stimulated by serum. Importantly, AZP531 caused the suppression of cell growth in preclinical models, including TNBC MDA-MB-468 xenografts (FIGS. 12D and 19F) and ER+J110 allografts, at 200 µg/kg (FIGS. 12E and 19G).

EQUIVALENTS

The present technology is not to be limited in terms of the particular embodiments described in this application, which are intended as single illustrations of individual aspects of the present technology. Many modifications and variations of this present technology can be made without departing from its spirit and scope, as will be apparent to those skilled in the art. Functionally equivalent methods and apparatuses within the scope of the present technology, in addition to those enumerated herein, will be apparent to those skilled in the art from the foregoing descriptions. Such modifications and variations are intended to fall within the scope of the present technology. It is to be understood that this present technology is not limited to particular methods, reagents, compounds compositions or biological systems, which can, of course, vary. It is also to be understood that the terminology used herein is for the purpose of describing particular embodiments only, and is not intended to be limiting.

In addition, where features or aspects of the disclosure are described in terms of Markush groups, those skilled in the art will recognize that the disclosure is also thereby described in terms of any individual member or subgroup of members of the Markush group As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like, include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

All patents, patent applications, provisional applications, and publications referred to or cited herein are incorporated by reference in their entirety, including all figures and tables, to the extent they are not inconsistent with the explicit teachings of this specification.

The invention claimed is:

1. A method for treating cancer in a subject diagnosed with or suffering from cancer, comprising administering to the subject an effective amount of ghrelin, des-acyl ghrelin, or an analog thereof, wherein the cancer does not comprise a mutation in BRAF, HRAS, and KRAS, wherein the subject is a mammal, and wherein the analog is a cyclic peptide comprising the amino acid sequence SPEHORVQ (SEQ ID NO: 4).

2. The method of claim 1, wherein the cancer is colorectal cancer or breast cancer.

3. The method of claim 2, wherein the breast cancer is ER$^+$/PR$^+$/HER2$^-$ breast cancer ("Luminal A" breast cancer"), ER$^+$/PR$^+$/HER2$^+$ ("Luminal B" breast cancer"), ER$^-$/PR$^-$/HER2$^+$ (HER2-positive breast cancer), or ER$^-$/PR$^-$/HER2$^-$ ("Triple Negative" breast cancer (TNBC)), optionally wherein the TNBC has a subtype that is basal-like or mesenchymal-like.

4. The method of claim 1, wherein the subject harbors at least one mutation in one or more genes selected from the group consisting of CDKN2A, PIK3CA, TP53, PTEN, RB1, SMAD4, and NF1.

5. The method of claim 1, wherein the cancer is resistant to tamoxifen.

6. The method of claim 1, wherein the subject exhibits at least one symptom selected from the group consisting of swelling in one or both breasts, redness or pitting of breast skin, change in breast size or shape, nipple discharge, breast pain, lumps on or inside the breast, itchy breasts, peeling or flaking of nipple skin, skin irritation or dimpling, nipple pain, nipple retraction, and lumps or swelling in underarm lymph nodes, diarrhea, constipation, narrowing of stool, rectal bleeding, dark or bloody stool, cramping, abdominal pain, fatigue, and unintended weight loss.

7. The method of claim 1, wherein the ghrelin, des-acyl ghrelin, or analog is administered intravenously, intramuscularly, intraarterially, intrathecally, intracapsularly, intraorbitally, intradermally, intraperitoneally, transtracheally, subcutaneously, intracerebroventricularly, orally, topically, intratumorally, or intranasally.

8. The method of claim 1, wherein the ghrelin, des-acyl ghrelin, or analog is sequentially, simultaneously, or separately administered with at least one additional therapeutic agent, optionally wherein the at least one additional therapeutic agent is selected from the group consisting of selective ER modulators (SERMs), selective estrogen receptor down-regulators (SERDs), aromatase inhibitors (AIs), chemotherapeutic agents, anthracyclines, 5-fluorouracil (5-FU), cyclophosphamide, carboplatin, cisplatin, vinorelbine, capecitabine, gemcitabine, ixabepilone, eribulin, irinotecan, oxaliplatin, trifluridine, tipiracil, tamoxifen, Fulvestrant (ICI 164384), exemestane, anastrozole, and letrozole.

9. The method of claim 1, wherein administration of the ghrelin, des-acyl ghrelin, or analog results in reduction in tumor size, reduced metastasis, and/or partial or complete remission compared to an untreated control subject suffering from cancer.

10. The method of claim 8, wherein the anthracyclines are selected from the group consisting of doxorubicin, pegylated liposomal doxorubicin, and epirubicin, and the taxanes are selected from the group consisting of paclitaxel, docetaxel, and albumin-bound paclitaxel.

* * * * *

SEQUENCE LISTING

```
<160> NUMBER OF SEQ ID NOS: 22

<210> SEQ ID NO 1
<211> LENGTH: 117
<212> TYPE: PRT
<213> ORGANISM: Homo sapiens

<400> SEQUENCE: 1

Met Pro Ser Pro Gly Thr Val Cys Ser Leu Leu Leu Gly Met Leu
1               5                   10                  15

Trp Leu Asp Leu Ala Met Ala Gly Ser Ser Phe Leu Ser Pro Glu His
                20                  25                  30

Gln Arg Val Gln Gln Arg Lys Glu Ser Lys Lys Pro Pro Ala Lys Leu
            35                  40                  45

Gln Pro Arg Ala Leu Ala Gly Trp Leu Arg Pro Glu Asp Gly Gly Gln
        50                  55                  60

Ala Glu Gly Ala Glu Asp Glu Leu Glu Val Arg Phe Asn Ala Pro Phe
65                  70                  75                  80

Asp Val Gly Ile Lys Leu Ser Gly Val Gln Tyr Gln Gln His Ser Gln
                85                  90                  95

Ala Leu Gly Lys Phe Leu Gln Asp Ile Leu Trp Glu Glu Ala Lys Glu
            100                 105                 110

Ala Pro Ala Asp Lys
        115

<210> SEQ ID NO 2
<211> LENGTH: 28
<212> TYPE: PRT
<213> ORGANISM: Homo sapiens

<400> SEQUENCE: 2

Gly Ser Ser Phe Leu Ser Pro Glu His Gln Arg Val Gln Gln Arg Lys
1               5                   10                  15

Glu Ser Lys Lys Pro Pro Ala Lys Leu Gln Pro Arg
            20                  25

<210> SEQ ID NO 3
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Ser(n-octanoyl)
```

```
<400> SEQUENCE: 3

Gly Ser Ser Phe Leu Ser Pro Glu His Gln Arg Val Gln Gln Arg Lys
1               5                   10                  15

Glu Ser Lys Lys Pro Pro Ala Lys Leu Gln Pro Arg
            20                  25

<210> SEQ ID NO 4
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Ser Pro Glu His Gln Arg Val Gln
1               5

<210> SEQ ID NO 5
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
caccgagcac tgagtgacta cgacc                                           25

<210> SEQ ID NO 6
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
aaacggtcgt agtcactcag tgctc                                           25

<210> SEQ ID NO 7
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
caccgttgct atcattaggg ctatg                                           25

<210> SEQ ID NO 8
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
aaacatagcc ctaatgatag caac                                            24

<210> SEQ ID NO 9
<211> LENGTH: 25
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 9
caccgtgaag ctggttattc agaag                                              25

<210> SEQ ID NO 10
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
aaaccttctg aataaccagc ttcac                                              25

<210> SEQ ID NO 11
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
caccggaccc gcgtaaagac cacg                                               24

<210> SEQ ID NO 12
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
aaaccgtggt ctttacgcgg gtccc                                              25

<210> SEQ ID NO 13
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
caccgctttg ccgacccctc cagag                                              25

<210> SEQ ID NO 14
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
aaacctctgg aggggtcggc aaagc                                              25

<210> SEQ ID NO 15
<211> LENGTH: 25
<212> TYPE: DNA
<213> ORGANISM: Artificial Sequence
<220> FEATURE:
```

<223> OTHER INFORMATION: Description of Artificial Sequence: Synthetic
      oligonucleotide

<400> SEQUENCE: 15
caccggcgtc atccggaggc tctgg                                           25

<210> SEQ ID NO 16
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
aaacccagag cctccggatg acgcc                                           25

<210> SEQ ID NO 17
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
caccggatcg accgcaactt acggg                                           25

<210> SEQ ID NO 18
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18
aaaccccgta agtaagttgc ggtcgatcc                                       29

<210> SEQ ID NO 19
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
caccgtcatg aggatggcta ttcag                                           25

<210> SEQ ID NO 20
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20
aaacctgaat agccatcctc atgac                                           25

<210> SEQ ID NO 21
<211> LENGTH: 25
<212> TYPE: DNA
<213> ORGANISM: Artificial Sequence
<220> FEATURE:
<223> OTHER INFORMATION: Description of Artificial Sequence: Synthetic

```
    oligonucleotide

<400> SEQUENCE: 21
caccgagtct aactacattc caact                                            25

<210> SEQ ID NO 22
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22
aaacagttgg aatgtagtta gactc                                            25
```